(12) United States Patent
Lee et al.

(10) Patent No.: US 11,534,462 B2
(45) Date of Patent: Dec. 27, 2022

(54) ANTIBODY OR ANTIGEN BINDING FRAGMENT THEREOF FOR SPECIFICALLY RECOGNIZING B CELL MALIGNANCY, CHIMERIC ANTIGEN RECEPTOR COMPRISING SAME AND USE THEREOF

(71) Applicant: ABCLON INC., Seoul (KR)

(72) Inventors: Jong Seo Lee, Gyeonggi-do (KR); Kyu Tae Kim, Gyeonggi-do (KR); Bong Kook Ko, Seoul (KR); Ki Hyun Kim, Seoul (KR)

(73) Assignee: ABCLON INC., Seoul (KR)

( * ) Notice: Subject to any disclaimer, the term of this patent is extended or adjusted under 35 U.S.C. 154(b) by 349 days.

(21) Appl. No.: 16/768,412

(22) PCT Filed: Dec. 6, 2018

(86) PCT No.: PCT/KR2018/015445
§ 371 (c)(1),
(2) Date: May 29, 2020

(87) PCT Pub. No.: WO2019/112347
PCT Pub. Date: Jun. 13, 2019

(65) Prior Publication Data
US 2020/0384023 A1   Dec. 10, 2020

(30) Foreign Application Priority Data
Dec. 6, 2017   (KR) ........................ 10-2017-0166969

(51) Int. Cl.
*A61K 35/17*   (2015.01)
*A61P 31/14*   (2006.01)
(Continued)

(52) U.S. Cl.
CPC .............. *A61K 35/17* (2013.01); *A61P 31/14* (2018.01); *C07K 14/7051* (2013.01); *C07K 16/2803* (2013.01); *C12N 15/86* (2013.01)

(58) Field of Classification Search
CPC .......... A61K 35/17; A61P 31/14; A61P 35/00; C07K 14/7051; C07K 16/2803;
(Continued)

(56) References Cited

U.S. PATENT DOCUMENTS 8,097,703 B2   1/2012   Rao-Naik et al.
8,679,492 B2   3/2014   Blein et al.
(Continued)

FOREIGN PATENT DOCUMENTS

CN   106554414 A   4/2017
JP   2008-546647 A   12/2008
(Continued)

OTHER PUBLICATIONS

Emmons, K. M., et al (Mar. 2017) Realizing the Potential of Cancer Prevention—The Role of Implementation Science N Engl J Med 376(10); 986-990 (Year: 2017).*

*Primary Examiner* — Joanne Hama
*Assistant Examiner* — Audrey L Buttice
(74) *Attorney, Agent, or Firm* — Harness, Dickey & Pierce, P.L.C.

(57) ABSTRACT

The present invention relates to a new antibody or an antigen binding fragment thereof for use in the treatment of cancer by targeting a B cell malignancy, a chimeric antigen receptor comprising the same, and a use of the same. The antibody of the present invention is an antibody for specifically binding to CD19 that is highly expressed in cancer cells (particularly, blood cancer), has very low homology to a CDR sequence thereof compared to a CDR sequence of a conventional
(Continued)

CD19 target antibody so that the sequence thereof is unique, and specifically binds to an epitope that is different from a FMC63 antibody fragment binding to CD19 of the conventional art. A cell expressing the chimeric antigen receptor comprising an anti-CD19 antibody or the antigen binding fragment of the present invention induces immune cell activity in response to a positive cell line expressing CD19.

8 Claims, 18 Drawing Sheets

Specification includes a Sequence Listing.

(51) Int. Cl.
*C07K 14/725* (2006.01)
*C07K 16/28* (2006.01)
*C12N 15/86* (2006.01)

(58) Field of Classification Search
CPC ............................ C07K 16/28; C07K 16/2896;
C07K 2319/03; C07K 2319/33; C07K
2317/62; C12N 15/86; C12N 2510/00;
C12N 5/0636
See application file for complete search history.

(56) References Cited

U.S. PATENT DOCUMENTS

| | | | |
|---|---|---|---|
| 9,074,002 | B2 | 7/2015 | Tonks et al. |
| 9,701,758 | B2 | 7/2017 | Cooper et al. |
| 2006/0280738 | A1 | 12/2006 | Tedder |
| 2009/0246195 | A1 | 10/2009 | Tedder |
| 2012/0164673 | A1 | 6/2012 | Tonks et al. |
| 2016/0152723 | A1* | 6/2016 | Chen ................. C07K 16/2896 435/254.2 |

FOREIGN PATENT DOCUMENTS

| | | | |
|---|---|---|---|
| JP | 2016-520074 | | 7/2016 |
| KR | 10-2007-0114144 A | | 11/2007 |
| KR | 10-2011-0104032 A | | 9/2011 |
| KR | 10-2011-0125664 A | | 11/2011 |
| KR | 10-2015-0132850 A | | 11/2015 |
| KR | 10-2017-0057298 A | | 5/2017 |
| WO | WO-2010126590 A1 * | 11/2010 | ............ C07K 16/40 |
| WO | WO-2014/184143 A1 | | 11/2014 |
| WO | WO-2016/139487 A1 | | 9/2016 |
| WO | WO-2017/066136 A2 | | 4/2017 |

OTHER PUBLICATIONS

Cuzick, J. (Aug. 2017) Preventive therapy for cancer Lancet Oncol 18; e472-e482 (Year: 2017).*
Chailyan, A., et al. (2011) The association of heavy and light chain variable domains in antibodies: implications for antigen specificity FEBS Journal 278; 2858-2866 (Year: 2011).*
2nd Office Action from corresponding Japanese Patent Application No. 2020-530356, dated Jan. 5, 2022.
Office Action from corresponding Japanese Patent Application No. 2020-530356, dated May 18, 2021.
De Oliveira, et al. (2013) "A CD19/Fc fusion protein for detection of anti-CD19 chimeric antigen receptors.", *Journal of Translational Medicine*, 11:23, pp. 1-9.
Notice of Allowance of Korean Patent Application No. 10-2018-0156433, dated Jul. 10, 2020, No English translation, provided. Considered to extent possible.
Extended European Search Report from corresponding European Patent Application No. 18886531.52, dated Jan. 22, 2021.
Kalos, et al. (2011) "T Cells with Chimeric Antigen Receptors Have Potent Antitumor Effects and Can Establish Memory in Patients with Advanced Leukemia." *Sci Transl Med*, 3(95):1-21 (Aug. 10, 2011).
Kochenderfer, et al. (2010) "Eradication of B-lineage cells and regression of lymphoma in a patient treated with autologous T cells genetically engineered to recognize CD19." *Blood*, 116(20):4099-4102, (Nov. 18, 2010).
Kochenderfer, et al. (2012) "B-cell depletion and remissions of malignancy along with cytokine-associated toxicity in a clinical trial of anti-CD19 chimeric-antigen-receptor-transduced T cells." *Blood*, 119(12):2709-2720, (Mar. 22, 2012).
Kochenderfer, et al. (2013) "Treating B-cell cancer with T cells expressing anti-CD19 chimeric antigen receptors." *Nat Rev Clin Oncol*, 10(5):267-276, (May 2013).
Maude, et al. (2014) "Chimeric Antigen Receptor T Cells for Sustained Remissions in Leukemia." *N Engl J Med*, 371:16, pp. 1507-1517, (Oct. 16, 2014).
Nicholson, et al. (1997) "Construction and characterisation of a functional CD19 specific single chain Fv fragment for immunotherapy of B lineage leukaemia and lymphoma." *Molecular Immunology*, 34(16-17):1157-1165.
Porter, et al. (2011) "Chimeric Antigen Receptor-Modified T Cells in Chronic Lymphoid Leukemia." *N Engl J Med*, 365:8 pp. 725-733, (Aug. 25, 2011).
Topp, et al. (2014) "Phase II Trial of the Anti-CD19 Bispecific T Cell-Engager Blinatumomab Shows Hematologic and Molecular Remissions in Patients With Relapsed or Refractory B-Precursor Acute Lymphoblastic Leukemia." *Journal of Clinical Oncology*, 32(36):4134-4142.
International Search Report from corresponding PCT Application No. PCT/KR2018/015445, dated May 31, 2019, with English Translation.

* cited by examiner

| | Signal peptide | scFv | Hinge/Spacer | TM | Co-stimulatory | | |
|---|---|---|---|---|---|---|---|
| CAR1 | CD8 | scFv | CD8 | CD8 | CD137 | CD3z | |
| CAR2 | CD8 | scFv | CD28 | CD8 | CD137 | CD3z | |
| CAR3 | CD8 | scFv | Fc | CD8 | CD137 | CD3z | |
| CAR4 | CD8 | scFv | CD8 | CD28 | CD28 | CD3z | |
| CAR5 | CD8 | scFv | CD8 | ICOS | ICOS | CD3z | |
| CAR6 | CD8 | scFv | CD8 | CD28 | CD28 | CD137 | CD3z |
| CAR7 | CD8 | scFv | CD8 | ICOS | CS3 | CD137 | CD3z |

CAR1–CAR5: 2nd-G CAR
CAR6–CAR7: 3rd-G CAR

FIG. 9

ANTIBODY OR ANTIGEN BINDING FRAGMENT THEREOF FOR SPECIFICALLY RECOGNIZING B CELL MALIGNANCY, CHIMERIC ANTIGEN RECEPTOR COMPRISING SAME AND USE THEREOF

CROSS-REFERENCE TO RELATED APPLICATIONS

This application is a national phase application of PCT Application No. PCT/KR2018/015445, filed on Dec. 6, 2018, which claims the benefit and priority to Korean Patent Application No. 10-2017-0166969, filed Dec. 6, 2017. The entire disclosures of the applications identified in this paragraph are incorporated herein by references.

FIELD

The present disclosure relates to a novel antibody for targeting and treating B cell malignancy, or an antigen binding fragment thereof, a chimeric antigen receptor comprising the same, and a use thereof.

BACKGROUND

B cell malignancies are tumors generated in B cells, which are a type of cell lineage responsible for the immune system of the body. Such a B cell malignancy breaks a normal immune system to decrease the immunity against antigens invading from the outside, finally causing the death of patients. For example, acute lymphocytic leukemia (ALL), which is one of B cell malignancies, refers to a disease in which the lymphoid line of white blood cells becomes malignant, grows in the bone marrow, and spreads to peripheral blood, thus invading the liver, the spleen, the lymph, the cerebrum, the cerebellum, the spinal cord, and so on. Representative of therapies for acute lymphocytic leukemia are chemotherapy, targeted therapy, and allogeneic stem cell transplantation. These therapies have been improved to carry the survival rate of child patients to over 85%. However, there are patients unresponsive to conventional therapies or patients in recurrence, and acute lymphocytic leukemia is the most common cause of cancer and death from cancer among children.

Most lymphoma/leukemia generated from B cell malignancies as well as acute lymphocytic leukemia are characterized by the expression of CD19 antigen on the surface of the cells. On the basis of this feature, various therapies designed to recognize CD19 antigen have been tried. Among such CD19 target therapies, CAR-T cell therapy was used for treatment of blood cancer through the cell death induction mechanism thereof as it was found to increase cytotoxicity for target cells in acute leukemia patients unresponsive to conventional therapies. A high cure rate (27 of 30 cases) was reported as a clinical test result of the therapy. However, in spite of the high response rate thereof, conventional CD19 CAR-T cell therapies were reported to have the problem of causing resistance in 10-20% of the patients treated therewith (Maude et al., N Eng J Med, 2014, 371:1507; Topp et al., J Clin Oncol, 2014, 32:4134). Therefore, there is a need for the development of a novel antibody that binds to a site different from those bound by conventional CD19 targeting antibodies.

Under the background, the present inventors developed an antigen-binding fragment that selectively recognizes CD19-expressing B cells among B cell malignancies and found that the developed antibody binds to CD19 at an epitope different from that targeted by the conventional antibody FMC63. In addition, cytotoxic T cells that express a chimeric antigen receptor comprising the developed antigen-binding fragment retain cytotoxicity.

DETAILED DESCRIPTION

Technical Problem

Leading to the present disclosure, intensive and thorough research into development of a novel antibody binding to a different epitope of CID19 and a chimeric antigen receptor using the same, conducted by the present inventors in order to solve the problem of resistance to conventional CD19-specific CAR-T therapies, resulted in the finding that CD19_12.18 antibody and variants thereof bind to a CD19 epitope site different from those that the conventional antibody FMC63 targets.

Therefore, a purpose of the present disclosure is to provide a novel anti-CD19 antibody and an antigen-binding fragment thereof.

Another purpose of the present disclosure is to provide a chimeric antigen receptor comprising the anti-CD19 antibody or an antigen-binding fragment thereof and dividable into an extracellular domain, a transmembrane domain, and an intracellular signaling domain.

Another purpose of the present disclosure is to provide a pharmaceutical composition comprising cells expressing the chimeric antigen receptor.

Another purpose of the present disclosure is to provide a nucleic acid molecule encoding the antibody, the antigen-binding fragment thereof, or the chimeric antigen receptor.

Another purpose of the present disclosure is to provide a recombinant vector carrying a nucleic acid molecule encoding the antibody, the antigen-binding fragment thereof, or the chimeric antigen receptor.

Another purpose of the present disclosure is to provide a host cell transformed with the recombinant vector.

Other purpose and advantages of the present disclosure will become more apparent from the following detailed description, claims and drawings.

Technical Solution

Claimed in the present disclosure is the disclosure as set forth below:

1. An anti-CD19 antibody or an antigen-binding fragment thereof, comprising the following:
(a) a heavy chain variable region comprising the following heavy chain complementarity determining region (CDR) amino acid sequences: CDRH1 of SEQ ID NO: 1 and CDRH2 of SEQ ID NO: 2; and
(b) a light chain variable region comprising the following light chain CDR amino acid sequence: CDRL1 of SEQ ID NO: 4.

2. The anti-CD19 antibody or the antigen-binding fragment thereof as set forth in claim 1, wherein the heavy chain variable region further comprises CDRH3 comprising any one of the amino acid sequences of SEQ ID NOS: 3 and 30 to 35.

3. The anti-CD19 antibody or the antigen-binding fragment thereof as set forth in claim 1, wherein the light chain variable region further comprises CDRL2 comprising any one of the amino acid sequences of SEQ ID NOS: 5 and 36 to 39.

4. The anti-CD19 antibody or the antigen-binding fragment thereof as set forth in claim 1, wherein the light chain variable region further comprises CDRL3 comprising any one of the amino acid sequences of SEQ ID NOS: 6, 40, and 41.

5. The anti-CD19 antibody or the antigen-binding fragment thereof as set forth in any one of claims 1 to 4, wherein the heavy chain variable region comprises any one of the sequences of SEQ ID NOS: 7, 42, 46, 50, 54, 58, 62, 66, and 70.

6. The anti-CD19 antibody or the antigen-binding fragment thereof as set forth in any one of claims 1 to 4, wherein the light chain variable region comprises any one of the amino acid sequences of SEQ ID NOS: 8, 43, 47, 51, 55, 59, 63, 67, and 71.

7. An anti-CD19 antibody or an antigen-binding fragment thereof, binding specifically to CD19 and shielding CD19 from being bound by an antibody or an antigen-binding fragment thereof which binds to at least one amino acid residue selected from the group consisting of T51, S53, E55, L58, K59, and K63 on the amino acid sequence of SEQ ID NO: 92.

8. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least two amino acid residues selected from the group consisting of T51, S53, E55, L58, K59, and K63 on the amino acid sequence of SEQ ID NO: 92.

9. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least three amino acid residues selected from the group consisting of T51, S53, E55, L58, K59, and K63 on the amino acid sequence of SEQ ID NO: 92.

10. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least one amino acid residue selected from the group consisting of L58, K59, and K63 on the amino acid sequence of SEQ ID NO: 92.

11. The anti-CD19 antibody or the antigen-binding fragment thereof as set forth in claim 7, wherein the anti-CD19 antibody or the antigen-binding fragment thereof binds specifically to CD19 and shields CD19 from being bound by an antibody or an antigen-binding fragment thereof which binds to at least two amino acid residues selected from the group consisting of L58, K59, and K63 on the amino acid sequence of SEQ ID NO: 92.

12. The anti-CD19 antibody or the antigen-binding fragment thereof as set forth in claim 7, wherein the anti-CD19 antibody or the antigen-binding fragment thereof specifically targets CD19 and binds to at least one amino acid residue selected from the group consisting of T51, S53, E55, L58, K59, and K63 on the amino acid sequence of SEQ ID NO: 92.

13. The anti-CD19 antibody or the antigen-binding fragment thereof as set forth in claim 7, wherein the anti-CD19 antibody or the antigen-binding fragment thereof specifically targets CD19 and binds to at least two amino acid residues selected from the group consisting of T51, S53, E55, L58, K59, and K63 on the amino acid sequence of SEQ ID NO: 92.

14. The anti-CD19 antibody or the antigen-binding fragment thereof as set forth in claim 7, wherein the anti-CD19 antibody or the antigen-binding fragment thereof specifically targets CD19 and binds to at least three amino acid residues selected from the group consisting of T51, S53, E55, L58, K59, and K63 on the amino acid sequence of SEQ ID NO: 92.

15. The anti-CD19 antibody or the antigen-binding fragment thereof as set forth in claim 7, wherein the anti-CD19 antibody or the antigen-binding fragment thereof specifically targets CD19 and binds to at least one amino acid residue selected from the group consisting of L58, K59, and K63 on the amino acid sequence of SEQ ID NO: 92.

16. The anti-CD19 antibody or the antigen-binding fragment thereof as set forth in claim 7, wherein the anti-CD19 antibody or the antigen-binding fragment thereof specifically targets CD19 and binds to at least two amino acid residues selected from the group consisting of L58, K59, and K63 on the amino acid sequence of SEQ ID NO: 92.

17. The anti-CD19 antibody or the antigen-binding fragment thereof as set forth in claim 7, being the antibody or the antigen-binding fragment according to any one of claims 1 to 6.

18. The anti-CD19 antibody or the antigen-binding fragment thereof as set forth in any one of claims 1 to 17, wherein the anti-CD19 antibody or the antigen-binding fragment thereof does not bind to an epitope to which FMC63 antibody binds.

19. The anti-CD19 antibody or the antigen-binding fragment thereof as set forth in claim 18, being a human antibody or a humanized antibody.

20. The anti-CD19 antibody or the antigen-binding fragment thereof as set forth in claim 18, being an scFv.

21. A nucleic acid molecule, encoding the anti-CD19 antibody or the antigen-binding fragment thereof according to any one of claims 1 to 20.

22. A recombinant vector, carrying the nucleic acid molecule of claim 21.

23. A host cell, transformed with the recombinant vector of claim 22.

24. A CD19-specific chimeric antigen receptor, comprising the following:
(a) an extracellular domain comprising the anti-CD19 antibody or the antigen-binding fragment thereof according to claim 1;
(b) a transmembrane domain; and
(c) an intracellular signaling domain.

25. The CD19-specific chimeric antigen receptor as set forth in claim 24, wherein the transmembrane domain is a transmembrane domain of a protein selected from the group consisting of alpha, beta, or zeta chain of T-cell receptor, CD27, CD28, CD3 epsilon, CD45, CD4, CD5, CD8(CD8α), CD9, CD16, CD22, CD33, CD37, CD64, CD80, CD86, CD134, CD137, and CD154.

26. The CD19-specific chimeric antigen receptor as set forth in claim 24, wherein the intracellular signaling domain is a CD3ζ (CD3 zeta) chain-derived domain.

27. The CD19-specific chimeric antigen receptor as set forth in claim 24, wherein the intracellular signaling domain further comprises a costimulatory molecule selected from the group consisting of OX40 (CD134), CD2, CD27, CD28, CD5, ICAM-1, LFA-1 (CD11a/CD18), and 4-1BB (CD137).

28. A cell, expressing the chimeric antigen receptor of any one of claims 24 to 27.

29. The cell as set forth in claim 28, being an immune cell selected from the group consisting of a dendritic cell, a killer dendritic cell, a mast cell, an NK-cell, a B-cell or an inflammatory T-lymphocyte, a cytotoxic T-lymphocyte, a regulatory T-lymphocyte, and a helper T-lymphocyte.

30. A pharmaceutical composition for prevention or treatment of a CD19 positive cell-associated disease, an autoimmune disease, or an inflammatory disease, the composition comprising the antibody or the antigen-binding fragment thereof according to any one of claims 1 to 20.

31. The pharmaceutical composition as set forth in claim 30, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

32. The pharmaceutical composition as set forth in claim 30, wherein the autoimmune disease or the inflammatory disease is selected from the group consisting of multiple sclerosis, rheumatoid arthritis, and systemic lupus erythematosus (SLE).

33. A pharmaceutical composition for prevention or treatment of a CD19 positive cell-associated disease, an autoimmune disease, or an inflammatory disease, the composition comprising the cell of claim 28 or 29.

34. The pharmaceutical composition as set forth in claim 33, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

35. The pharmaceutical composition as set forth in claim 33, wherein the autoimmune disease or the inflammatory disease is selected from the group consisting of multiple sclerosis, rheumatoid arthritis, and systemic lupus erythematosus (SLE).

36. A nucleic acid molecule, encoding the chimeric antigen receptor of claims 24 to 27.

37. A recombinant vector, carrying the nucleic acid molecule of claim 36.

38. A host cell, transformed with the recombinant vector of claim 37.

39. A method for treatment of a CD19 positive cell-associated disease, an autoimmune disease, or an inflammatory disease, the method comprising a step of administering the composition of any one of claims 30 to 35 to a subject in need thereof.

40. The method as set forth in claim 39, wherein the CD19 positive cell-associated disease is B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

41. The method as set forth in claim 39, wherein the autoimmune disease or an inflammatory disease is selected from multiple sclerosis, rheumatoid arthritis, and systemic lupus erythematosus (SLE).

42. The method as set forth in claim 39, wherein the subject is a mammal or a human.

According to an aspect thereof, the present disclosure provides an anti-CD19 antibody or an antigen-binding fragment thereof, comprising the following:

(a) a heavy chain variable region comprising the following heavy chain complementarity determining region (CDR) amino acid sequences: CDRH1 of SEQ ID NO: 1 and CDRH2 of SEQ ID NO: 2; and (b) a light chain variable region comprising the following light chain CDR amino acid sequence: CDRL1 of SEQ ID NO: 4.

In an embodiment of the present disclosure, the heavy chain variable region further comprises CDRH3 comprising any one of the amino acid sequences of SEQ ID NOS: 3 and 30 to 35.

In another embodiment of the present disclosure, the light chain variable region further comprises CDRL2 comprising any one of the amino acid sequences of SEQ ID NOS: 5 and 36 to 39.

In another embodiment of the present disclosure, the light chain variable region further comprises CDRL3 comprising any one of the amino acid sequences of SEQ ID NOS: 6, 40, and 41.

In another embodiment of the present disclosure, the heavy chain variable region comprises any one of the sequences of SEQ ID NOS: 7, 42, 46, 50, 54, 58, 62, 66, and 70.

In another embodiment of the present disclosure, the light chain variable region comprises any one of the amino acid sequences of SEQ ID NOS: 8, 43, 47, 51, 55, 59, 63, 67, and 71.

According to an aspect thereof, the present disclosure provides an anti-CD19 antibody or an antigen-binding fragment thereof which binds specifically to CD19 and shields CD19 from being bound by an antibody or an antigen-binding fragment thereof which binds to at least one amino acid residue selected from the group consisting of T51, S53, E55, L58, K59, and K63 on the amino acid sequence of SEQ ID NO: 92. The amino acid sequence of SEQ ID NO: 92 comes from human B lymphocyte antigen CD19 and is known as ID: P15391 in UniProtKB.

The antibody or the antigen-binding fragment of the present disclosure binds specifically to CD19 and shields CD19 from being bound by an antibody or an antigen-binding fragment thereof which binds to at least two amino acid residues selected from the group consisting of T51, S53, E55, L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least three amino acid residues selected from the group consisting of T51, S53, E55, L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least one amino acid residue selected from the group consisting of L58, K59, and K63 on the amino acid sequence of SEQ ID NO: 92.

The antibody or the antigen-binding fragment of the present disclosure binds specifically to CD19 and shields CD19 from being bound by an antibody or an antigen-binding fragment thereof which binds to at least two amino acid residues selected from the group consisting of L58, K59, and K63 on the amino acid sequence of SEQ ID NO:

In an embodiment of the present disclosure, the antibody or the antigen-binding fragment thereof specifically targets CD19 and binds to at least one amino acid residue selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least two amino acid residues selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least three amino acid residues selected from the group consisting of T51, S53, E55, L58, K59, and K63 on the amino acid sequence of SEQ ID NO: 92.

In another embodiment of the present disclosure, the antibody or the antigen-binding fragment thereof specifically targets CD19 and binds to at least one amino acid residue selected from the group consisting of L58, K59, and K63 on the amino acid sequence of SEQ ID NO: 92.

In another embodiment of the present disclosure, the antibody or the antigen-binding fragment thereof specifically targets CD19 and binds to at least two amino acid residues selected from the group consisting of L58, K59, and K63 on the amino acid sequence of SEQ ID NO: 92.

As confirmed in an example of the present disclosure, the anti-CD19 antibody of the present disclosure or an antigen-binding fragment thereof (e.g. CD19_12.18) exhibited decreased binding affinity for mtCD19(T51V), mtCD19(S53C), mtCD19(E55D), mtCD19(L58F), mtCD19(K59E), and mtCD19(K63N), which were modified from the hCD19 consisting of the amino acid sequence of SEQ ID NO: 92 at T51, S53, E55, L58, K59, and K63 residues, respectively. From the result, it was observed that the six amino acid residues function as important key residues responsible for the epitope site at which the anti-CD19 antibody or antigen-binding fragment of the present disclosure binds to CD19. Of them, the amino acid residues L58, K59, and K63 were found to be more important key residues responsible for the binding of the antibody or the antigen-binding fragment to CD19 as the binding affinity was significantly decreased for mutant hCD19 in which L58, K59, and K63 were modified. Therefore, the anti-CD19 antibody of the present disclosure or an antigen-binding fragment thereof binds to hCD19 including the amino acid sequence of SEQ ID NO: 92 at one, two, three or more amino acid residues selected from the group consisting of T51, S53, E55, L58, K59, and K63 on the sequence. In detail, the anti-CD19 antibody of the present disclosure or an antigen-binding fragment thereof binds to hCD19 including the amino acid sequence of SEQ ID NO: 92 at least one amino acid residue selected from the group consisting of L58, K59, and K63 on the sequence. As a result, the anti-CD19 antibody of the present disclosure or an antigen-binding fragment thereof shields CD19 from being bound by an antibody or an antibody-binding fragment thereof which binds to hCD19 including the amino acid sequence of SEQ ID NO: 92 at least one selected from the group consisting of T51, S53, E55, L58, K59, and K63 on the amino acid sequence. More particularly, the anti-CD19 antibody of the present disclosure or an antigen-binding fragment thereof shields CD19 from being bound by an antibody or an antigen-binding fragment thereof which binds to hCD19 including the amino acid sequence of SEQ ID NO: 92 at least one selected from the group consisting of L58, K59, and K63 on the amino acid sequence.

In an embodiment of the present disclosure, CD19_12.18 antibody or a variant thereof according to the present disclosure binds to CD19 at an epitope different from that of FMC63, which is an antibody used in a chimeric antigen receptor. The antibody of the present disclosure and variants thereof target the same epitope or compete with each other for binding to the same epitope in CD19.

As will be demonstrated in the Examples below, the anti-CD19 antibody or antigen-binding fragment of the present disclosure was greatly lowered in binding affinity for mtCD19(T51V), mtCD19(S53C), mtCD19(E55D), mtCD19(L58F), mtCD19(K59E), and mtCD19(K63N), which are hCD19 including the amino acid sequence of SEQ ID NO: 92 modified at amino acid residues T51, S53, E55, L58, K59, and K63, respectively. However, the binding affinity was maintained intact in FMC63 antibody. In addition, the antibody of the present disclosure or an antigen-binding fragment thereof normally binds to mtCD19 (H218R/KSS) whereas FMC63 antibody shows poor binding affinity for mtCD19(H218R/KSS). Therefore, the anti-CD19 antibody of the present disclosure or an antigen-binding fragment thereof does not bind to the epitope to which FMC63 antibody binds.

In another Example, an ELISA plate was coated with a the CD19_12.18 antibody variant (i.e., CD19_1218.81 antibody) of the present disclosure to which CD19-ECD-Ck alone or in combination with CD19_1218 antibody was added, followed by competitive ELISA. CD19_1218 antibody competed with CD19_1218.81 antibody for binding to CD19-ECD-Ck. As a result, a low level of CD19-ECD-Ck bound by CD19_1218 antibody was detected. Therefore, the anti-CD19 antibody and a variant thereof bind to the same epitope or compete with each other for the same epitope.

In the present disclosure, the antibody or antigen-binding fragment may be a human antibody or a humanized entity. In addition, the antibody or antigen-binding fragment of the present disclosure may be scFv, but is not limited thereto.

In the present disclosure, the antibody or the antigen-binding fragment was constructed by CDR grafting in which complementarity determining regions (CDRs) of conventional antibodies developed in mice into a framework more stable than those of the conventional antibodies. "CDR grafting" is a representative technique for humanizing a non-human antibody in order to solve the problem that murine monoclonal antibodies are neutralized due to the immunogenicity thereof upon use in human antibodies. That is, CDR grafting is to graft a CDR region of an animal antibody to the framework of human antibodies.

An antibody according to an aspect of the present disclosure is CD19_12.18 antibody or a variant thereof. In detail, the variant of CD19_12.18 antibody is hzCD_19_1218.81, hzCD_19_1218.82, hzCD_19_1218.81.12, hzCD_19_1218.81.17, hzCD_19_1218.81.52, hzCD_19_1218.81.55, hzCD_19_1218.81.64, or hzCD_19_1218.81.79. Amino acid sequences and nucleotide sequences of CDRs and light chain variable regions or heavy chain variable regions of the variants are given in the specification and the sequence listing appended.

In the specification, "FMC63" antibody is an example of murine anti-CD19 monoclonal antibodies (Nicholson et al., Molecular Immunology, 34(16-17): 1157-1165 (1997)).

Variable regions of FMC63 monoclonal antibody have been used in CAR tested in clinical trials (e.g., see [Kochenderfer et al., Nature Review Clinical Oncol., 10(5); 267-276 (2013); Porter et al., New Eng. J. Med., 365(8): 725-733 (2011); Kalos et al., Science Translational Medicine, 3(95): 95ra73 (2011); Kochenderfer et al., Blood, 116(20): 4099-4102 (2010); and Kochenderfer et al., Blood, 119(12): 2709-2720 (2012)]).

As used herein, the term "antibody" used in context of CD19 refers to an antibody specific for CD19 and is intended to encompass not only a whole antibody form, but also an antigen-binding fragment thereof.

A whole antibody includes two full length light chain and two full length heavy chains where each light chain is linked to the heavy chain by disulfide bonds. The heavy chain constant region is divided into isotypes of gamma (γ), mu (μ), alpha (α), delta (δ), and epsilon (ε) types, which are further subtyped into gamma1 (γ1), gamma2 (γ2), gamma3 (γ3), gamma4 (γ4), alpha 1 (α1), and alpha 2 (α2). The light chain constant region is divided into kappa (κ) and lambda (λ) types.

As used herein, the term "antigen-binding fragments" refers to a fragment retaining the function of binding to an antigen and includes Fab, F(ab'), F(ab')2, and Fv. Of them, Fab (fragment antigen binding) is composed of one constant and one variable domain of each of the heavy and the light chain, the constant domain of the heavy chain being the first constant domain (CH1), and thus contains one antigen-binding site. Fab' is different from Fab in that the former comprises a hinge region including at least one cysteine residue at the C-terminal of the CH1 domain of a heavy chain. F(ab')2 is produced by a disulfide bond formation between cysteine residues in the hinge region of Fab'. Fv is an antibody fragment composed only of variable regions of a heavy and a light chain, which may be produced by a recombinant technology disclosed in the art. In Fv (two-chain Fv), variable regions of a light and heavy chain are linked by a non-covalent bond, and in a single chain Fv, variable regions of a light and heavy chain are linked by a covalent bond through a peptide linker or it may form a dimer structure like a two chain FV through a direct linkage at the C-terminal. These antibody fragments can be obtained through a proteinase treatment (for example, a whole antibody may be treated with a papain to obtain Fab fragments or with pepsin to obtain F(ab')2 fragment) or preferably constructed using a recombinant DNA technology.

Herein, examples of the antibody include a monoclonal antibody, a multispecific antibody, a human antibody, a humanized antibody, a chimeric antibody, a single-chain Fv (scFv), a single-chain antibody, an Fab, an F(ab'), a disulfide-linked Fv (sdFv), an anti-idiotype (anti-Id) antibody, and an epitope-binding fragment thereof, but are not limited thereto.

The term "heavy chain", as used herein, refers to a full length chain comprising three constant regions CH1, CH2 and CH3 and one variable region VH comprising an amino acid sequence which is sufficient for conferring specificity to an antigen as well fragments thereof. Also The term "light chain" as used herein refers to a full length chain comprising one constant region CL and one variable region VL comprising an amino acid sequence which is sufficient for conferring specificity to an antigen as well fragments thereof.

The term "variable region" or "variable domain", as used herein, refers to a domain on a heavy or a light chain of an antibody, which is responsible for binding the antibody to an antigen. Variable domains on the heavy and the light chain of a native antibody (VH and VL, respectively) are generally similar in structure and each include four conserved framework regions (FRs) and three hypervariable regions (HVRs) (Kindt et al., Kuby Immunology, 6th edition, W.H. Freeman and Co., page 91 (2007)).

As used herein, the term "CDR" (complementarity determining region) refers to an amino acid sequence of the hypervariable regions on the immunoglobulin heavy and light chains (Kabat et al., Sequences of Proteins of Immunological Interest, 4th Ed., U.S. Department of Health and Human Services, National Institutes of Health (1987)). Three CDRs are included in each of the heavy chain (CDRH1, CDRH2, and CDRH3) and the light chain (CDRL1, CDRL2, and CDRL3). CDRs provides important contact residues with which the antibody binds to an antigen.

As used herein, the term "framework" or "FR" refers to variable domain residues other than hypervariable region (HVR) residues. The FR of the variable domain generally consists of four FR domains: FR1, FR2, FR3, and FR4. Thus, the HVR and FR sequences generally appear in the following sequence in VH:

FRH1 (framework region 1 of heavy chain)-CDRH1 (complementarity determining region 1 of heavy chain)-FRH2-CDRH2-FRH3-CDRH3-FRH4.

Also, HVR and FR sequences in VL (or Vk) are arranged in the order as follows: FRL1 (framework region 1 of light chain)-CDRL1 (complementarity determining region 1 of light chain)-FRL2-CDRL2-FRL3-CDRL3-FRL4.

By the term "specifically binding" or wordings relevant thereto, it is intended that an antibody or a constituent thereof, such as an antigen binding fragment or scFv, forms a complex with an antigen that is relatively stable under physiologic conditions. Specific binding can be characterized by an equilibrium dissociation constant of at least about $1 \times 10^{-6}$ M or less (e.g., less KD means more strong binding). Methods for determining whether two molecules specifically bind are well known in the art and include, for example, equilibrium dialysis, surface plasmon resonance, and the like.

The term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "human antibody", as used herein, refers to an antibody which possesses an amino acid sequence which corresponds to that of an antibody produced by a human or a human cell or derived from a non-human source that utilizes human antibody repertoires or other human antibody-encoding sequences.

The term "chimeric antibody" refers to an antibody in which a portion of the heavy and/or light chain is derived from a particular source or species, while the remainder of the heavy and/or light chain is derived from a different source or species.

In the context of specifically recognizing CD19, variants of the amino acid sequences listed in the sequence listing appended may fall within the scope of the anti-CD19 antibody or an antigen-binding fragment thereof according to the present disclosure. For example, a variation may be given to the amino acid sequence of an antibody in order to improve the binding affinity and/or other biological properties of the antibody. The variation includes a deletion, an addition, and/or a substitution of an amino acid residue on the amino acid sequence of the antibody.

Such amino acid variations may be provided on the basis of a relative similarity of amino acid side chains, e.g., hydrophobicity, hydrophilicity, charge, and size. As analyzed for size, shape, and type of amino acid side chains, it is clear that all of arginine, lysine and histidine residues are positively charged; alanine, glycine, and serine are similar in size; phenylalanine, tryptophan, and tyrosine have similar shapes. Accordingly, based on this consideration, arginine, lysine and histidine; alanine, glycine and serine; and phenylalanine, tryptophan and tyrosine may be considered to be biologically functional equivalents.

In making such variations, the hydropathic index of amino acids may be considered. Each amino acid has been assigned a hydropathic index on the basis of their hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. It is known that similar biological activity is retained only upon substitution of certain amino acids for other amino acids having a similar hydropathic index. In making variations based upon the hydropathic index, the substitution of amino acids whose hydropathic indices are within ±2 is preferred, those which are within ±1 are particularly preferred, and those within ±0.5 are even more particularly preferred.

It also is understood in the art that substitutions between amino acids having similar hydrophilicity values may result in the generation of proteins having biologically equivalent activities.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making variations based upon similar hydrophilicity values, the substitution of amino acids whose hydrophilicity values are within ±2 is preferred, those which are within ±1 are particularly preferred, and those within ±0.5 are even more particularly preferred.

The amino acid exchanges in proteins that do not substantially change the activity of the molecule are well known in the art (H. Neurath, R. L. Hill, The Proteins, Academic Press, New York, 1979). The most common exchanges are found between amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

According to an embodiment, the anti-CD19 antibody or the antigen-binding fragment of the present disclosure comprises: a heavy chain variable region containing at least one CDR including one amino acid sequence selected from SEQ ID NOS: 1 to 3 and SEQ ID NOS: 30 to 35; and a light chain variable region containing at least one CDR including one amino acid sequence selected from SEQ ID NOS: 4 to 6 and SEQ ID NOS: 36 to 41, and includes a monoclonal antibody, a multispecific antibody, a human antibody, a humanized antibody, a chimeric antibody, a single-chain Fv (scFv), a single-chain antibody, an Fab, an F(ab'), a disulfide-linked Fv (sdFv), an anti-idiotype (anti-Id) antibody, and an epitope-binding fragment thereof, but are not limited thereto.

In another embodiment, the anti-CD19 antibody or the antigen-binding fragment of the present disclosure comprises a heavy chain variable region including any one amino acid sequence of SEQ ID NOS: 7, 42, 46, 50, 54, 58, 62, 66, and 70.

In another embodiment, the anti-CD19 antibody or the antigen-binding fragment of the present disclosure comprises a light chain variable region including any one amino acid sequence of SEQ ID NOS: 8, 43, 47, 51, 55, 59, 63, 67, and 71.

In another embodiment, the anti-CD19 antibody or the antigen-binding fragment of the present disclosure is an anti-CD19 scFv.

In an exemplary embodiment of the present disclosure, the heavy chain variable region and the light chain variable region contained in the antibody or the antigen-binding fragment thereof are connected to each other via (Gly-Ser)n, (Gly$_2$-Ser)n, (Gly$_3$-Ser)n or (Gly$_4$-Ser)n linker, wherein n is an integer of 1 to 6 and particularly 3 to 4, but is not limited thereto. The light chain variable region and the heavy chain variable region in scFv may be, for example, arranged as follows: light chain variable region-linker-heavy chain variable; or heavy chain variable region-linker-light chain variable region.

Being of very poor similarity to CDR sequences of conventional anti-CD19 antibodies or chimeric antigen receptors including the same, the CDR sequence of the antibody of the present disclosure is unique. For example, a BLAST search performed for CD19_12.18 antibody of the present disclosure on the NCBI website detected an antibody disclosed in U.S. Pat. No. 9,074,002 (SEQ ID NO: 29) as the most homologous antibody, but with the CDR sequence homology therebetween being just 81.7%. Moreover, the antibody disclosed in U.S. Pat. No. 9,074,002 binds to protein tyrosine phosphatase 1B (PTP1B), which is different from the target of the antibody of the present disclosure.

According to another embodiment thereof, the present disclosure provides a nucleic acid molecule encoding the anti-CD19 antibody or the antigen-binding fragment thereof.

According to an embodiment of the present disclosure, the nucleic acid molecule encoding the anti-CD19 antibody or the antigen-binding fragment thereof comprises at least one CDR-encoding nucleotide sequence selected from the group consisting of the nucleotide sequences of SEQ ID NOS: 10 to 12 and at least one CDR-encoding nucleotide sequence selected from the group consisting of the nucleotide sequences of SEQ ID NOS: 13 to 15.

According to another embodiment of the present disclosure, the nucleic acid molecule comprises a heavy chain variable region-encoding nucleotide sequence including a nucleotide sequence selected from the group consisting of SEQ ID NOS: 16, 44, 48, 52, 56, 60, 64, 68, and 72.

According to another embodiment of the present disclosure, the nucleic acid molecule comprises a heavy chain variable region-encoding nucleotide sequence including a nucleotide sequence selected from the group consisting of SEQ ID NOS: 17, 45, 49, 53, 57, 61, 65, 69, and 73.

According to another embodiment of the present disclosure, the nucleic acid molecule comprises a nucleotide sequence encoding the antibody or the antigen-binding fragment having SEQ ID NO: 18, but is not limited thereto.

The term "nucleic acid molecule", as used herein, is intended to encompass DNA (gDNA and cDNA) and RNA molecules. Nucleotides are the basic building block of the nucleic acid molecule and include sugar or base-modified analogues as well as natural nucleotides (Scheit, *Nucleotide Analogs*, John Wiley, New York (1980); Uhlman and Peyman, *Chemical Reviews*, 90:543-584(1990)).

It should be understood to a person skilled in the art that the nucleotide sequence coding for the antibody, the antigen-biding fragment thereof, or the chimeric antigen receptor polypeptide according to the present disclosure is any nucleotide sequence that encode an amino acid sequence constituting the chimeric antigen receptor molecule and is not limited to particular nucleotide sequences.

The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., arginine or serine are six different codons), or codons containing biologically equivalent amino acids.

According to an embodiment of the present disclosure, nucleotide sequences of nucleic acids coding for polypeptides of heavy chain CDRs, light chain CDRs, heavy chain variable regions, light chain variable regions, heavy chains, or light chains in the antibody to CD19 or the antigen-binding fragment thereof according to the present disclosure are listed in the sequence listing appended.

The nucleic acid molecule of the present disclosure which encodes the anti-CD19 antibody or the antigen-binding fragment thereof is construed to encompass nucleotide sequences having substantial identity to the nucleic acid molecule. In this context, the term "substantial identity" refers to an identity of at least 80%, more preferably at least 90%, and most preferably at least 95% between the nucleotide sequence of the present disclosure and any other sequences as analyzed by commonly used algorithm when alignment therebetween is made as much correspondingly as possible.

Considering the above-described mutations having biologically equivalent activity, it should be construed that nucleic acid molecules encoding the antibody or the antigen-binding fragment; or the chimeric antigen receptor polypeptide according to the present disclosure also include sequences having substantial identity therewith. In this regard, the substantial identity refers to an identity of at least 61%, more preferably at least 70%, still more preferably 80%, and most preferably at least 90% between the nucleotide sequence of the present disclosure and any other sequences as analyzed by commonly used algorithm when alignment therebetween is made as much correspondingly as possible. Methods of alignment for sequence comparison are known in the art. Various methods and algorithms for alignment are disclosed in Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44 (1988); Higgins and Sharp, *CABIOS* 5:151-3(1989); Corpet et al., *Nuc. Acids Res.* 16:10881-90 (1988); Huang et al., *Comp. Appl. BioSci.* 8:155-65(1992) and Pearson et al., *Meth. Mol. Biol.* 24:307-31(1994). The NCBI Basic Local Alignment Search Tool (BLAST; Altschul, et al., *J. Mol. Biol.* 215:403-10(1990)) is available from, for example, the NBCI (National Center for Biological Information), and can be used in connection with sequence analysis programs, such as blastp, blasm, blastx, tblastn and tblastx, on the Internet. The use of the program in comparing sequence similarity can be available on the BLAST help page at the NCBI website.

Another aspect of the present disclosure provides a recombinant vector carrying a nucleic acid molecule coding for the anti-CD19 antibody or the antigen-binding fragment thereof.

According to another aspect thereof, the present disclosure provides a host cell transformed with the recombinant vector.

So long as it allows a vector to be cloned thereto and expressed sequentially, any host cell can be used in the present disclosure. Such host cells are well known in the art. For example, eukaryotic host cells suitable for the vector include monkey kidney cells (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

According to another aspect thereof, the present disclosure provides a CD19-specific chimeric antigen receptor comprising the following:
  (a) an extracellular domain containing the anti-CD19 antibody or the antigen-binding fragment thereof;
  (b) a transmembrane domain; and
  (c) an intracellular signaling domain.

As used herein, the term "chimeric antigen receptor (CAR)" refers to an artificially constructed hybrid protein or polypeptide in which an antigen-binding domain (e.g., single-chain variable fragment (scFv)) of an antibody is linked to a T-cell signaling or T-cell activating domain. Taking advantage of the antigen-binding function of a monoclonal antibody, chimeric antigen receptors give T cells the new ability to target a specific protein in a non-MHC-restricted manner. Non-MHC-restricted antigen recognition provides CAR-expressing T cells with an ability to recognize irrespective of antigen processing, thus avoiding main tumor escape mechanisms. In addition, when expressed in T cells, CAR does advantageously not dimerize with intrinsic T-cell receptor (TCR) alpha and beta chains.

The chimeric antigen receptor of the present disclosure comprises an extracellular domain containing an antibody induced against CD19, known as a B lymphocyte antigen, or against an antigen-binding fragment thereof. In the present disclosure, the antibody induced against CD19 or an antigen-binding fragment thereof is as defined above for the anti-CD19 antibody or the antigen-binding fragment thereof.

According to an embodiment of the present disclosure, the chimeric antigen receptor of the present disclosure is expressed on cell surfaces. Hence, the chimeric antigen receptor may comprise a transmembrane domain. The transmembrane domain may be derived from natural or synthetic sources known in the art. By way of example, the transmembrane domain may be a transmembrane domain of the protein selected from the group consisting of alpha, beta, or zeta chains of T-cell receptor, CD27, CD28, CD3 epsilon, CD45, CD4, CD5, CD8 (CD8a), CD9, CD16, CD22, CD33, CD37, CD64, CD80, CD86, CD134, CD137, and CD154, but is not limited thereto.

According to an exemplary embodiment of the present disclosure, the transmembrane domain is the CD8-derived hinge/transmembrane domain encoded by SEQ ID NO: 20.

The term "intracellular signaling domain", as used herein, refers to a functional protein domain that produces a $2^{nd}$ messenger or functions as an effector in response to the $2^{nd}$ messenger to intracellularly transfer information so as to regulate cellular activity via a defined signaling pathway.

According to another embodiment of the present disclosure, the chimeric antigen receptor of the present disclosure may comprise an intracellular signaling domain. The intracellular signaling domain is responsible for intracellular signaling following the binding of extracellular ligand binding domain to the target (e.g., CD19) resulting in the activation of the immune cell and immune response. In other words, the signal transducing domain is responsible for the activation of at least one of the normal effector functions of the immune cell in which the chimeric antigen receptor is expressed. For example, the effector function of a T cell can be a cytolytic activity or helper activity including the secretion of cytokines. Preferred examples of signal transducing domain for use in a chimeric antigen receptor can be the cytoplasmic sequences of the T cell receptor and co-receptors that act in concert to initiate signal transduction following antigen receptor engagement, as well as any derivate or variant of these sequences and any synthetic sequence that has the same functional capability.

According to an exemplary embodiment, the intracellular signaling domain of the chimeric antigen receptor is a domain derived from CD3 (CD3 zeta) chain.

According to a still further exemplary embodiment, the domain derived from the CD3 (CD3 zeta) chain is a CD3 domain encoded by a nucleotide sequence including SEQ ID NO: 22.

According to another exemplary embodiment of the present disclosure, the intracellular signaling domain of chimeric antigen receptor further comprises at least one costimulatory molecule selected from the group consisting of OX40 (CD134), CD2, CD27, CD28, CDS, ICAM-1, LFA-1 (CD11a/CD18), and 4-1BB (CD137). The intracellular signaling domain may be obtained or derived from an intracellular signaling molecule and may include an entirety or a part of the molecule from which the intracellular signaling domain is derived, as well as the domain described above.

According to an exemplary embodiment of the present disclosure, the costimulatory domain may be a functional signaling domain obtained from a protein selected from the group consisting of CD28, OX40, 4-1BB (CD137), and/or ICOS (CD278) and, more particularly, a functional signaling domain of CD28 and/or OX40.

According to another embodiment of the present disclosure, the intracellular signaling domain is a functional signaling of 4-1BB, CD28, OX40, CD3 zeta, or a combination thereof. Most particularly, the intracellular signaling domain is a functional signaling domain of CD3 zeta.

According to a more particular embodiment of the present disclosure, the costimulatory molecule including CD137 is a CD3 domain encoded by a nucleotide sequence including SEQ ID NO: 21.

The transmembrane domain and intracellular signaling domain in the chimeric antigen receptor of the present disclosure may be at least one combination selected from among the transmembrane domains and intracellular signaling domains described above. For example, the chimeric antigen receptor of the present disclosure may comprise the CD8a transmembrane domain and the intracellular signaling domains of CD28 and CD3.

Structures of CAR constructs according to an embodiment of the present disclosure are depicted in FIG. 9, with the amino acid/nucleotide sequences thereof given in the sequence listing appended.

Another aspect of the present disclosure provides a nucleic acid molecule encoding the chimeric antigen receptor described above.

The above-mentioned anti-CD19 antibody or the antigen-binding fragment (polypeptide) thereof, the nucleic acid molecule coding therefor, the chimeric antigen receptor comprising the anti-CD19 antibody or the antigen-binding fragment thereof, and the nucleic acid molecule coding for the chimeric antigen receptor are each in an isolated state.

As used herein, the term "isolated" means altered or removed from the natural/native state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

According to another aspect thereof, the present disclosure provides a recombinant vector carrying the above-mentioned nucleic acid molecule. For the "vector" to be described hereinafter, the antibody or the antigen-binding fragment thereof, or the nucleic acid molecule encoding a chimeric antigen receptor are commonly applied.

The term "vector" is intended to encompass a transfer vector and an expression vector.

As used herein, the term "transfer vector" refers to a composition of matter which comprises an isolated nucleic acid and which can be used to deliver the isolated nucleic acid into the interior of a cell. Examples of the transfer vector include, but are not limited to, linear polynucleotides, polynucleotides associated with ionic or amphiphilic compounds, plasmids, and viruses. More particularly, the transfer vector includes an autonomously replicating plasmid or virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector", as used herein, refers to a vector comprising a recombinant polynucleotide comprising expression control sequences operatively linked to a nucleotide sequence to be expressed in a host cell. An expression vector comprises sufficient cis-acting elements for expression; other elements for expression can be supplied by the host cell or in an in vitro expression system. Expression vectors include plasmids; cosmids; and viruses, such as bacteriophages, adenoviruses, lentiviruses, retroviruses, and adeno-associated viruses, which all incorporate the recombinant polynucleotide. According to an exemplary embodiment of the present disclosure, a nucleic acid molecule coding for the antibody or antigen-binding fragment, or the chimeric antigen receptor is operatively linked to a promoter in the vector of the present disclosure. As used herein, the term "operatively linked" means a functional linkage between a regulatory sequence for nucleic acid expression (example: a promoter, a signal sequence, or array of positions to which transcriptional factors bind) and other nucleic acid sequences, and by which the regulatory sequences are able to control the transcription and/or translation of the other nucleic acid sequence.

The recombinant vector system of the present disclosure can be constructed using various methods known in the art. With respect to concrete methods, reference may be made to Sambrook et al., Molecular Cloning, A Laboratory Manual, Cold Spring Harbor Laboratory Press (2001), which is incorporated herein by reference.

The vectors of the present disclosure may be constructed as a vector for gene cloning, for protein expression, or for gene transfer. Also, the vectors of the present disclosure may be constructed for eukaryotic or prokaryotic cells.

For example, when the present vector is an expression vector in a eukaryotic cell, promoters derived from genomes of mammalian cells (e.g., a metallothionein promoter, β-actin promoter, human hemoglobin promoter and human muscle creatinine promoter) or promoters derived from mammalian viruses (e.g., an adenovirus late promoter, a vaccinia virus 7.5K promoter, SV40 promoter, cytomegalovirus promoter, a tk promoter of HSV, a promoter of mouse mammary tumor virus (MMTV), a LTR promoter of HIV, a promoter of moloney virus, a promoter of Epstein Barr Virus (EBV), a promoter of Rous Sarcoma Virus (RSV)) may be use. Generally, the vectors include a polyadenylate sequence as a transcriptional termination sequence.

According to an embodiment of the present disclosure, when used as a transfer vector, the vector may be "retroviral vector". Retroviruses provide a convenient platform for gene delivery systems. A selected gene can be inserted into a vector and packaged in retroviral particles. The recombinant virus can then be delivered to cells of the subject either in vivo or in vitro. A number of retroviral systems are known in the art. In some exemplary embodiments, the retroviral vector may be a pMT retroviral vector, which is an MLV-based retroviral vector, but is not limited thereto.

According to an embodiment of the present disclosure, the vector may be a lentivirus vector or an adenovirus vector.

The recombinant vector of the present disclosure may be fused with additional nucleotide sequences to facilitate the isolation and purification of the polypeptide expressed from the vector. The nucleotide sequences to be fused with the present vector include, for example, glutathione S-transferase (Pharmacia, USA), maltose binding protein (NEB, USA), FLAG (IBI, USA) and 6×His (hexahistidine; Qiagen, USA) and the like. The expression vector of the present disclosure may also comprise a selectable marker gene and/or a reporter gene as a selection marker for evaluating the expression of the antibody or the antigen-binding fragment and the CAR polypeptide containing the antibody. The selectable marker gene may be an antibiotic resistant gene typically used in the art, examples of which include genes resistant to ampicillin, gentamicin, carbenicillin, chloramphenicol, streptomycin, kanamycin, geneticin, neomycin, and tetracycline. The reporter gene may be exemplified by luciferase, beta-galactosidase, chloramphenicol acetyl transferase, and green fluorescent protein genes.

Methods of introducing and expressing genes into a cell are known in the art. In the context of an expression vector, the vector can be readily introduced into a host cell, e.g., mammalian, bacterial, yeast, or insect cell by any method known in the art. For example, the expression vector can be transferred into a host cell by physical, chemical, or biological means. The physical means include calcium phosphate precipitation, lipofection, particle bombardment, microinjection, electroporation, and the like. The chemical means include colloidal dispersion systems, such as macromolecule complexes, nanocapsules, microspheres, beads, and lipid-based systems including oil-in-water emulsions, micelles, mixed micelles, and liposomes. Within the biological means are the use of DNA or RNA vectors such as lentivirus, retrovirus, and the like.

According to another aspect thereof, the present disclosure provides a cell expressing the chimeric antigen receptor.

In one embodiment of the present disclosure, the cell refers to a cell of hematopoietic origin functionally involved in the initiation and/or execution of an innate and/or adaptive immune response.

The immune cell according to the present disclosure may be derived from a stem cell. The stem cells may be adult stem cell, non-human embryonic stem cells, cord blood stem cells, bone marrow stem cells, induced pluripotent stem cells, or hematopoietic stem cells. More particularly, the immune cells may be selected from the group consisting of dendritic cells, killer dendritic cells, mast cells, NK-cells, B-cells or inflammatory T-lymphocytes, cytotoxic T-lymphocytes, regulatory T-lymphocytes, and helper T-lymphocytes, but are not limited thereto.

In the present disclosure, the chimeric antigen receptor-expressing cells are called effector cells. The effector cells include a population of autologous or allogeneic cells. In other words, the effector cells include a population of autologous or allogeneic cells expressing CAR specific for CD19.

According to an embodiment of the present disclosure, the effector cells include a population of cells transduced or transfected with a vector carrying a nucleic acid molecular coding for a CD19-specific CAR. The transfection or transduction can be achieved by various means known in the art as described above, without limitations.

Hence, according to an exemplary embodiment of the present disclosure, after being delivered into the effector cells, e.g., T lymphocytes or natural killer cells, the nucleic acid molecule coding for the CD19-specific CAR is transcribed into mRNA from which a CD19-specific CAR polypeptide is then translated, and expressed on the cell surface.

Also, another aspect of the present disclosure provides a pharmaceutical composition comprising a cell expressing the chimeric antigen receptor of the present disclosure.

The pharmaceutical composition may be provided in the form of a pharmaceutical composition comprising a chimeric antigen receptor-expressing cell and a pharmaceutically acceptable carrier.

When administered in the form of a pharmaceutical composition, the cell expressing the chimeric antigen receptor of the present disclosure may be a cell derived from an animal allogenic to the subject, or a cell autologous cell.

The pharmaceutical composition of the present disclosure comprises a population of cells expressing the chimeric antigen receptor of the present disclosure.

The pharmaceutical composition of the present disclosure comprises a cell expressing the chimeric antigen receptor of the present disclosure as an effective ingredient. Accordingly, the common descriptions between them are omitted in order to avoid undue redundancy leading to the complexity of this specification.

As will be proven in the following Example, when the chimeric antigen receptor T cells (CD19_12.18 CAR-T cells) containing the CD19_12.18 antibody fragment of the present disclosure and a CD19 antigen-expressing cell line (RaJi) are co-cultured, the CD19 antigen on the surface of the CD19-positve cell line (RaJi) is recognized to induce the activation of the chimeric antigen receptor. Thus, the pharmaceutical composition of the present disclosure is expected to find advantageous applications in the treatment of CD19 antigen-related diseases.

Diseases that can be prevented or treated by the pharmaceutical composition of the present disclosure are human and mammalian diseases associated with CD19 positive cells, including B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin's lymphoma.

In addition, the diseases include autoimmune diseases and inflammatory diseases associated with inappropriate or enhanced B cell count and/or activation. Examples of the autoimmune diseases and inflammatory diseases include multiple sclerosis, rheumatoid arthritis, and systemic lupus erythematosus (SLE).

The pharmaceutically acceptable carrier contained in the pharmaceutical composition of the present disclosure is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present disclosure may further comprise a lubricant, a wetting agent, a sweetening agent, a flavoring agent, an emulsifier, a suspending agent, a preservative, and the like in addition to the above ingredients. Suitable pharmaceutically acceptable carriers and preparations are described in detail in Remington's Pharmaceutical Sciences (19th ed., 1995).

The pharmaceutical composition of the present disclosure may be administered orally or parenterally, for example, by intravenous injection, subcutaneous injection, intramuscular injection, intraperitoneal injection, intrasternal injection, intratumoral injection, topical administration, intranasal administration, intrapulmonary administration, and rectal administration.

The appropriate dose of the pharmaceutical composition of the present disclosure varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, relief, or eradication of a disease condition.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. Here, the formulation may be in the form of a solution in an oily or aqueous medium, a suspension, an emulsion, an extract, a pulvis, a suppository, a powder, a granule, a tablet, or a capsule, and may further contain a dispersant or a stabilizer.

The pharmaceutical composition of the present disclosure may further comprise other pharmaceutically active agents or drugs, for example, chemotherapeutic agents such as asparaginase, busulfane, carboplatin, cisplatin, daunorubicin, doxorubicin, fluorouracil, gemcitabine, hydroxyurea, methotrexate, paclitaxel, rituximab, vinblastine, vincristine, and the like; targeted therapeutic agents such as bevacizumab, olaparib, and the like; or immune checkpoint inhibitors such as nivolumab, pembrolizumab, and the like, in addition to the above-described chimeric antigen receptor-expressing cells, or may be administered in combination therewith.

According to another aspect thereof, the present disclosure provides a method for treatment of a CD19 positive cell-associated disease, an autoimmune disease, or an inflammatory disease, the method comprising a step of administering to a subject in need thereof a composition comprising the antibody against CD19 or the antigen-binding fragment thereof; or a composition comprising an effector cell expressing the CD19-specific chimeric antigen receptor.

The CD19 positive cell-associated disease, the autoimmune disease, or the inflammatory disease, which are target diseases to be treated by the treated method, is as defined above for the target diseases of the pharmaceutical composition.

In an embodiment of the present invention, the subject is a mammalian animal or a human.

Since the method for the prevention or treatment of cancer or inflammatory disease according to the present disclosure employs the above-described antibody or antigen-binding fragment; or the chimeric antigen receptor-expressing effector cell as an effective ingredient, the overlapping descriptions thereof are omitted to avoid excessive complexity of the specification Advantageous Effects The antibody of the present disclosure binds specifically to CD19 that is highly expressed in cancer cells (particularly, blood cancer) and is very poor in CDR sequence homology to conventional CD19 target antibodies. Thus, the antibody of the present disclosure has a characteristic sequence which leads to specifically binding to an epitope different from that for conventional FMC63 antibody fragments. Inducing immune cell activation in response to stimulation with CD19-positive cells, the anti-CD19 antibody or the antigen-binding fragment of the present disclosure can be advantageously used as a CAR-immune cell therapy product.

BRIEF DESCRIPTION OF THE DRAWINGS

FIG. 9 is a view showing configurations of 7 constructs in which the chimeric antigen receptor components hinge region, transmembrane domain, and costimulatory domain were modified to optimize the activity of the developed antibody fragments.

MODE FOR CARRYING OUT THE INVENTION

Figure 1:
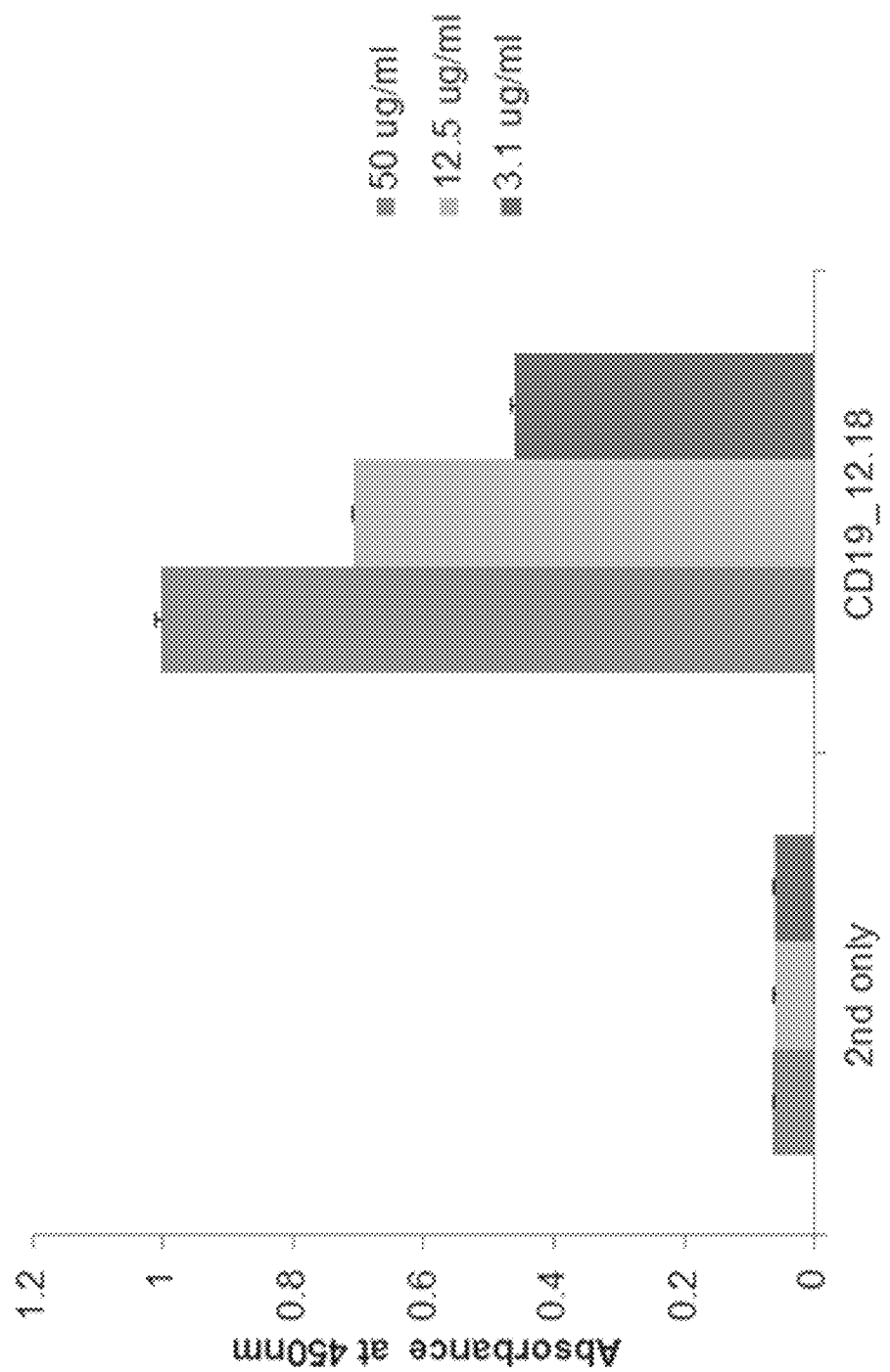
FIG. 1 is a graph illustrating the binding of CD19_12.18 antibody fragment to CD19-ECD protein as analyzed by ELISA.

A better understanding of the present disclosure may be obtained through the following examples which are set forth to illustrate, but are not to be construed as limiting the present disclosure.

EXAMPLES

Example 1: Development of Antibody to CD19

For antibody development, an extracellular domain (ECD) of human CD19 protein was produced using animal cells. A DNA construct in a form where the C-terminal of ECD was conjugated to the hinge and Fc region (CH2-CH3) of human IgG1 (CD19-ECD-Fc) or to His tag (CD19-ECD-His) was cloned into pCEP4 (Invitrogen, Cat. No. V044-50), using the restriction enzymes Hind-III and BamH-I. Subsequently, the transient transfection of the cloned vector into FreeStyle 293F cells (Invitrogen, Cat. No. R790-07) was conducted using polyethyleneimine (Polyscience Inc., Cat. No. 23966), followed by purification from the cell culture with the aid of protein-A Ceramic HyperD F resin (PALL, Cat No. 20078-028) or Ni-NTA Superflow (Qiagen, Cat No. 30410). The purified protein was quantitated using Protein assay dye (Bio-Rad, Cat. No. 500-0006) and subjected to SDS-PAGE, followed by coomassie blue staining to determine concentration and purity. The CD19-ECD-His protein thus obtained was subcutaneously injected to chickens. From the immunized chicken, the spleen and the bursa were excised. Total RNA was extracted from the spleen and the bursa, using TRI reagent (Invitrogen, USA), and used to synthesis cDNA therefrom. A library of antibody fragments was constructed using well-known primers specific for variable regions of immunoglobulin heavy and light chains (see Table 1, Phage display: a laboratory manual, Carlos Barbas III, et al., Cold Spring Harbor Laboratory Press).

TABLE 1

Primer Used for Construction of Antibody Fragment Library

| Primer | Sense | Antisense |
|---|---|---|
| Primer for heavy chain variable region | 5'GGTCAGTCCTCTAGATCTTCCGG CGGTGGTGGCAGCTCCGGTGGTGG CGGTTCCGCCGTGACGTTGGACGA G 3' (SEQ ID NO: 24) | 5'CTGGCCGGCCTGGCC ACTAGTGGAGGAGACG ATGACTTCGGTCC 3' (SEQ ID NO: 25) |
| Primer for light chain variable region | 5'GTGGCCCAGGCGGCCCTGACTCA GCCGTCCTCGGTGTC 3' (SEQ ID NO: 26) | 5'GGAAGATCTAGAGGA CTGACCTAGGACGGTC AGG 3' (SEQ ID NO: 27) |
| Overlapping PCR primer | 5'GAGGAGGAGGAGGAGGAGGTGG CCCAGGCGGCCCTGACTCAG 3' (SEQ ID NO: 28) | 5'GAGGAGGAGGAGGAG GAGGAGCTGGCCGGCC TGGCCACTAGTGGAGG 3' (SEQ ID NO: 29) |

The chicken immune library thus constructed was subjected to phage bio-panning, with the CD19-ECD-Fc serving as an antigen. For use in bio-panning, the antibody library was obtained in a phage library form using VCSM13 helper phages. Up to four panning rounds were performed. For a panning strategy of enriching phages of high affinity, a lower amount of the antigen was used and a larger number of washing was conducted in a higher number of panning. The number of phages captured by the target antigen was tittered using ER2537 $E.$ $coli$ (New England Biolabs, Cat. No. 801-N) as follows. Binder phages obtained in each bio-panning round were eluted with glycine buffer at pH 2.2. The ER2537 $E.$ $coli$ was cultured overnight in SB (super broth) medium and then diluted by 1/200 in fresh SB medium before passage. Subsequently, an additional incubation for 3 hours at 37° C. reached a log phage. In a 1.5-ml tube, 100 μl of fresh ER2537 $E.$ $coli$ and 10 μl of diluted phages were mixed and incubated for 30 min before being spread on ampicillin-containing LB (lysogeny broth) agar plates. After incubation overnight at 37° C., the number of phages was measured by applying the number of colonies thus formed and the dilution factor.

The binder phages obtained in each bio-panning round 2 were infected into ER2537 $E.$ $coli$. While the bacteria were maintained in the colony form, ELISA was performed to examine binding to the antigen. To this end, first, the colonies obtained following phage infection were inoculated into SB medium and cultured until the $OD_{600}$ reached 0.5. Subsequently, the cell culture was incubated at 30° C. in the presence of 0.5 mM IPTG while shaking so as to overexpress the antibody fragment proteins. Antibodies binding specifically to CD19 were selected by ELISA using CD19-ECD-Fc protein and by flow cytometry using Raji cells, which overexpress CD19. Through these methods, selection was made of CD19_12.18 that exhibited the highest binding affinity for human CD19. Amino acid sequences of the variable regions in the selected CD19_12.18 antibody are given in Table 2, below.

concentrations (50, 12.5, and 3.1 μg/mL) to CD19-ECD protein-coated plates. Following incubation with a secondary antibody (anti-human Fc HRP), color was developed with TMB. $OD_{450}$ values were read on an ELISA reader (Victor X3 PerkinElmer) (FIG. 1). As shown in FIG. 1, CD19_12.18 antibody of the present disclosure was identified to bind specifically to CD19-ECD protein.

Figure 2:
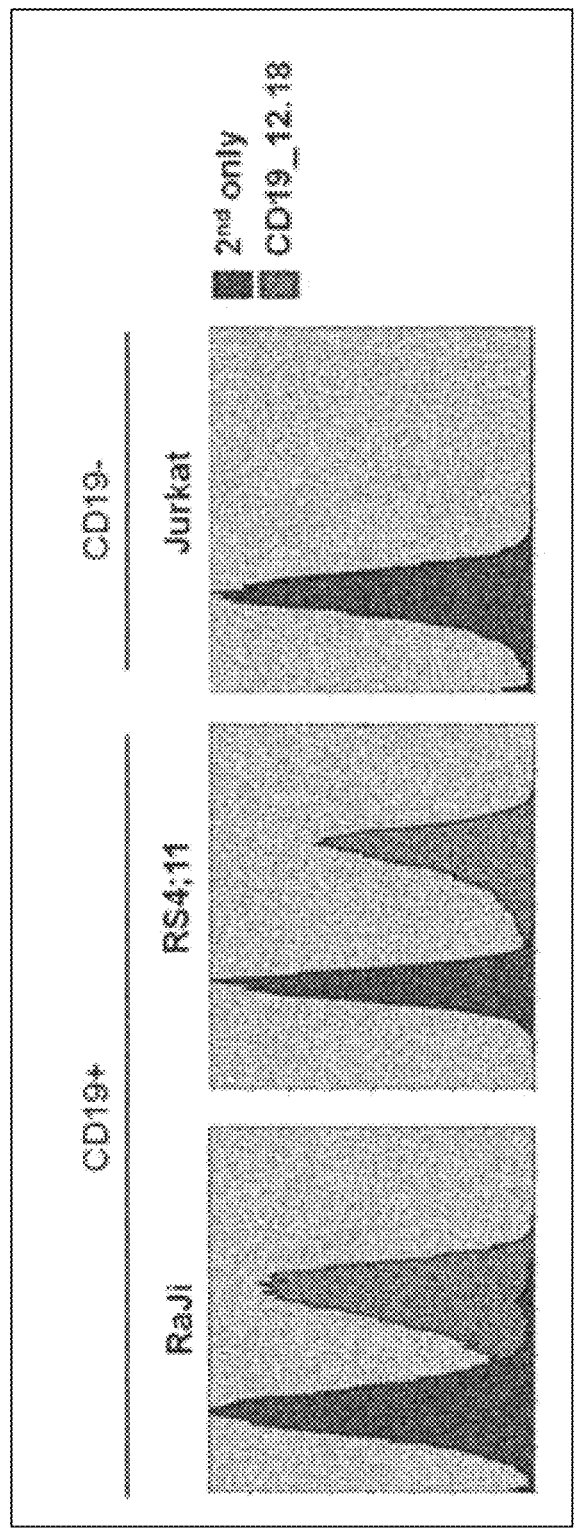
FIG. 2 shows histograms of binding affinity of CD19_12.18 antibody fragment for CD19-positve RaJi, RS4; 11 cells and CD19-negative Jurkat cells as measured by flow cytometry.

In addition, CD19_12.18, which binds to CD19-ECD protein was examined for affinity for the CD19 positive cell lines RaJi and RS4; 11 and the CD19 negative cell line Jurkat. The CD19 positive cell lines RaJi and RS4; 11 and the CD19 negative cell line Jurkat were treated with the purified antibody fragment (Anti-CD19 scFv-Fc). The antibody fragments bound to the cell lines were stained with anti-human IgG-FITC. Antibody fragments bound to the cell lines were measured by flow cytometry (FIG. 2). As can be seen in FIG. 2, CD19_12.18 antibody of the present disclosure was identified to be an antibody binding specifically to CD19 positive cells.

Example 2: Comparison of Epitopes Between Developed Antibody Fragment and FMC63

In order to examine whether the developed antibody has an epitope in common with FMC63, which is a mouse-derived CD19 antibody used in a chimeric antigen receptor (CAR) for treatment of B cell malignancy blood cancer, epitope binning was conducted using Octet system (Pall ForteBio). FMC63-Fc was fixed at a concentration of 10 μg/mL to AR2G sensor chip (Fortebio, Cat. No. 18-5092 (tray), 18-5093(pack), 18-5094(case)) by an amine coupling method using EDC/NHS. The CD19-ECD kappa light chain fusion (CD19-ECD-Ck) was conjugated at a concentration of 10 μg/mL for 10 min to the FMC63-fixed sensor chip, followed by stabilizing the linkage between FMC63 and CD19-ECD for 5 min. Thereafter, CD19_12.18 antibody of the present disclosure or FMC63 was conjugated at a

TABLE 2

Amino Acid Sequence of CDR (Complementarity Determining Region) in CD19_12.18 Antibody

| classification | light chain | heavy chain |
|---|---|---|
| CDR1 | SGGYSSYYG (SEQ ID NO: 4) | SYDMG (SEQ ID NO: 1) |
| CDR2 | ESNKRPS (SEQ ID NO: 5) | GIDDDGRYTSYGSAVDG (SEQ ID NO: 2) |
| CDR3 | GGWDSTHAGI (SEQ ID NO: 6) | GNAGWIDA (SEQ ID NO: 3) |

Figure 3:
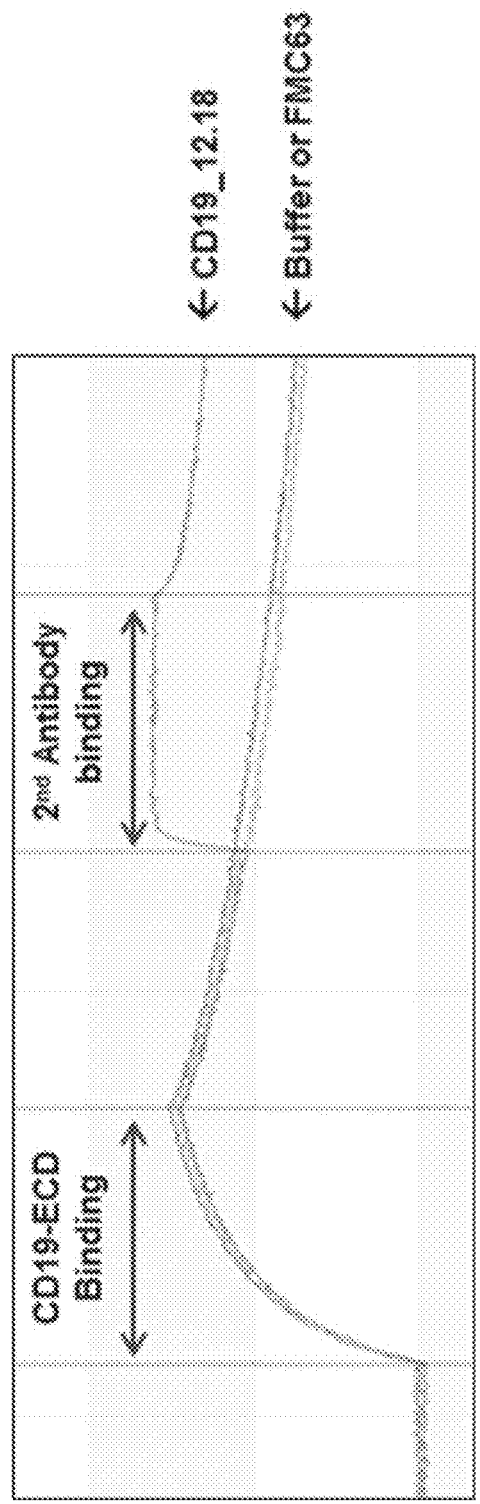
FIG. 3 is a view illustrating comparison of epitopes between the developed antibody fragment and the FMC63 antibody fragment. For epitope comparison with FMC63, FMC63 and CD19-ECD proteins are immobilized to a sensor chip to which the CD19_12.18 antibody fragment of the present disclosure is then applied.

In order to quantitatively analyze the affinity of the selected CD19_12.18 antibody, antibody fragments including the variable regions were produced using animal cells. A DNA construct in a form where the C-terminal of ECD was conjugated to the hinge and Fc region (CH2-CH3) of human IgG1 (CD19-ECD-Fc) or to His tag (CD19-ECD-His) was cloned into pCEP4 (Invitrogen, Cat. No. V044-50). Subsequently, the cloned vector was transiently transfected into FreeStyle™ 293F cells (Invitrogen, Cat. No. R790-07). From the cell culture, the antibody in the Fc fusion protein form (Anti-CD19 scFv-Fc) was obtained. ELISA was conducted using CD19-ECD kappa light chain fusion protein (CD19-ECD-Ck) as a coating antigen so as to measure the binding affinity of the selected antibody. The purified antibody fragment (Anti-CD19 scFv-Fc) was applied at various concentration of 10 μg/mL for 10 min, after which the linkage between the antigen and the antibody was stabilized for 10 min. Following fixation of FMC63, all the antibodies/antigen were diluted using kinetics buffer (Fortebio, cat No. 18-1092). The same buffer was also used for the stabilization step. In the case where the secondarily bound antibody further binds to the FMC63-bound CD19-ECD protein, the antibody can be construed to have no epitopes in common with FMC63. As shown in FIG. 3, FMC63 did not further bind whereas the CD19_12.18 antibody developed by the present inventors was observed to further bind to the FMC63-bound CD19-ECD. Therefore, CD19_12.18 antibody of the present disclosure is different from FMC63 antibody in terms of epitope.

Example 3: Identification of Epitope for the Developed Antibody

In order to identify epitopes therefor, the developed antibody was analyzed for binding to various mutant CD19 proteins constructed, using flow cytometry. In brief, first, the expression of CD19 protein was identified. To this end, the GFP protein-coexpressing bi-cistronic expression system (mutant CD19-T2A-GFP) using T2A system was digested with ClaI/XhoI and ligated to the pLenti6-V5/DEST lentiviral vector (Invitrogen, USA). The constructs thus obtained were analyzed by base sequencing. An examination was made of the binding of the antibody to the CD19 by flow cytometry for the 293 cell line which had undergone transient transfection to express the full-length CD19 protein and then treated with the purified antibody fragment (Anti-CD19 scFv-Fc).

Figure 4:
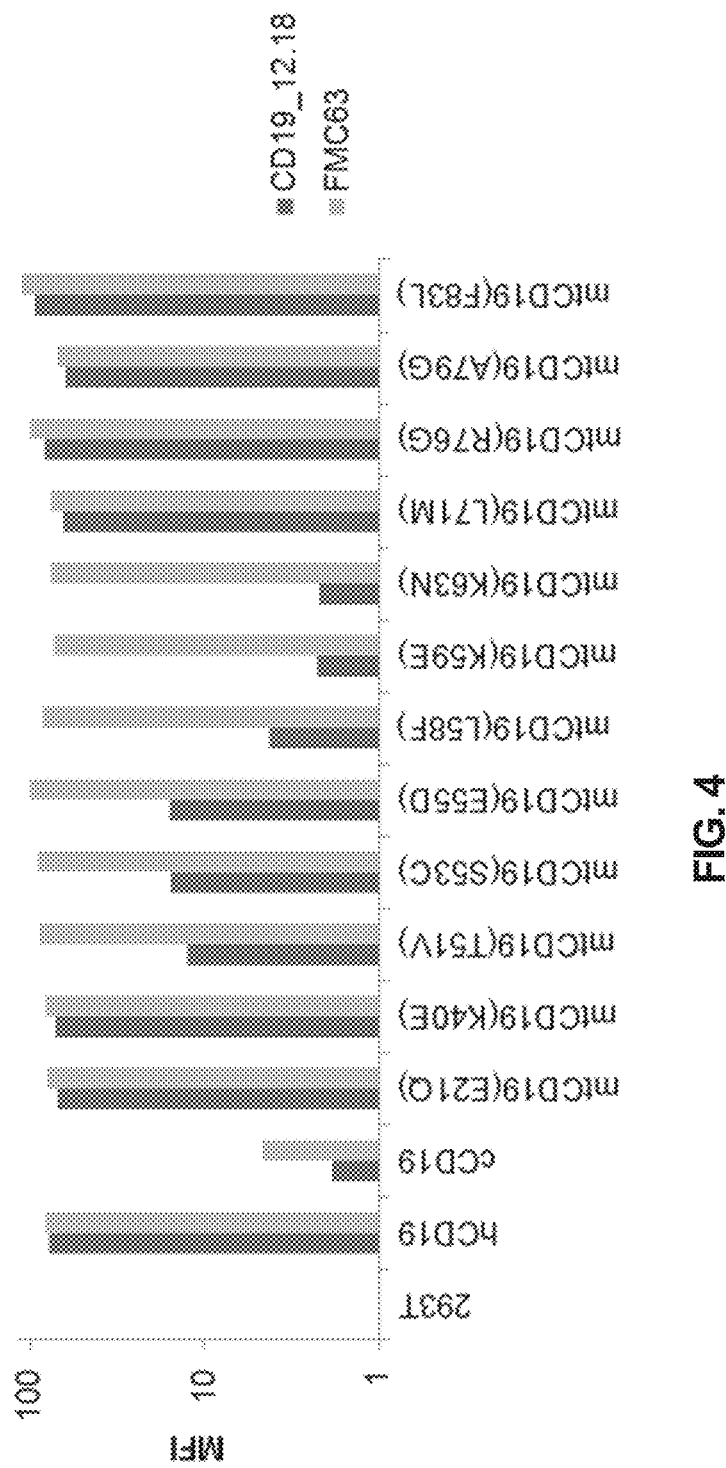
FIG. 4 is a bar graph showing the identification of an epitope for the developed antibody fragments as measured by flow cytometry. The developed antibody fragments were applied to 293 cells in which mutant CD19 had been expressed through transient transfection, with FMC64 antibody serving as a control.

To begin with, the developed antibody was measured for binding affinity for recombinant human CD19 (hCD19, UniProtKB: P15391, SEQ ID NO: 92) and cynomolgus monkey CD19 (cCD19, UniprotKB: G7Q0T7, SEQ ID NO: 93). Like FMC63, the developed antibody was observed to have no cross-reactivity with cCD19 cross-reactivity (FIG. 4). For use in investigating epitopes for the developed antibody, mutant CD19 (mtCD19) proteins were made by substituting amino acids at specific positions with corresponding amino acids in cynomolgus monkey CD19. With respect to 12 amino acid residues different between hCD19 and cCD19 in sites other than already reported epitope sites for FMC63, mutant CD19 proteins having the amino acid residues of cCD19 were developed, followed by analyzing binding affinity therefor. Binding to GFP-positive cells was analyzed on the basis of mean fluorescence intensity (MFI). Of the 12 mutants tested, six residues (T51V, S53C, E55D, L58F, K59E, and K63N) were observed to play an important role in binding between the developed antibody CD19_12.18 and hCD19. Inter alia, the three mutants (L58F, K59E, and K63N) were found to completely suppress the binding of CD19_12.18 to the CD19, revealing the residues as key residues essential for the epitope to which the developed antibody binds (FIG. 4). In contrast, FMC63 was observed to bind intactly to the six mutant hCD19 proteins, indicating that the mutations do not influence the overall structure of hCD19, but alter the epitopic sites to which CD19_12.18 bind.

Figure 5:
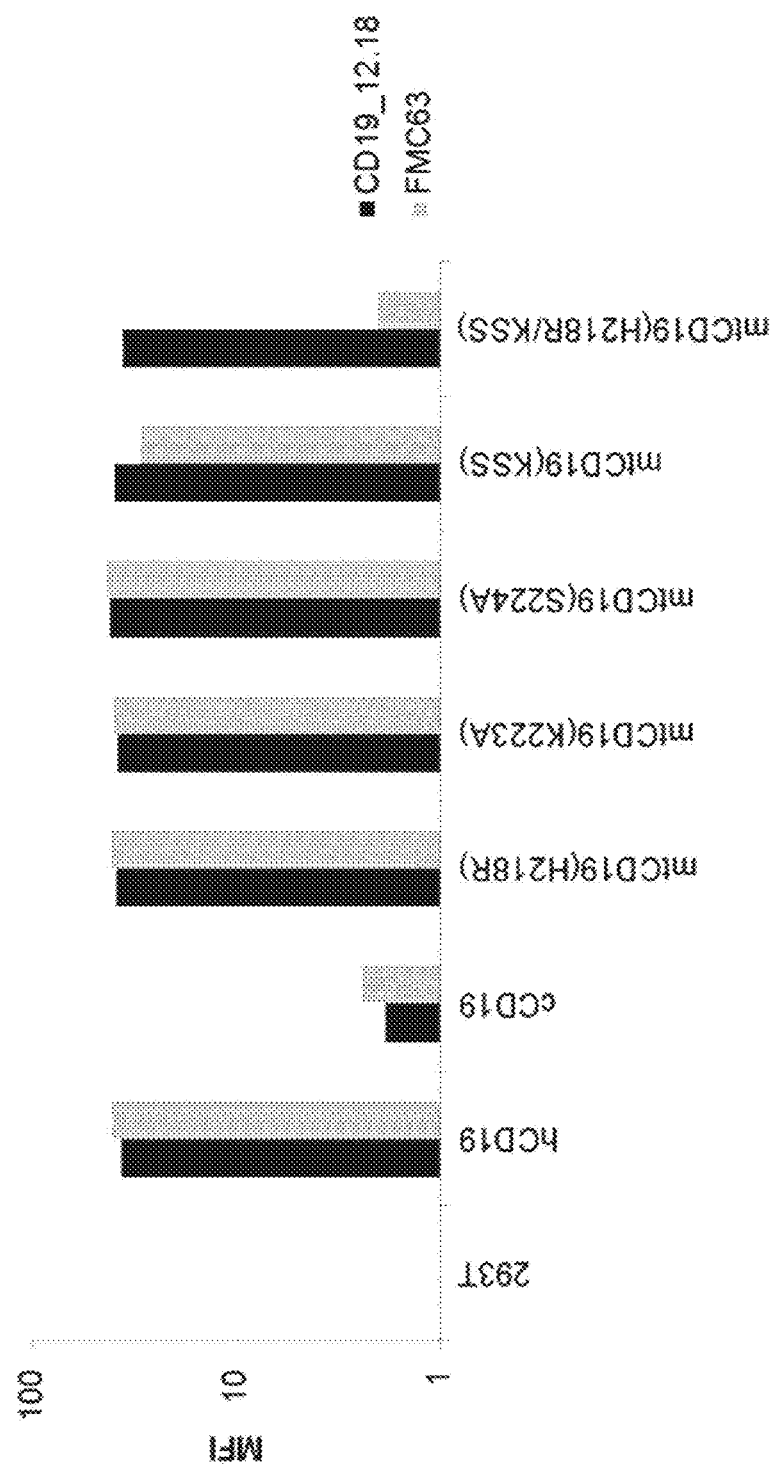
FIG. 5 is a bar graph identifying the binding of FMC63 and the developed antibody fragments to the epitope reported for FMC63. Epitope identification was conducted with 293 cells in which mutant CD19 had been expressed through transient transfection.

In addition, examination was made to see whether the antibody CD19_12.18 could bind to a mutant in which a site important for the binding of FMC63 thereto was mutated. In this regard, five mutants which had mutations made at sites important for the binding of FMC63 thereto were constructed (Sommermeyer D et al., Leukemia, 2017, 31(10): 2191). As was consistent with the result of the reference document, it was observed that FMC63 exhibited altered binding affinity for only the mutant (H218R/KSS) in which the residue at position 218 was substituted with arginine and serine was inserted at position 224. In contrast, the developed antibody CD19_12.18 was observed to normally bind to the mutant, indicating that the antibody is different in epitope from FMC63 (FIG. 5).

Example 4: Preparation of Lentivirus Including Developed Antibody Fragment-Conjugated Chimeric Antigen Receptor A chimeric antigen receptor was developed on the basis of the developed antibody CD19_12.18. For the chimeric antigen receptor, codon optimization was made of a CD8 leader, scFv-type CD19_12.18, a hinge and transmembrane domain of CD8, a cytoplasmic domain of CD137, and a cytoplasmic domain of CD3 zeta and the sequence thus optimized was digested with SpeI/XhoI before insertion into pLenti6-V5/DEST lentiviral vector (Invitrogen, USA). The construct thus obtained (SEQ ID NO: 23) was identified by base sequencing.

The prepared lentiviral construct was transduced, together with the plasmid pCMV-dR8.91 carrying viral coat protein VSV-G (vesicular stomatitis indiana virus G protein), gag, pol, and rev genes, into Lenti-X 293T cells (Takara Bio Inc., Japan). Transduction was performed using Lipofectamine 2000 (Invitrogen, USA) according to the manufacturer's protocol. Seventy-two hours after transduction, a lentivirus containing culture medium was enriched by 10 fold through a centrifugal filter (Millipore, USA).

Example 5: Preparation of T Cell Displaying Developed Antibody Fragment-Bearing Chimeric Antigen Receptor Cytotoxic T cells on which CD19_12.18 antibody fragment (scFv)-bearing chimeric antigen receptors were displayed were prepared using the lentivirus obtained in Example 3.

First, human naive T cells were isolated and stimulated with Dynabeads™ Human T-Activator CD3/CD28 (Thermofisher scientific, USA) for 24 hours. Thereafter, the lentivius was infected for 24 hours into the cells in the presence of polybrene (Sigma-Aldrich, USA). Then, the medium was exchanged with a medium containing IL-2 (Gibco, USA), followed by incubation at 37° C. in a 5% $CO_2$ atmosphere.

The T cells presenting the CD19_12.18-bearing chimeric antigen receptor on the surface thereof (CD19_12.18 CAR-T cells) were used in experiments within 24 hours after being prepared.

Example 6: Activity of Cytotoxic T Cell Presenting Developed Antibody Fragment-Bearing Chimeric Antigen Receptor on Surface Thereof The cytotoxic T cells presenting on the surface thereof the chimeric antigen receptor prepared in Example 4 (CD19_12.18 CAR-T cells) were used to examine whether the activation of the chimeric antigen receptor T cells is induced with the recognition of CD19 on cell surfaces.

Figure 6:
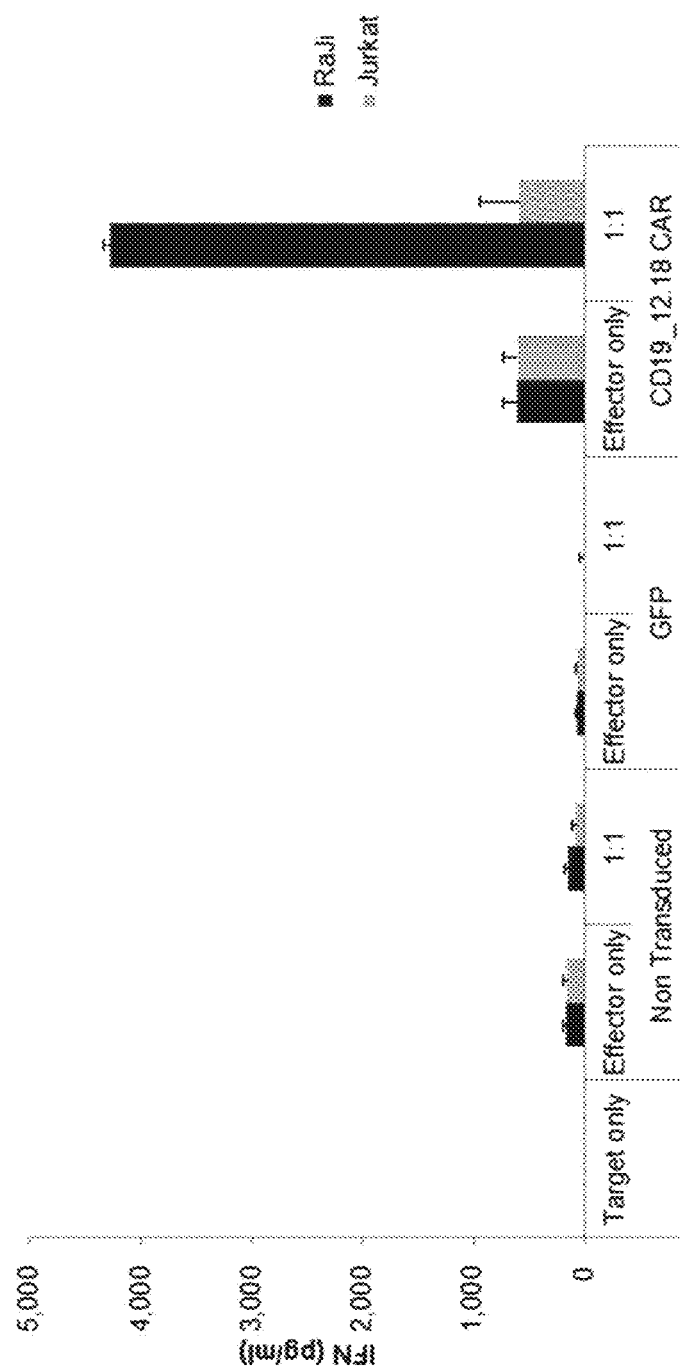
FIG. 6 is a bar graph showing activity of cytotoxic T cells expressing the chimeric antigen receptors conjugated with the antibody fragments of the present disclosure, as measured for secretion levels of interferon gamma.

Briefly, the CD19-positive cell line RaJi and the CD19-negative cell line Jurkat E6.1 were separately cultured in RPMI-1640 supplemented with 10% fetal bovine serum and 1% penicillin-streptomycin. First, the CD19-positive or negative cells were seeded at a density of $3 \times 10^4$ cells/well into round-bottom 96-well plates. After removal of the culture supernatant, the prepared chimeric antigen receptor T cells (CD19_12.18 CAR-T cells) were added at a predetermined rate per well and incubated at 37° C. for 24 hours in a 5% $CO_2$ atmosphere. Interferon gamma secreted to the medium was quantitated using an ELISA kit according to the manufacturer's protocol. The results are shown in FIG. 6. In this regard, a group in which chimeric antigen receptor T cells were added to plates containing target cells (Effector T cell only) and a group in which no chimeric antigen receptor T cells were added to plates containing target cells (Target cell only) were used as controls.

As can be seen in FIG. 6, significant increases in the secretion of interferon gamma were detected in the CD19_12.18 antibody fragment-bearing chimeric antigen receptor T cells of the present disclosure (CD19_12.18 CAR-T cells) and the CD19-positive cells (RaJi). Therefore, when recognizing CD19 on the CD19-positive cells (RaJi), the cytotoxic T cells (CD19_12.18 CAR-T cells) presenting the CD19_12.18 antibody fragment-bearing chimeric antigen receptor of the present disclosure on the surface thereof were induced to be activated.

Example 7: Improvement of Affinity of Developed Antibody Fragment and Development of Humanized Antibody In order to acquire antibody fragments superior to CD19_12.18 in terms of binding affinity for CD19, heavy chain and light chain libraries were combined to produce new sub libraries. To this end, oligonucleotides having NNK degenerate codons were employed, with 70% or more of the sequence of CD19_12.18 maintained. A nucleic acid sequence coding for the CD19_12.18 antibody fragment was used as a template DNA. Random codons were incorporated into six CDRs by PCR. The antibody fragment amplicons were purified using QIAquick Gel Extraction Kit (QIAGEN, USA). The antibody fragment amplicons were ligated to pComb3XSS vector after both were digested with sfi I. The resulting recombinant vector was transduced into ER2537 to construct phage libraries. Antibodies were selected using the phage libraries in the same manner as in Example 1.

From the selected antibodies, humanized antibodies were developed by CDR grafting. For the human antibody to which the CDR of the developed antibody would be implanted, human germ line V and J genes similar to each other in view of base sequence were selected using IMGT/V-QUEST (Brochet, X. et al., Nucl Acids Res. 36:503-508 (2008)). The developed humanized antibodies were produced in Fc tag forms, using FreeStyle™ 293F cells. IGHV3-74*01 and IGHJ5*01 were employed as V and J genes of the heavy chain, respectively. IGLV1-51*02 and IGLJ2*01 were employed as V and J genes of the light chain, respectively. Amino acid sequences of variable regions in heavy and light chains of the developed antibodies are given in Tables 3 and 4.

TABLE 3

Amino Acid Sequence of Heavy Chain CDR Region of Antibody with Improved Affinity

| Antibody | $1^{st}$ Heavy chain | $2^{nd}$ Heavy chain | $3^{Rd}$ Heavy chain |
| --- | --- | --- | --- |
| hzCD19_1218.81 | SYDMG (SEQ ID NO: 1) | GIDDDGRYTSYGSAVDG (SEQ ID NO: 2) | GNAGWIDA (SEQ ID NO: 3) |
| hzCD19_1218.82 | SYDMG (SEQ ID NO: 1) | GIDDDGRYTSYGSAVDG (SEQ ID NO: 2) | GNAGWIDA (SEQ ID NO: 3) |
| hzCD19_1218.81.12 | SYDMG (SEQ ID NO: 1) | GIDDDGRYTSYGSAVDG (SEQ ID NO: 2) | GNAGWIST (SEQ ID NO: 30) |
| hzCD19_1218.81.17 | SYDMG (SEQ ID NO: 1) | GIDDDGRYTSYGSAVDG (SEQ ID NO: 2) | GNAGWIET (SEQ ID NO: 31) |
| hzCD19_1218.81.52 | SYDMG (SEQ ID NO: 1) | GIDDDGRYTSYGSAVDG (SEQ ID NO: 2) | GNAGWILT (SEQ ID NO: 32) |
| hzCD19_1218.81.55 | SYDMG (SEQ ID NO: 1) | GIDDDGRYTSYGSAVDG (SEQ ID NO: 2) | GNAGWIQN (SEQ ID NO: 33) |
| hzCD19_1218.81.64 | SYDMG (SEQ ID NO: 1) | GIDDDGRYTSYGSAVDG (SEQ ID NO: 2) | GNAGWIQT (SEQ ID NO: 34) |
| hzCD19_1218.81.79 | SYDMG (SEQ ID NO: 1) | GIDDDGRYTSYGSAVDG (SEQ ID NO: 2) | GNAGWIDH (SEQ ID NO: 35) |

TABLE 4

Amino Acid Sequence of Light Chain CDR Region of Antibody with Improved Affinity

| Antibody | $1^{st}$ Light chain | $2^{nd}$ Light chain | $3^{rd}$ Light chain |
| --- | --- | --- | --- |
| hzCD19_1218.81 | SGGYSSYYG (SEQ ID NO: 4) | ESNKRPS (SEQ ID NO: 5) | GGLTPTHAGI (SEQ ID NO: 40) |

TABLE 4-continued

Amino Acid Sequence of Light Chain CDR Region of Antibody with Improved Affinity

| Antibody | 1st Light chain | 2nd Light chain | 3rd Light chain |
| --- | --- | --- | --- |
| hzCD19_1218.82 | SGGYSSYYG (SEQ ID NO: 4) | ESNKRPS (SEQ ID NO: 5) | GQSTRTHAGI (SEQ ID NO: 41) |
| hzCD19_1218.81.12 | SGGYSSYYG (SEQ ID NO: 4) | ESDKRPA (SEQ ID NO: 36) | GGLTPTHAGI (SEQ ID NO: 40) |
| hzCD19_1218.81.17 | SGGYSSYYG (SEQ ID NO: 4) | ESNKRPS (SEQ ID NO: 5) | GGLTPTHAGI (SEQ ID NO: 40) |
| hzCD19_1218.81.52 | SGGYSSYYG (SEQ ID NO: 4) | ETDKRPQ (SEQ ID NO: 37) | GGLTPTHAGI (SEQ ID NO: 40) |
| hzCD19_1218.81.55 | SGGYSSYYG (SEQ ID NO: 4) | ESGKRPA (SEQ ID NO: 38) | GGLTPTHAGI (SEQ ID NO: 40) |
| hzCD19_1218.81.64 | SGGYSSYYG (SEQ ID NO: 4) | ESQKRPL (SEQ ID NO: 39) | GGLTPTHAGI (SEQ ID NO: 40) |
| hzCD19_1218.81.79 | SGGYSSYYG (SEQ ID NO: 4) | ESNKRPS (SEQ ID NO: 5) | GGLTPTHAGI (SEQ ID NO: 40) |

Figure 7:
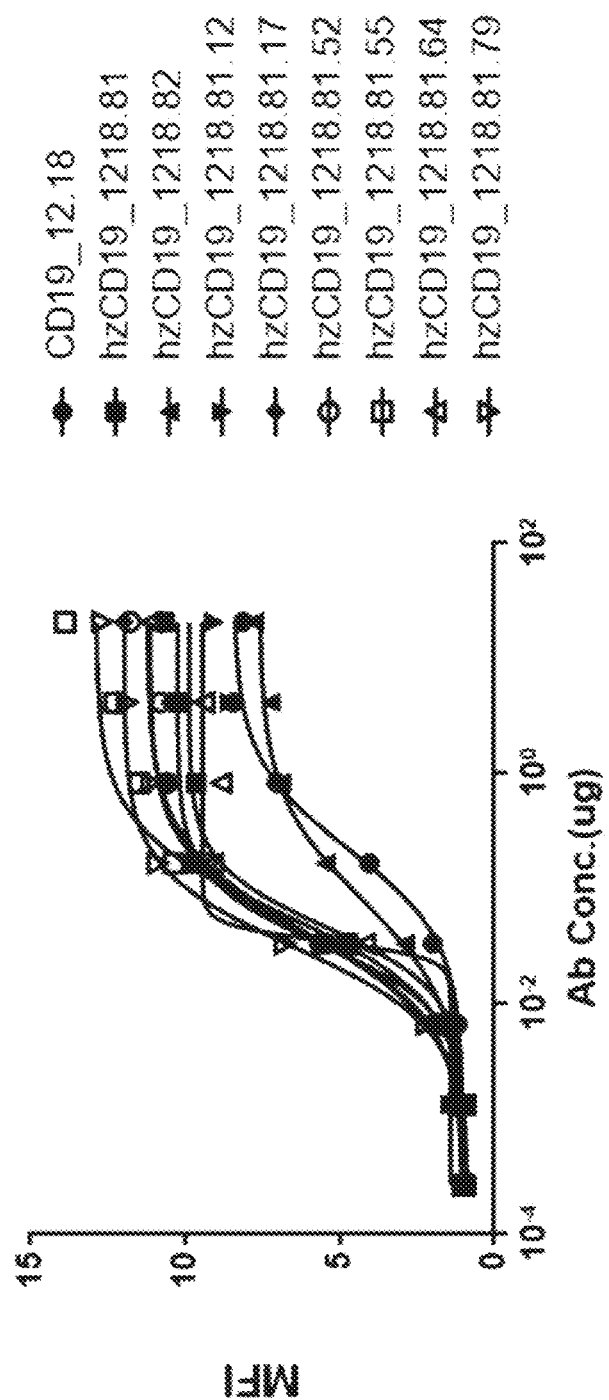
FIG. 7 is a plot showing cell binding potentials of antibody fragments developed through affinity improvement and humanization. CD19-positive RaJi cells were used for the analysis [unit: MFI (mean fluorescence intensity)].

Following affinity improvement and humanization, the selected antibodies were assayed for binding affinity for the CD19-positive cell line RaJi. The CD19-positive cell line RaJi was incubated with various concentrations of purified antibody fragments, followed by staining with anti-human IgG-FITC. The antibody-bound RaJi cells were counted by flow cytometry (FIG. 7) and binding affinity was assayed by Graphpad Prism (Table 5). Through the assay, antibodies having higher binding potential than CD19_12.18 were secured.

TABLE 5

Binding Potential of Affinity-Improved Antibody to RaJi Cell ($EC_{50}$)

| Antibody | $EC_{50}$ (μg) |
| --- | --- |
| CD19_12.18 | 0.213 |
| hzCD19_1218.81 | 0.032 |
| hzCD19_1218.82 | 0.078 |
| hzCD19_1218.81.12 | 0.034 |
| hzCD19_1218.81.17 | 0.038 |
| hzCD19_1218.81.52 | 0.038 |
| hzCD19_1218.81.55 | 0.059 |
| hzCD19_1218.81.64 | 0.033 |
| hzCD19_1218.81.79 | 0.030 |

Example 8: Preparation of Lentivirus Comprising Chimeric Antigen Receptor Conjugated with Affinity-Improved and Humanized Antibody Fragment Of the developed antibodies, three variants (hzCD19_1218.81, hzCD19_1218.82, and hzCD19_1218.81.79) different in affinity were used to develop chimeric antigen receptors. For a chimeric antigen receptor, codon optimization was made of a CD8 leader, an scFv-type antibody, a hinge and transmembrane domain of CD8, a cytoplasmic domain of CD137, and a cytoplasmic domain of CD3 zeta by using GeneOptimizer (Invitrogen) algorithm. The optimized sequences were digested with SpeI/PacI and ligated to pLenti6.3/V5-TOPO lentiviral vector (Invitrogen, USA) in which the promotor had been modified into EF-1 alpha. The constructs thus obtained were identified by base sequencing.

Each of the prepared lentiviral constructs was transduced, together with the plasmid pCMV-dR8.91 carrying viral coat protein VSV-G (vesicular stomatitis indiana virus G protein), gag, pol, and rev genes, into Lenti-X 293T cells (Takara Bio Inc., Japan). Transduction was performed using Lipofectamine 2000 (Invitrogen, USA) according to the manufacturer's protocol. The cell culture containing lentivirus were enriched with Lenti-X concentrator (Takara Bio Inc., Japan) and stored.

Example 9: Preparation and Activity of Cytotoxic T Cell Presenting on Surface Thereof Chimeric Antigen Receptor Conjugated with Affinity-Improved and Humanized Antibody Fragment Cytotoxic T cells presenting the CD19_12.18 antibody fragment (scFv)-bearing chimeric antigen receptor on the surface thereof were prepared using the lentivirus obtained in Example 8 in the same manner as in Example 5. The cytotoxic T cells presenting the chimeric antigen receptor on the surface thereof were used to examine whether the activation of the chimeric antigen receptor T cells is induced with the recognition of CD19 on cell surfaces.

Briefly, GFP-luciferase-expressing lentivirus was transduced into CD19-positive RaJi cells to construct RaJi-Luc cells which were then used in experiments. First, RaJi-Luc cells were seeded at a density of 3×10⁴ cells/well into round-bottom 96-well plates. To the RaJi-Luc cells (T)-seeded plates, the prepared cytotoxic T cells (E) were added at a predetermined treatment rate per well (T:E=1:2, 1:5, or 1:10), followed by incubation at 37° C. for 24 hours in a 5% $CO_2$ atmosphere. Thereafter, interferon gamma secreted to the medium was quantitated using an ELISA kit according to the manufacturer's protocol. Toxicity of cytotoxic T cells was identified through luciferase measurement (Bio-Glo Luciferase assay system, Promega, USA).

Figure 8A:
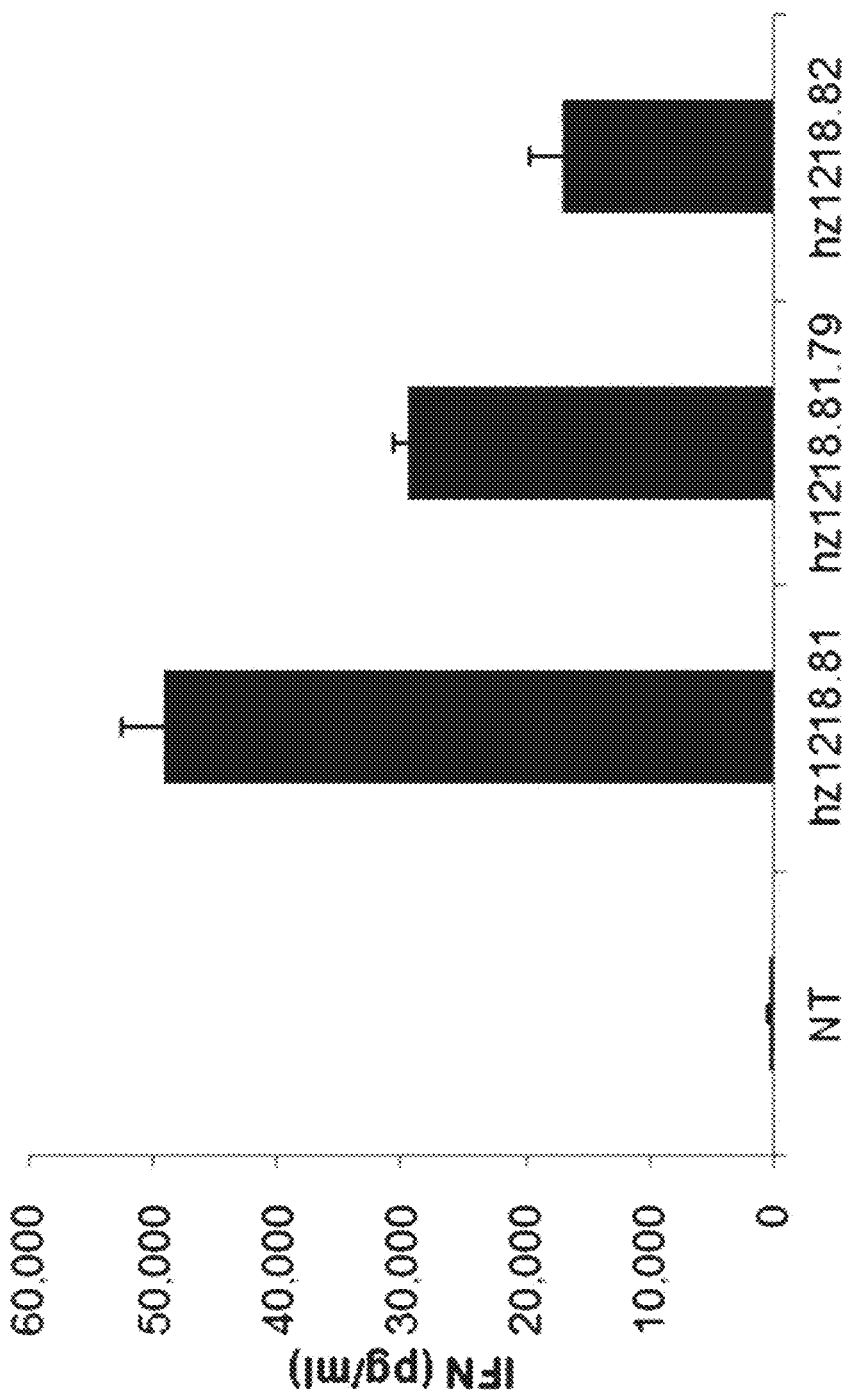
FIG. 8a is a bar graph showing activity of cytotoxic T cells expressing the chimeric antigen receptors conjugated with the antibody fragments of the present disclosure, as measured for secretion levels of interferon gamma. CD19-positive RaJi-Luc cells and cytotoxic T cells were co-cultured at a ratio of 1:5, followed by measuring levels of interferon gamma in the cell cultures.
Figure 8B:
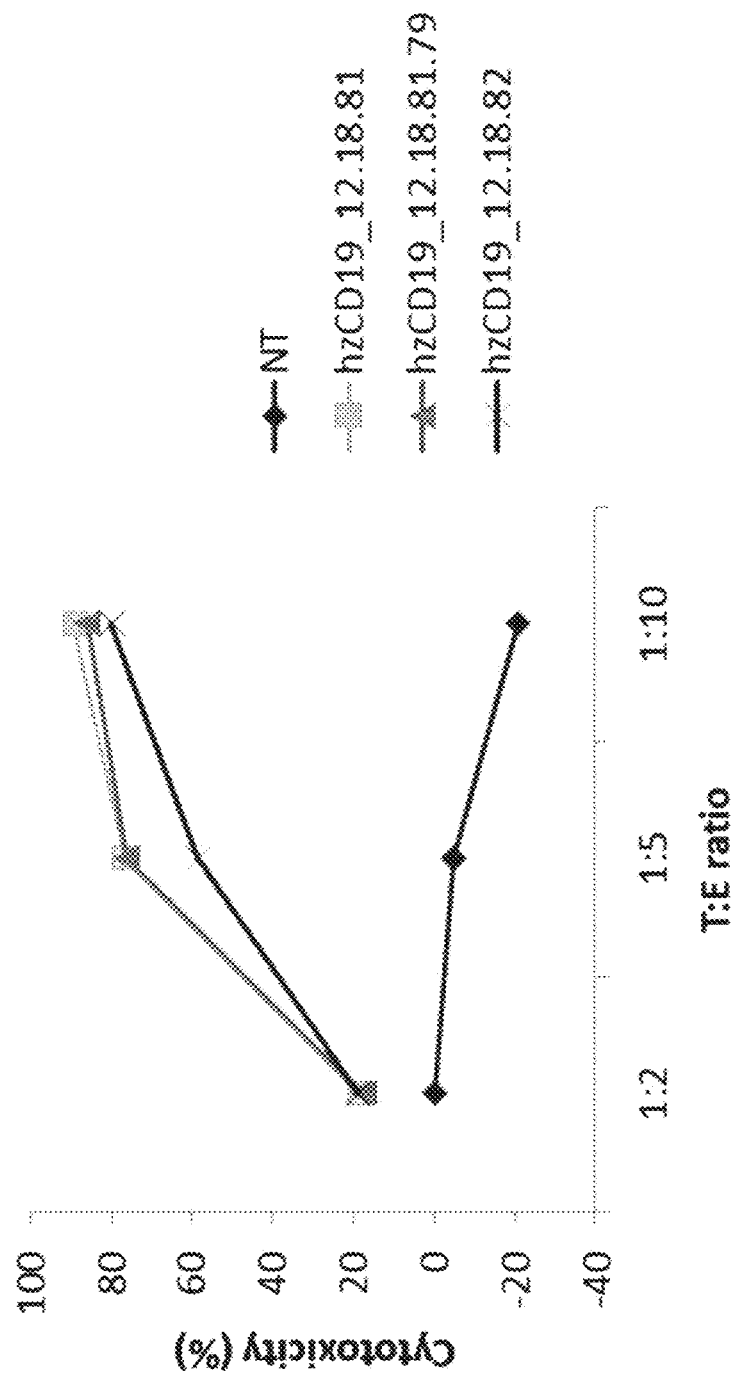
FIG. 8b shows cytotoxicity of cytotoxic T cells as measured for luciferase activity of RaJi-Luc cells surviving after co-culture with RaJi-Luc cells and cytotoxic T cells were co-cultured.
Figure 10A:
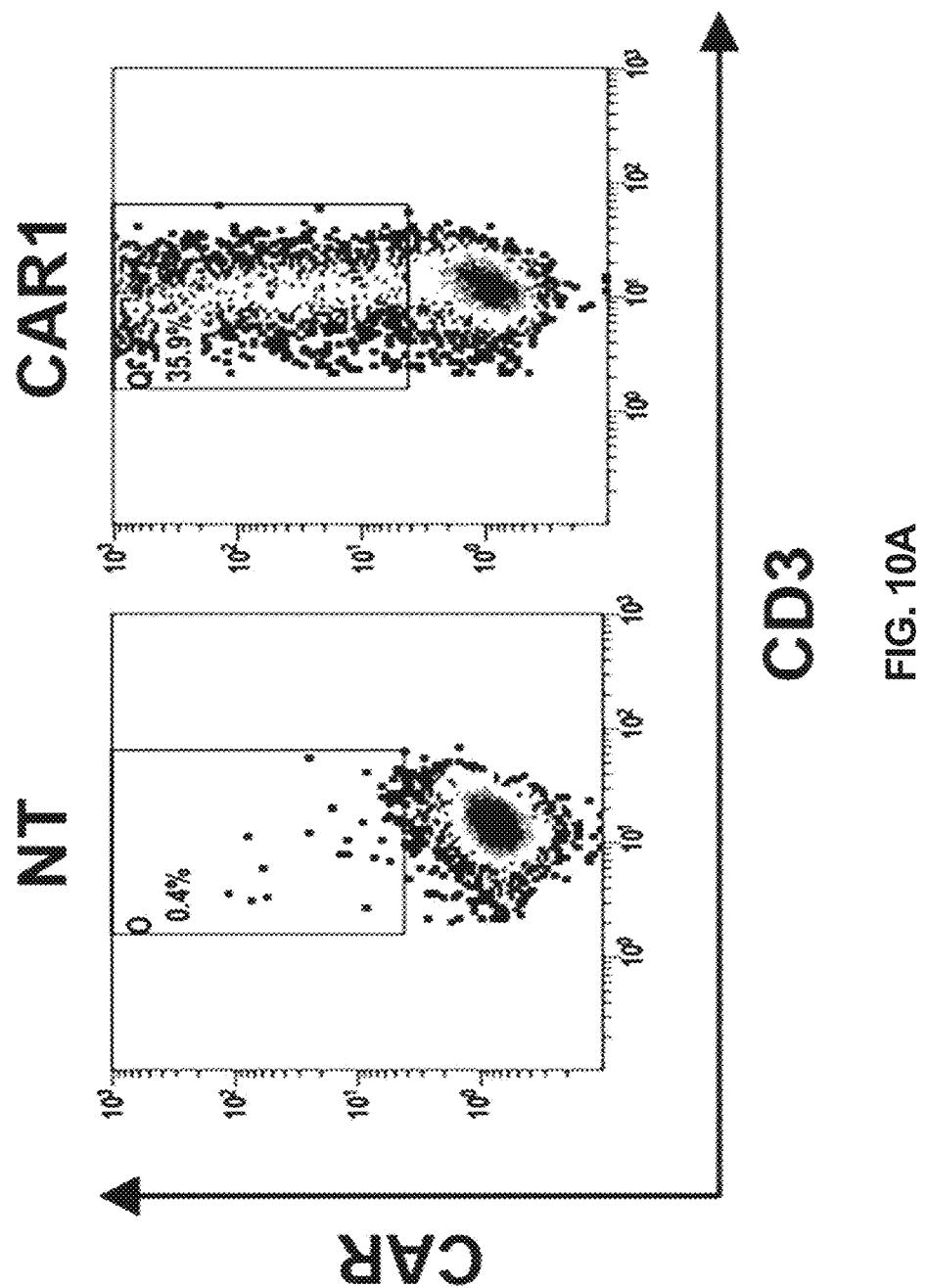
FIG. 10 showing expression of the 7 modified chimeric antigen receptors as analyzed by flow cytometry. CD3 was used as a marker for analyzing the expression of the 7 modified chimeric antigen receptors in cytotoxic T cells.
Figure 10B:
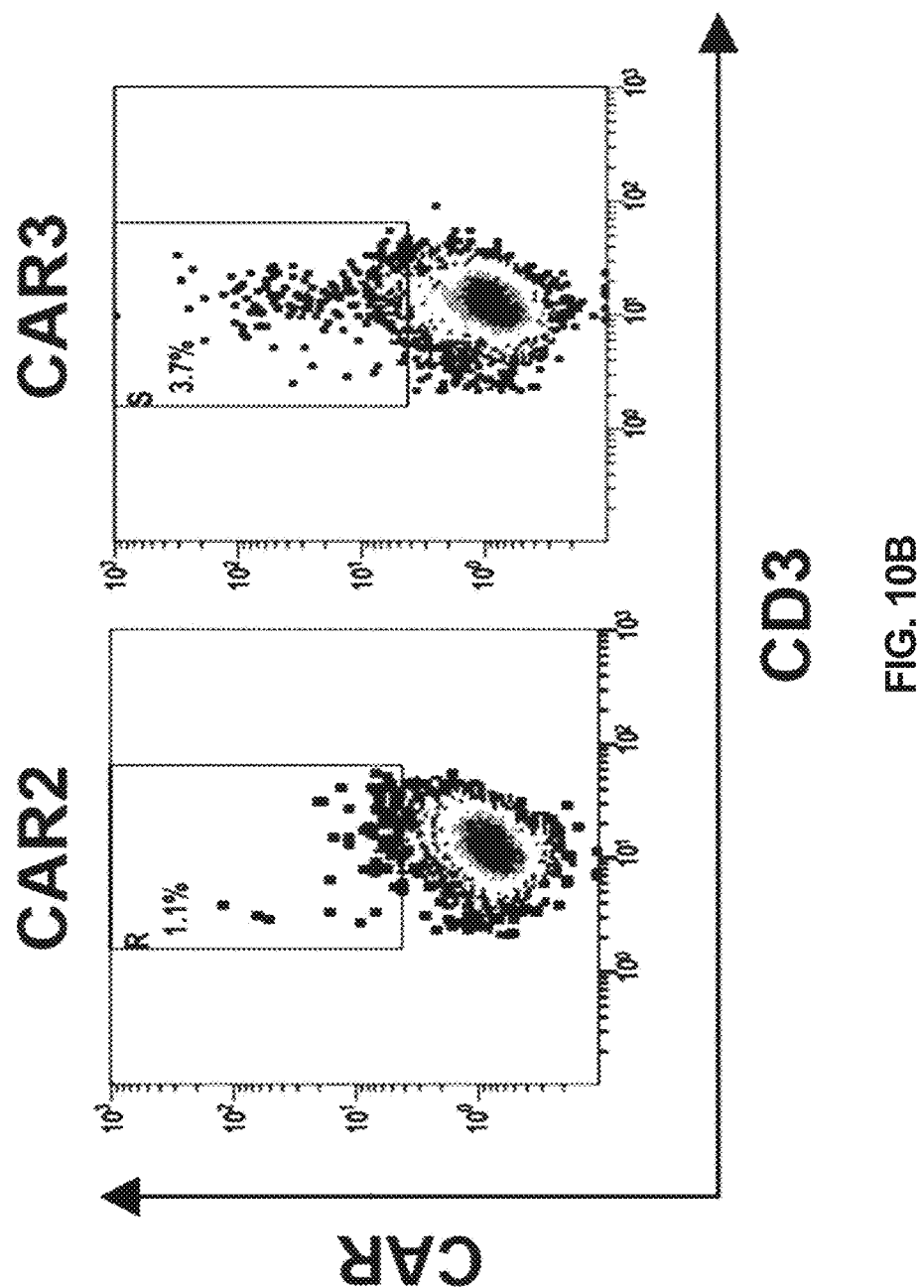
Figure 10C:
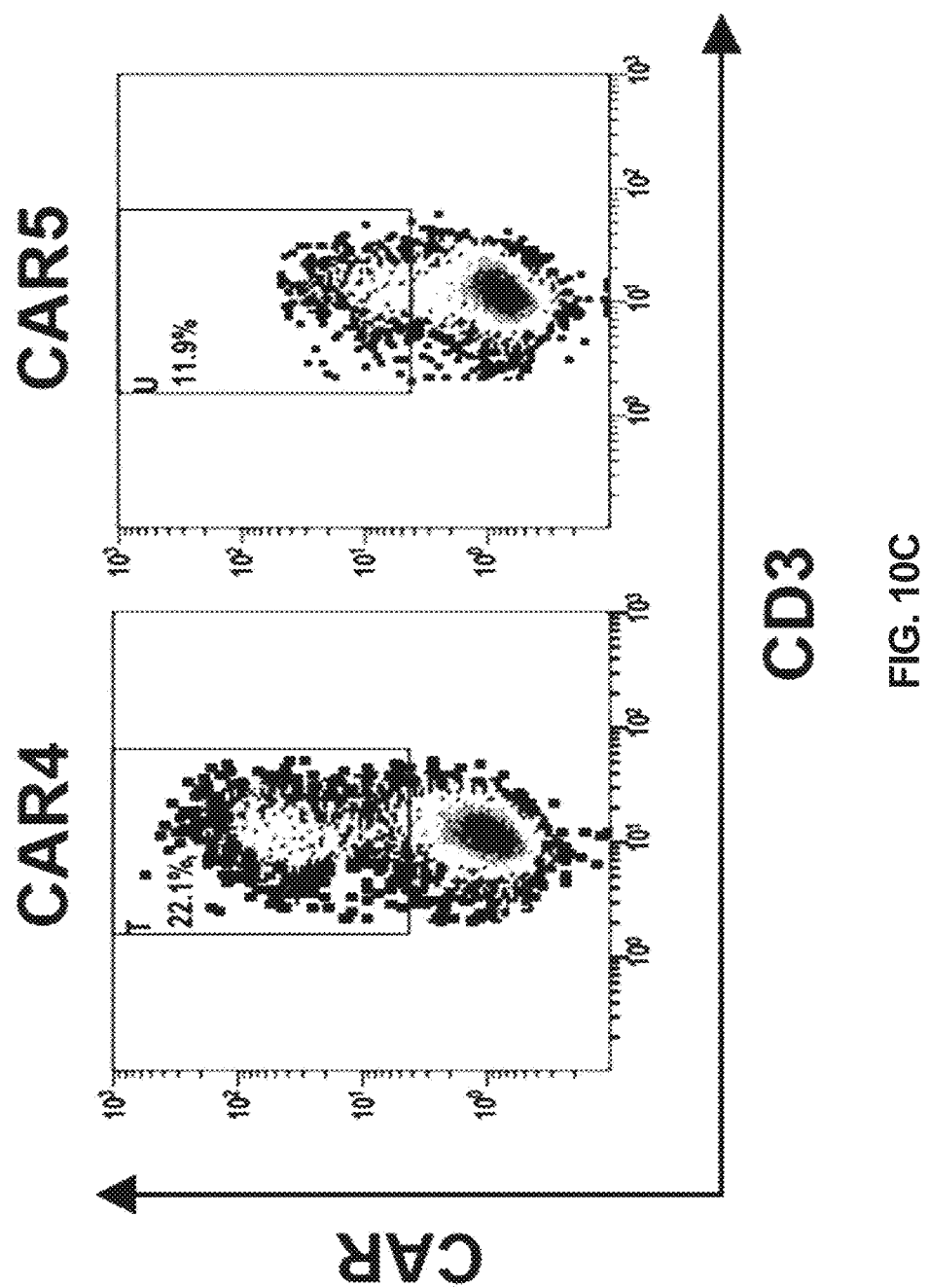
Figure 10D:
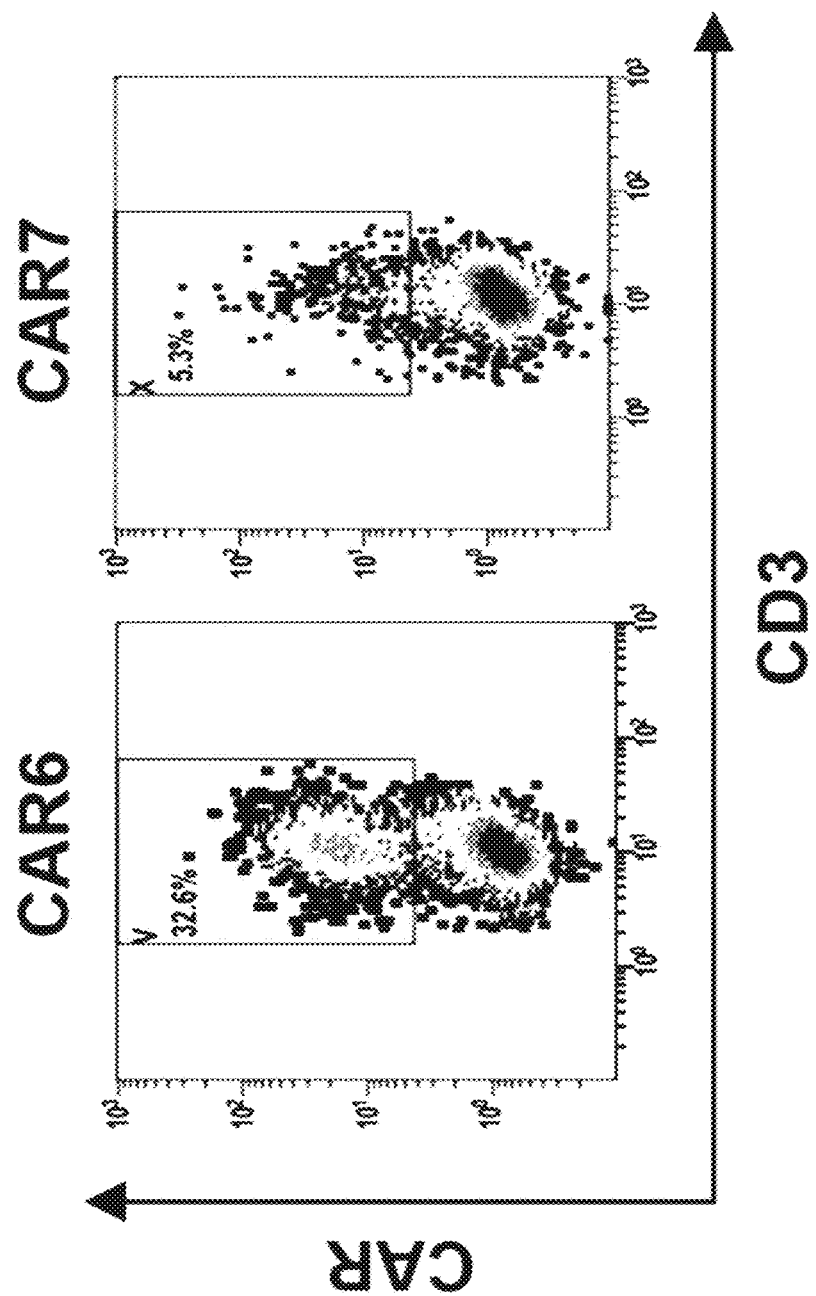

As can be seen in FIG. 8a, significant increases in the secretion of interferon gamma were detected in the experimental group treated with cytotoxic T cells (E) containing the antibody fragment of the present disclosure and the RaJi-Luc cells (T). After the cytotoxic T cells and RaJi-Luc cells were incubated together, luciferase was eluted by lysing the residual RaJi-Luc cells with 3× lysis buffer (75 mM Tris(pH 8.0), 30% glycerol, 3% Triton X100) and reacted with a substrate to examine the cytotoxic effect of the chimeric antigen receptor bearing the antibody fragment of the present disclosure. Percentages of lysis were determined relative to the signal detected in the well where only Raji-Luc cells were cultured. The chimeric antigen receptor T cells having the antibody fragment of the present disclosure increased in cytotoxicity with increasing of the treatment rate. Higher cytotoxic effects were detected in cytotoxic T cells having antibody fragments better in affinity than CD19_12.18 (FIG. 8b).

Example 10: Development of Chimeric Antigen Receptor Through Modification of Hinge Region, Transmembrane Domain, and Costimulatory Domain In order to optimize the activity of chimeric antigen receptors employing the developed antibody fragments, new chimeric antigen receptors (CAR2 to CAR7) were developed by modifying the constituents of chimeric antigen receptors, that is, hinge regions (CD8, CD28, and Fc), transmembrane domains (CD8, CD28, and ICOS), and costimulatory domains (CD137, CD28, ICOS, and CD3). As an antibody fragment binding to CD19 antigen, hzCD19_1218.81 was employed to identify activity (FIG. 9). For the chimeric antigen receptor in each of CAR1 to CAR7, digestion and ligation to pLenti6.3/V5-TOPO lentiviral vector (Invitrogen, USA) in which the promotor had been modified into EF-1 alpha were conducted in the same manner as in Example 8. The constructs thus obtained were identified by base sequencing. Amino acid and nucleotide sequences of the constructs of CAR1 to CAR7 are set forth as SEQ ID NOS: 74 to 87 in the appended sequence listing. Each of the developed constructs was used to prepare and enrich lentivirus according to the protocol of Example 8.

The developed chimeric antigen receptors were analyzed for activity. In this regard, cytotoxic T cells were prepared in the same manner as in Example 4 and examined to see whether or not the activity of CD19-expressing cells was specifically induced.

First, the obtained cytotoxic T cells were examined for CAR expression behavior. The expression of the chimeric antigen receptor was observed with the secondary antibody anti-human IgG FITC (Invitrogen, A11013) following primary binding of CD19-ECD. In this context, in order to examine whether the detected cells would be T cells or not, anti-human CD3 PE (Biolegend, 317308) was allowed to simultaneously participate in the binding, followed by flow cytometry. As a result of the assay, it was observed that the constructs (CAR2, CAR3) in which hinge region change occurred from CD8 to CD28 or Fc greatly decreased in CAR expression, compared to a construct employing a conventional CD8 hinge. In addition, the constructs in which the transmembrane domain and the costimulatory domain were changed were observed to decrease in CAR expression, compared to the case employing ICOS transmembrane domain and costimulatory domain (CAR5) (FIG. 10).

Figure 11A:
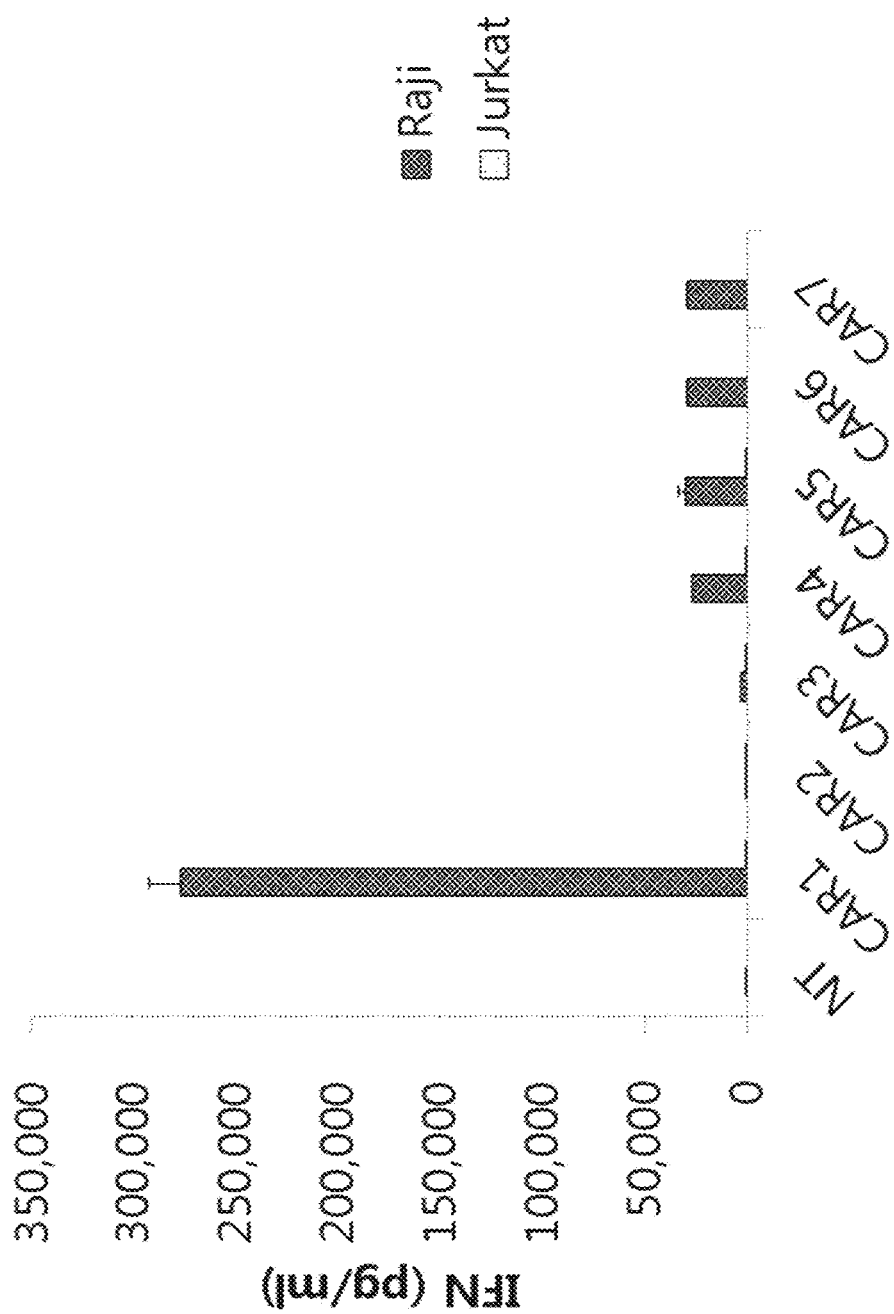
FIG. 11a is a bar graph showing activity of cytotoxic T cells expressing 7 chimeric antigen receptors as measured for levels of interferon gamma. CD19-positive RaJi cells and CD19-negative Jurkat cells were used as target cells and each co-cultured at a ratio of 1:5 with cytotoxic T cells, followed by measuring levels of interferon gamma.
Figure 11B:
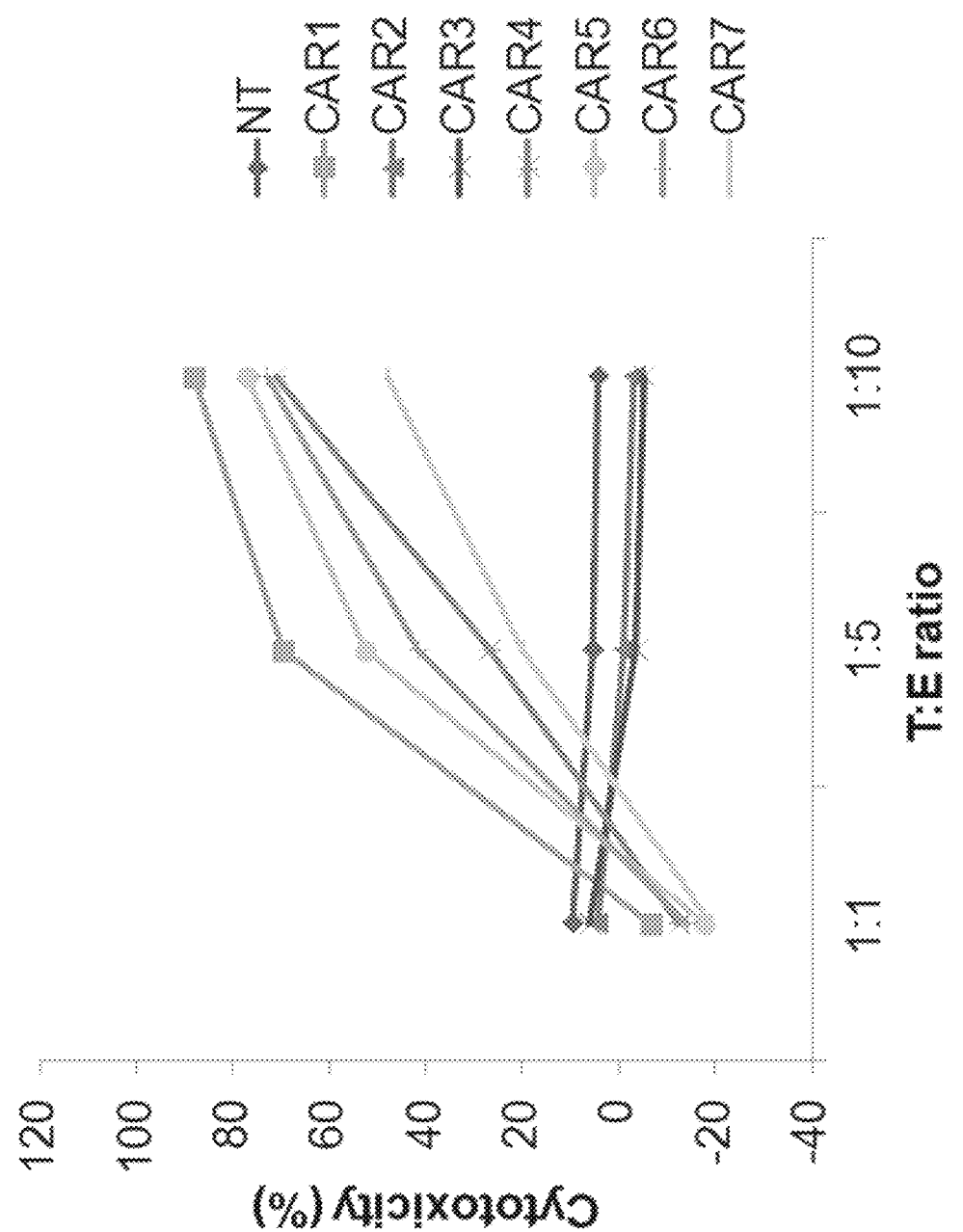
FIG. 11b is a plot showing activity of cytotoxic T cells as measured for luciferase activity of RaJi-Luc surviving after co-cultivation of RaJi-Luc cells and cytotoxic T cells.

The developed cytotoxic T cells were examined for activity in the same manner as in Example 8. CD19 positive RaJi-Luc cells and CD19 negative Jurkat cells were incubated, together with cytotoxic T cells, for 24 hours, and the cell cultures were measured for interferon gamma level and cytotoxicity. As shown in FIG. 11a, an increased level of interferon gamma was detected only in the group in which CD19 positive RaJi-Luc and cytotoxic T cells were co-cultured. Furthermore, construct CAR1, which showed the best expression among the CAR constructs used in the test, induced the highest interferon gamma secretion. Unlike interferon gamma secretion, cytotoxic effects were almost evenly high in all of the constructs CAR1, CAR4, CAR5, CARE (FIG. 11b).

Example 11: Analysis of Epitope for CD19_1218 and Affinity-Improved Antibody

Figure 12A:
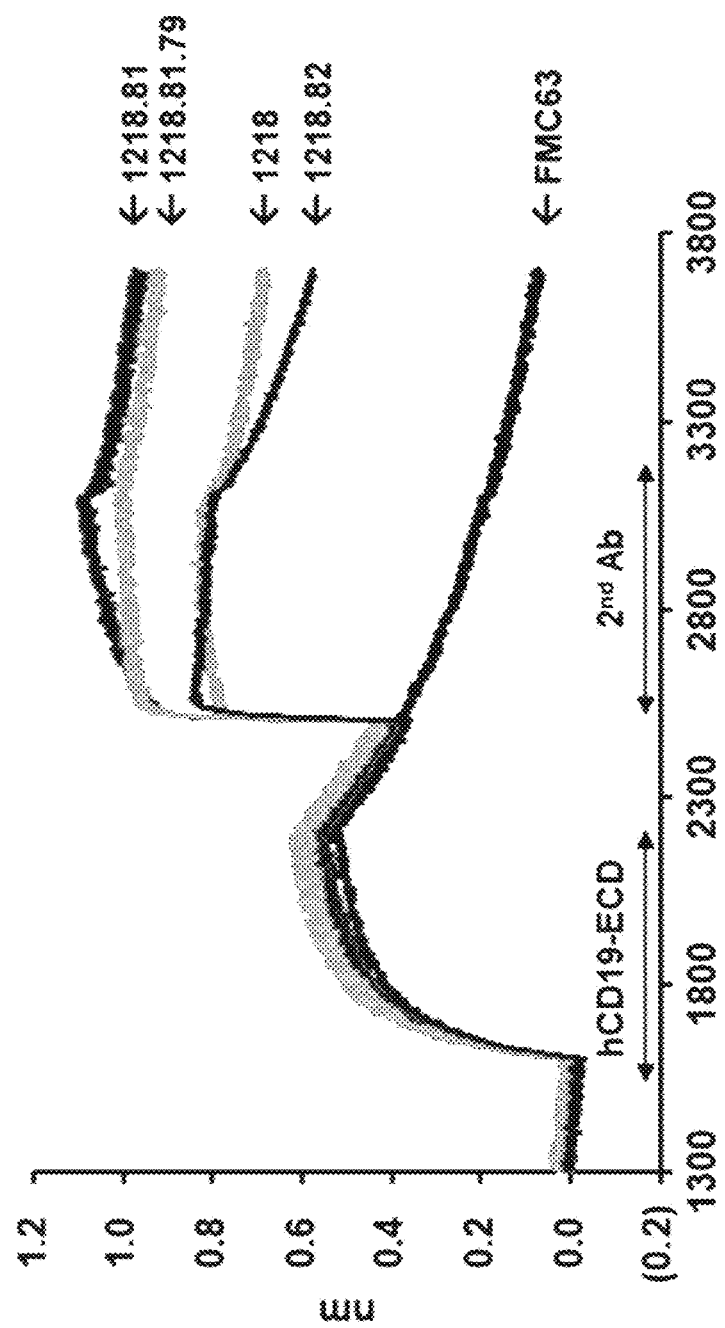
FIG. 12a shows results of the octet test to identify that CD19_1218, CD19_1218.81, CD_19_1218.81.79, and CD_19_1218.82 antibodies bind to epitope sites different from those to which FMC63 binds.
Figure 12B:
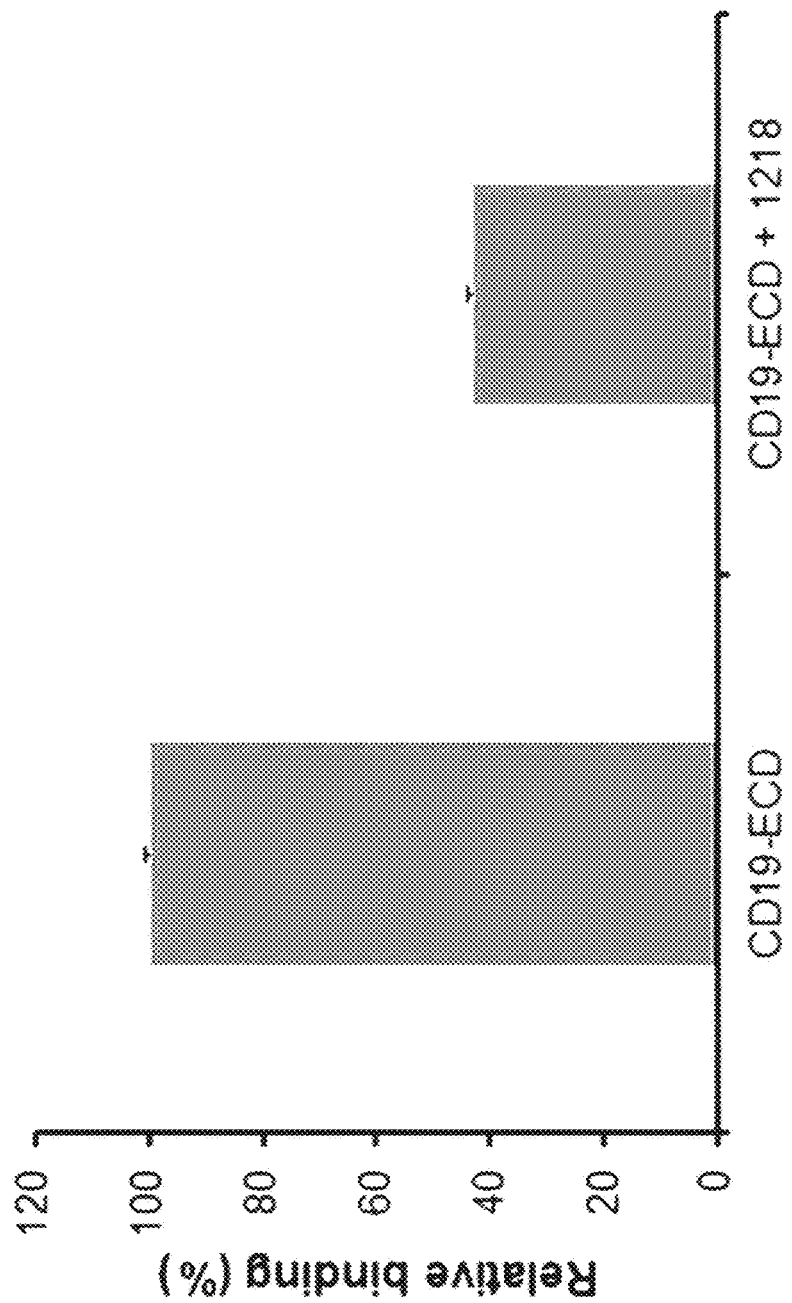
FIG. 12b shows results of competition ELISA using CD19_1218 and CD19_1218.81 antibodies. Relative binding is given when absorbance upon the absence of the competitor (CD19-ECD-Ck alone) is set forth as 100%.

To analyze whether the CD19_1218 antibody and the affinity-improved and humanized antibodies therefrom developed in the present disclosure had an epitope in common with each other, epitope binning and competition ELISA were conducted. As described in Example 2, CD19-ECD protein was bound to FMC63 antibody-immobilized sensor chip to which FMC63, CD19_1218, hzCD19_1218.81, hzCD19_1218.81.79, and hzCD19_1218.82 antibodies were then further applied (FIG. 12a). FMC63 did not further bind to the chip whereas the four antibodies including CD19_1218 did. For competition ELISA, an ELISA plate was coated with CD19_1218.81-Fc antibody at a concentration of 2 μg/mL to which CD19-ECD-Ck (3 μg/mL) was added alone or in combination with CD19_1218-Fc antibody (300 μg/mL). Subsequently, the CD19_1218.81-Fc-bound CD19-ECD-Ck protein was quantitated using an anti-Ck-HRP antibody. The presence of CD19_1218 antibody suppressed the binding of CD19_1218.81-Fc to CD19-ECD-Ck protein (FIG. 12b). Taken together, the data obtained above demonstrate that the developed antibodies have an epitope in common with CD19_1218 antibody.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An anti-CD19 antibody or an antigen-binding fragment thereof, comprising the following:
   (i) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 6;
   (ii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 40;
   (iii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 41;
   (iv) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 30; and a light chain variable region comprising the following light chain CDR amino acid sequence: CDRL1 of SEQ ID NO: 4, CDRL2 of SEQ ID NO: 36, and CDRL3 of SEQ ID NO: 40;
   (v) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 31; and a light chain variable region comprising the following light chain CDR amino acid sequence: CDRL1 of SEQ ID NO: 4, CDRL2 of SEQ ID NO: 5, and CDRL3 of SEQ ID NO: 40;
   (vi) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 32; and a light chain variable region comprising the following light chain CDR amino acid sequence: CDRL1 of SEQ ID NO: 4, CDRL2 of SEQ ID NO: 37, and CDRL3 of SEQ ID NO: 40;
   (vii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 33; and a light chain variable region comprising the following light chain CDR amino acid sequence: CDRL1 of SEQ ID NO: 4, CDRL2 of SEQ ID NO: 38, and CDRL3 of SEQ ID NO: 40;
   (viii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 34; and a light chain variable region comprising the following light chain CDR amino acid sequence: CDRL1 of SEQ ID NO: 4, CDRL2 of SEQ ID NO: 39, and CDRL3 of SEQ ID NO: 40; or (ix) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 35; and a light chain variable region comprising the following light chain CDR amino acid sequence: CDRL1 of SEQ ID NO: 4, CDRL2 of SEQ ID NO: 5, and CDRL3 of SEQ ID NO: 40.

2. The anti-CD19 antibody or the antigen-binding fragment thereof as set forth in claim 1, wherein the heavy chain variable region and the light chain variable region comprises, respectively:
(i) the sequences of SEQ ID NOS: 7 and 8;
(ii) the sequences of SEQ ID NOS: 42 and 43;
(iii) the sequences of SEQ ID NOS: 46 and 47;
(iv) the sequences of SEQ ID NOS: 50 and 51;
(v) the sequences of SEQ ID NOS: 54 and 55;
(vi) the sequences of SEQ ID NOS: 58 and 59;
(vii) the sequences of SEQ ID NOS: 62 and 63;
(viii) the sequences of SEQ ID NOS: 66 and 67; or
(ix) the sequences of SEQ ID NOS: 70 and 71.

3. A CD19-specific chimeric antigen receptor, comprising the following:
(a) an extracellular domain comprising an anti-CD19 antibody or an antigen-binding fragment thereof;
(b) a transmembrane domain; and
(c) an intracellular signaling domain,
wherein the anti-CD19 antibody or the antigen-binding fragment thereof comprises:
(i) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 6;
(ii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 40;
(iii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and a light chain variable region comprising the following light chain CDR amino acid sequence: CDRL1 of SEQ ID NO: 4, CDRL2 of SEQ ID NO: 5, and CDRL3 of SEQ ID NO: 41;
(iv) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 30; and a light chain variable region comprising the following light chain CDR amino acid sequence: CDRL1 of SEQ ID NO: 4, CDRL2 of SEQ ID NO: 36, and CDRL3 of SEQ ID NO: 40;

(v) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 31; and a light chain variable region comprising the following light chain CDR amino acid sequence: CDRL1 of SEQ ID NO: 4, CDRL2 of SEQ ID NO: 5, and CDRL3 of SEQ ID NO: 40;
(vi) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 32; and a light chain variable region comprising the following light chain CDR amino acid sequence: CDRL1 of SEQ ID NO: 4, CDRL2 of SEQ ID NO: 37, and CDRL3 of SEQ ID NO: 40;
(vii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 33; and a light chain variable region comprising the following light chain CDR amino acid sequence: CDRL1 of SEQ ID NO: 4, CDRL2 of SEQ ID NO: 38, and CDRL3 of SEQ ID NO: 40;
(viii) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 34; and a light chain variable region comprising the following light chain CDR amino acid sequence: CDRL1 of SEQ ID NO: 4, CDRL2 of SEQ ID NO: 39, and CDRL3 of SEQ ID NO: 40; or
(ix) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 35; and a light chain variable region comprising the following light chain CDR amino acid sequence: CDRL1 of SEQ ID NO: 4, CDRL2 of SEQ ID NO: 5, and CDRL3 of SEQ ID NO: 40.

4. The CD19-specific chimeric antigen receptor of claim 3, wherein the heavy chain variable region and the light chain variable region comprise, respectively,
(i) the sequences of SEQ ID NOS: 7 and 8;
(ii) the sequences of SEQ ID NOS: 42 and 43;
(iii) the sequences of SEQ ID NOS: 46 and 47;
(iv) the sequences of SEQ ID NOS: 50 and 51;
(v) the sequences of SEQ ID NOS: 54 and 55;
(vi) the sequences of SEQ ID NOS: 58 and 59;
(vii) the sequences of SEQ ID NOS: 62 and 63;
(viii) the sequences of SEQ ID NOS: 66 and 67; or
(ix) the sequences of SEQ ID NOS: 70 and 71.

5. The CD19-specific chimeric antigen receptor of claim 3, wherein the transmembrane domain is a transmembrane domain of a protein selected from the group consisting of alpha, beta, or zeta chain of T-cell receptor, CD27, CD28, CD3 epsilon, CD45, CD4, CD5, CD8, CD8a, CD9, CD16, CD22, CD33, CD37, CD64, CD80, CD86, CD134, CD137, and CD154.

6. The CD19-specific chimeric antigen receptor of claim 3, wherein the intracellular signaling domain is a CD3ζ (CD3 zeta) chain-derived domain.

7. The CD19-specific chimeric antigen receptor of claim 3, wherein the intracellular signaling domain further comprises a costimulatory molecule selected from the group consisting of OX40 (CD134), CD2, CD27, CD28, CDS, ICAM-1, LFA-1 (CD11a/CD18), and 4-1 BB (CD137).

8. A pharmaceutical composition comprising an effector cell expressing the chimeric antigen receptor of claim 3 for treating a CD19 positive cell-associated disease, an autoimmune disease, or an inflammatory disease.

* * * * *

SEQUENCE LISTING

```
<160> NUMBER OF SEQ ID NOS: 93

<210> SEQ ID NO 1
<211> LENGTH: 5
<212> TYPE: PRT
<213> ORGANISM: Artificial Sequence
```

```
<220> FEATURE:
<223> OTHER INFORMATION: Amino acid sequence of CDRH1 of CD19_12.18
      antibody

<400> SEQUENCE: 1

Ser Tyr Asp Met Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of CDRH2 of CD19_12.18
      antibody

<400> SEQUENCE: 2

Gly Ile Asp Asp Asp Gly Arg Tyr Thr Ser Tyr Gly Ser Ala Val Asp
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Amino acid sequence of CDRH3 of CD19_12.18
      antibody

<400> SEQUENCE: 3

Gly Asn Ala Gly Trp Ile Asp Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Amino acid sequence of CDRL1 of CD19_12.18
      antibody

<400> SEQUENCE: 4

Ser Gly Gly Tyr Ser Ser Tyr Tyr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Amino acid sequence of CDRL2 of CD19_12.18
      antibody

<400> SEQUENCE: 5

Glu Ser Asn Lys Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Amino acid sequence of CDRL3 of CD19_12.18
      antibody

<400> SEQUENCE: 6

Gly Gly Trp Asp Ser Thr His Ala Gly Ile
```

```
1               5                   10

<210> SEQ ID NO 7
<211> LENGTH: 117
<212> TYPE: PRT
<213> ORGANISM: Artificial Sequence
<220> FEATURE:
<223> OTHER INFORMATION: Amino acid sequence of heavy chain variable
      region of CD19_12.18 antibody

<400> SEQUENCE: 7

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Thr Arg Gly Asn Ala Gly Trp Ile Asp Ala Trp Gly His Gly Thr Glu
            100                 105                 110

Val Ile Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: Amino acid sequence of light chain variable
      region of CD19_12.18 antibody

<400> SEQUENCE: 8

Leu Thr Gln Pro Ser Ser Val Ser Ala Asn Pro Gly Glu Thr Val Lys
1               5                   10                  15

Ile Thr Cys Ser Gly Gly Tyr Ser Ser Tyr Tyr Gly Trp Tyr Gln Gln
            20                  25                  30

Lys Ser Pro Gly Ser Ala Pro Val Thr Leu Ile Tyr Glu Ser Asn Lys
        35                  40                  45

Arg Pro Ser Asp Ile Pro Ser Arg Phe Ser Gly Ser Ala Ser Gly Ser
    50                  55                  60

Thr Ala Thr Leu Thr Ile Thr Gly Val Gln Val Glu Asp Glu Ala Val
65                  70                  75                  80

Tyr Tyr Cys Gly Gly Trp Asp Ser Thr His Ala Gly Ile Phe Gly Ala
                85                  90                  95

Gly Thr Thr Leu Thr Val Leu Gly Gln Ser
            100                 105

<210> SEQ ID NO 9
<211> LENGTH: 240
<212> TYPE: PRT
<213> ORGANISM: Artificial Sequence
<220> FEATURE:
<223> OTHER INFORMATION: Amino acid sequence of CD19_12.18 scFv

<400> SEQUENCE: 9
```

```
Leu Thr Gln Pro Ser Val Ser Ala Asn Pro Gly Glu Thr Val Lys
1               5                   10                  15

Ile Thr Cys Ser Gly Tyr Ser Tyr Tyr Gly Trp Tyr Gln Gln
            20                  25                  30

Lys Ser Pro Gly Ser Ala Pro Val Thr Leu Ile Tyr Glu Ser Asn Lys
                35                  40                  45

Arg Pro Ser Asp Ile Pro Ser Arg Phe Ser Gly Ser Ala Gly Ser
    50                  55                  60

Thr Ala Thr Leu Thr Ile Thr Gly Val Gln Val Glu Asp Glu Ala Val
65                  70                  75                  80

Tyr Tyr Cys Gly Gly Trp Asp Ser Thr His Ala Gly Ile Phe Gly Ala
            85                  90                  95

Gly Thr Thr Leu Thr Val Leu Gly Gln Ser Ser Arg Ser Ser Gly Gly
            100                 105                 110

Gly Ser Ser Gly Gly Gly Ser Ala Val Thr Leu Asp Glu Ser
        115                 120                 125

Gly Gly Gly Leu Gln Thr Pro Gly Gly Ala Leu Ser Leu Val Cys Lys
        130                 135                 140

Ala Ser Gly Phe Thr Phe Ser Ser Tyr Asp Met Gly Trp Val Arg Gln
145                 150                 155                 160

Ala Pro Gly Lys Gly Leu Glu Phe Val Ala Gly Ile Asp Asp Asp Gly
                165                 170                 175

Arg Tyr Thr Ser Tyr Gly Ser Ala Val Asp Gly Arg Ala Thr Ile Ser
                180                 185                 190

Arg Asp Asn Gly Gln Ser Thr Val Arg Leu Gln Leu Asn Asn Leu Arg
        195                 200                 205

Ala Glu Asp Thr Ala Thr Tyr Tyr Cys Thr Arg Gly Asn Ala Gly Trp
210                 215                 220

Ile Asp Ala Trp Gly His Gly Thr Glu Val Ile Val Ser Ser Thr Ser
225                 230                 235                 240

<210> SEQ ID NO 10
<211> LENGTH: 15
<212> TYPE: DNA
<213> ORGANISM: Artificial Sequence
<220> FEATURE:
<223> OTHER INFORMATION: Nucleotide sequence for encoding CDRH1 of
      CD19_12.18 antibody

<400> SEQUENCE: 10
agttacgaca tgggt                                                        15

<210> SEQ ID NO 11
<211> LENGTH: 51
<212> TYPE: DNA
<213> ORGANISM: Artificial Sequence
<220> FEATURE:
<223> OTHER INFORMATION: Nucleotide sequence for encoding CDRH2 of
      CD19_12.18 antibody

<400> SEQUENCE: 11
ggtattgatg atgatggtag atacacatca tacgggtcgg cggtggatgg c                51

<210> SEQ ID NO 12
<211> LENGTH: 24
<212> TYPE: DNA
<213> ORGANISM: Artificial Sequence
<220> FEATURE:
<223> OTHER INFORMATION: Nucleotide sequence for encoding CDRH3 of
      CD19_12.18 antibody
```

<400> SEQUENCE: 12
ggtaatgctg gttggatcga cgca                                          24

<210> SEQ ID NO 13
<211> LENGTH: 27
<212> TYPE: DNA
<213> ORGANISM: Artificial Sequence
<220> FEATURE:
<223> OTHER INFORMATION: Nucleotide sequence for encoding CDRL1 of
      CD19_12.18 antibody

<400> SEQUENCE: 13 tccggggtt acagcagcta ctatggc                                        27

<210> SEQ ID NO 14
<211> LENGTH: 21
<212> TYPE: DNA
<213> ORGANISM: Artificial Sequence
<220> FEATURE:
<223> OTHER INFORMATION: Nucleotide sequence for encoding CDRL2 of
      CD19_12.18 antibody

<400> SEQUENCE: 14
gaaagcaaca agagaccctc g                                             21

<210> SEQ ID NO 15
<211> LENGTH: 30
<212> TYPE: DNA
<213> ORGANISM: Artificial Sequence
<220> FEATURE:
<223> OTHER INFORMATION: Nucleotide sequence for encoding CDRL3 of
      CD19_12.18 antibody

<400> SEQUENCE: 15
ggtggctggg atagcactca tgctggtata                                    30

<210> SEQ ID NO 16
<211> LENGTH: 351
<212> TYPE: DNA
<213> ORGANISM: Artificial Sequence
<220> FEATURE:
<223> OTHER INFORMATION: Nucleotide sequence for encoding heavy chain
      variable region of CD19_12.18 antibody

<400> SEQUENCE: 16
gccgtgacgt tggacgagtc cggggcggc ctccagacgc ccggaggagc gctcagcctc    60
gtctgcaagg cctccggtt caccttcagt agttacgaca tgggttgggt acgacaggcg   120
cccggcaagg ggctggagtt cgtcgctggt attgatgatg atggtagata cacatcatac   180
gggtcggcgg tggatggccg tgccaccatc tcgagggaca acgggcagag cacagtgagg   240
ctgcagctga caacctcag ggctgaggac accgccacct actactgcac cagaggtaat    300
gctggttgga tcgacgcatg gggccacggg accgaagtca tcgtctcctc c           351

<210> SEQ ID NO 17
<211> LENGTH: 318
<212> TYPE: DNA
<213> ORGANISM: Artificial Sequence
<220> FEATURE:
<223> OTHER INFORMATION: Nucleotide sequence for encoding light chain
      variable region of CD19_12.18 antibody

<400> SEQUENCE: 17
ctgactcagc cgtcctcggt gtcagcaaac ccaggagaaa ccgtcaagat cacctgctcc    60 ggggggttaca gcagctacta tggctggtac cagcagaagt ctcctggcag tgcccctgtc    120
actctgatct atgaaagcaa caagagaccc tcggacatcc cttcacgatt ctccggttcc    180
gcatccggct ccacagccac attaaccatc actggggtcc aagtcgagga cgaggctgtc    240
tattactgtg gtggctggga tagcactcat gctggtatat ttggggccgg acaaccctg    300 accgtcctag gtcagtcc                                                  318

<210> SEQ ID NO 18
<211> LENGTH: 720
<212> TYPE: DNA
<213> ORGANISM: Artificial Sequence
<220> FEATURE:
<223> OTHER INFORMATION: Nucleotide sequence for encoding CD19_12.18
      scFv

<400> SEQUENCE: 18
ctgactcagc cgtcctcggt gtcagcaaac ccaggagaaa ccgtcaagat cacctgctcc    60 ggggggttaca gcagctacta tggctggtac cagcagaagt ctcctggcag tgcccctgtc    120
actctgatct atgaaagcaa caagagaccc tcggacatcc cttcacgatt ctccggttcc    180
gcatccggct ccacagccac attaaccatc actggggtcc aagtcgagga cgaggctgtc    240
tattactgtg gtggctggga tagcactcat gctggtatat ttggggccgg acaaccctg    300 accgtcctag gtcagtcctc tagatcttcc ggcggtggtg gcagctccgg tggtggcggt    360
tccgccgtga cgttggacga gtccgggggc ggcctccaga cgcccggagg agcgctcagc    420
ctcgtctgca aggcctccgg gttcaccttc agtagttacg acatgggttg ggtacgacag    480
gcgcccggca aggggctgga gttcgtcgct ggtattgatg atgatggtag atacacatca    540
tacgggtcgg cggtggatgg ccgtgccacc atctcgaggg acaacgggca gagcacagtg    600
aggctgcagc tgaacaacct cagggctgag gacaccgcca cctactactg caccagaggt    660
aatgctggtt ggatcgacgc atggggccac gggaccgaag tcatcgtctc ctccactagt    720

<210> SEQ ID NO 19
<211> LENGTH: 63
<212> TYPE: DNA
<213> ORGANISM: Artificial Sequence
<220> FEATURE:
<223> OTHER INFORMATION: Nucleotide sequence for encoding CD8 leader

<400> SEQUENCE: 19
atggccctgc ctgtgaccgc tctgctgctg ccctggctc tgctgctgca cgccgctcgc    60
ccc                                                                  63

<210> SEQ ID NO 20
<211> LENGTH: 207
<212> TYPE: DNA
<213> ORGANISM: Artificial Sequence
<220> FEATURE:
<223> OTHER INFORMATION: Nucleotide sequence for encoding CD8
      hinge/transmembrain domain

<400> SEQUENCE: 20
accacaactc cagctccccg gccccctacc cctgcaccaa caatcgccag ccagcctctg    60
tccctgagac cagaggcatg taggccagct gcaggaggag cagtgcatac aagaggcctg    120
gacttcgcct gcgatatcta catttgggct cctctggcag gaacttgtgg cgtgctgctg    180
ctgtctctgg tcatcacccct gtactgc                                       207

<210> SEQ ID NO 21
<211> LENGTH: 126
<212> TYPE: DNA
<213> ORGANISM: Artificial Sequence
<220> FEATURE:
<223> OTHER INFORMATION: Nucleotide sequence for encoding intracellular domain of CD137

<400> SEQUENCE: 21

```
aaaagggcc gcaagaaact gctgtatatt ttcaagcagc ccttcatgcg gcccgtgcag      60
accacacagg aggaagacgg gtgctcctgt agattccccg aggaagagga aggcgggtgt     120
gagctg                                                               126
```

<210> SEQ ID NO 22
<211> LENGTH: 336
<212> TYPE: DNA
<213> ORGANISM: Artificial Sequence
<220> FEATURE:
<223> OTHER INFORMATION: Nucleotide sequence for encoding intracellular domain of CD3-zeta

<400> SEQUENCE: 22

```
cgcgtcaagt tcagccgatc agccgatgct cctgcataca agcagggcca gaatcagctg      60
tataacgagc tgaatctggg gcgccgagag gaatacgacg tgctggataa gcggagaggg     120 agggacccg aaatgggagg caaacctagg cgcaagaacc cacaggaggg actgtacaat     180
gaactgcaga aggacaaaat ggccgaggct tattccgaaa ttgggatgaa aggagagcga     240
cggagaggga agggacacga tgggctgtat cagggactgt ctaccgccac taaagatacc     300
tacgacgctc tgcacatgca ggctctgcca cctcgc                              336
```

<210> SEQ ID NO 23
<211> LENGTH: 1482
<212> TYPE: DNA
<213> ORGANISM: Artificial Sequence
<220> FEATURE:
<223> OTHER INFORMATION: Nucleotide sequence of CAR construct comprising CD19_12.18 scFv

<400> SEQUENCE: 23

```
atggccctgc ctgtgaccgc tctgctgctg cccctggctc tgctgctgca cgccgctcgc      60
cccgtggccc aggcggccct gactcagccg tcctcggtgt cagcaaaccc aggagaaacc     120
gtcaagatca cctgctccgg gggttacagc agctactatg ctggtacca gcagaagtct     180 cctggcagtg cccctgtcac tctgatctat gaaagcaaca gagaccctc ggacatccct     240 tcacgattct ccggttccgc atccggctcc acagccacat taaccatcac tggggtccaa     300
gtcgaggacg aggctgtcta ttactgtggt ggctgggata gcactcatgc tggtatatt     360 ggggccggga caaccctgac cgtcctaggt cagtcctcta gatcttccgg cggtggtggc     420
agctccggtg gtggcggttc cgccgtgacg ttggacgagt ccggggcgg cctccagacg     480 cccggaggag cgctcagcct cgtctgcaag gcctccgggt tcaccttcag tagttacgac     540
atgggttggg tacgacaggc gcccggcaag gggctggagt cgtcgctgg tattgatgat     600 gatggtagat acacatcata cggtcggcg gtggatggcc gtgccaccat ctcgagggac     660
aacgggcaga gcacagtgag gctgcagctg aacaacctca gggctgagga caccgccacc     720
tactactgca ccagaggtaa tgctggttgg atcgacgcat ggggcacgg gaccgaagtc     780 atcgtctcct ccactagtgg ccaggccggc cagaccacaa ctccagctcc ccggcccct     840
```

```
acccctgcac caacaatcgc cagccagcct ctgtccctga gaccagaggc atgtaggcca    900
gctgcaggag gagcagtgca tacaagaggc ctggacttcg cctgcgatat ctacatttgg    960
gctcctctgg caggaacttg tggcgtgctg ctgctgtctc tggtcatcac cctgtactgc   1020
aaaaggggcc gcaagaaact gctgtatatt ttcaagcagc ccttcatgcg gcccgtgcag   1080
accacacagg aggaagacgg gtgctcctgt agattccccg aggaagagga aggcgggtgt   1140
gagctgcgcg tcaagttcag ccgatcagcc gatgctcctg catacaagca gggccagaat   1200
cagctgtata acgagctgaa tctggggcgc cgagaggaat acgacgtgct ggataagcgg   1260
agagggaggg accccgaaat gggaggcaaa cctaggcgca agaacccaca ggagggactg   1320
tacaatgaac tgcagaagga caaaatggcc gaggcttatt ccgaaattgg gatgaaagga   1380
gagcgacgga gagggaaggg acacgatggg ctgtatcagg gactgtctac cgccactaaa   1440
gatacctacg acgctctgca catgcaggct ctgccacctc gc                      1482
```

<210> SEQ ID NO 24
<211> LENGTH: 72
<212> TYPE: DNA
<213> ORGANISM: Artificial Sequence
<220> FEATURE:
<223> OTHER INFORMATION: Heavy chain sense primer for Creation of a
      chicken scFv Ab phage-display library

<400> SEQUENCE: 24

```
ggtcagtcct ctagatcttc cggcggtggt ggcagctccg gtggtggcgg ttccgccgtg    60
acgttggacg ag                                                        72
```

<210> SEQ ID NO 25
<211> LENGTH: 44
<212> TYPE: DNA
<213> ORGANISM: Artificial Sequence
<220> FEATURE:
<223> OTHER INFORMATION: Heavy chain antisense primer for Creation of a
      chicken scFv Ab phage-display library

<400> SEQUENCE: 25

```
ctggccggcc tggccactag tggaggagac gatgacttcg gtcc                     44
```

<210> SEQ ID NO 26
<211> LENGTH: 38
<212> TYPE: DNA
<213> ORGANISM: Artificial Sequence
<220> FEATURE:
<223> OTHER INFORMATION: Light chain sense primer for Creation of a
      chicken scFv Ab phage-display library

<400> SEQUENCE: 26

```
gtggcccagg cggccctgac tcagccgtcc tcggtgtc                            38
```

<210> SEQ ID NO 27
<211> LENGTH: 34
<212> TYPE: DNA
<213> ORGANISM: Artificial Sequence
<220> FEATURE:
<223> OTHER INFORMATION: Light chain antisense primer for Creation of a
      chicken scFv Ab phage-display library

<400> SEQUENCE: 27

```
ggaagatcta gaggactgac ctaggacggt cagg                                34
```

<210> SEQ ID NO 28
<211> LENGTH: 42

```
<212> TYPE: DNA
<213> ORGANISM: Artificial Sequence
<220> FEATURE:
<223> OTHER INFORMATION: Nested sense primer for Creation of a chicken
      scFv Ab phage-display library

<400> SEQUENCE: 28
gaggaggagg aggaggaggt ggcccaggcg gccctgactc ag                    42

<210> SEQ ID NO 29
<211> LENGTH: 47
<212> TYPE: DNA
<213> ORGANISM: Artificial Sequence
<220> FEATURE:
<223> OTHER INFORMATION: Nested antisense primer for Creation of a
      chicken scFv Ab phage-display library

<400> SEQUENCE: 29
gaggaggagg aggaggagga gctggccggc ctggccacta gtggagg               47

<210> SEQ ID NO 30
<211> LENGTH: 8
<212> TYPE: PRT
<213> ORGANISM: Artificial Sequence
<220> FEATURE:
<223> OTHER INFORMATION: CDRH3 of hzCD19_1218.81.12

<400> SEQUENCE: 30

Gly Asn Ala Gly Trp Ile Ser Thr
1               5

<210> SEQ ID NO 31
<211> LENGTH: 8
<212> TYPE: PRT
<213> ORGANISM: Artificial Sequence
<220> FEATURE:
<223> OTHER INFORMATION: CDRH3 of hzCD19_1218.81.17

<400> SEQUENCE: 31

Gly Asn Ala Gly Trp Ile Glu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: CDRH3 of hzCD19_1218.81.52

<400> SEQUENCE: 32

Gly Asn Ala Gly Trp Ile Leu Thr
1               5

<210> SEQ ID NO 33
<211> LENGTH: 8
<212> TYPE: PRT
<213> ORGANISM: Artificial Sequence
<220> FEATURE:
<223> OTHER INFORMATION: CDRH3 of hzCD19_1218.81.55

<400> SEQUENCE: 33

Gly Asn Ala Gly Trp Ile Gln Asn
1               5

<210> SEQ ID NO 34
<211> LENGTH: 8
<212> TYPE: PRT
```

```
<213> ORGANISM: Artificial Sequence
<220> FEATURE:
<223> OTHER INFORMATION: CDRH3 of hzCD19_1218.81.64

<400> SEQUENCE: 34

Gly Asn Ala Gly Trp Ile Gln Thr
1               5

<210> SEQ ID NO 35
<211> LENGTH: 8
<212> TYPE: PRT
<213> ORGANISM: Artificial Sequence
<220> FEATURE:
<223> OTHER INFORMATION: CDRH3 of hzCD19_1218.81.79

<400> SEQUENCE: 35

Gly Asn Ala Gly Trp Ile Asp His
1               5

<210> SEQ ID NO 36
<211> LENGTH: 7
<212> TYPE: PRT
<213> ORGANISM: Artificial Sequence
<220> FEATURE:
<223> OTHER INFORMATION: CDRL2 of hzCD19_1218.81.12

<400> SEQUENCE: 36

Glu Ser Asp Lys Arg Pro Ala
1               5

<210> SEQ ID NO 37
<211> LENGTH: 7
<212> TYPE: PRT
<213> ORGANISM: Artificial Sequence
<220> FEATURE:
<223> OTHER INFORMATION: CDRL2 of hzCD19_1218.81.52

<400> SEQUENCE: 37

Glu Thr Asp Lys Arg Pro Gln
1               5

<210> SEQ ID NO 38
<211> LENGTH: 7
<212> TYPE: PRT
<213> ORGANISM: Artificial Sequence
<220> FEATURE:
<223> OTHER INFORMATION: CDRL2 of hzCD19_1218.81.55

<400> SEQUENCE: 38

Glu Ser Gly Lys Arg Pro Ala
1               5

<210> SEQ ID NO 39
<211> LENGTH: 7
<212> TYPE: PRT
<213> ORGANISM: Artificial Sequence
<220> FEATURE:
<223> OTHER INFORMATION: CDRL2 of hzCD19_1218.81.64

<400> SEQUENCE: 39

Glu Ser Gln Lys Arg Pro Leu
1               5

<210> SEQ ID NO 40
<211> LENGTH: 10
<212> TYPE: PRT
<213> ORGANISM: Artificial Sequence
```

```
<220> FEATURE:
<223> OTHER INFORMATION: CDRL3 of hzCD19_1218.81

<400> SEQUENCE: 40

Gly Gly Leu Thr Pro Thr His Ala Gly Ile
1               5                   10

<210> SEQ ID NO 41
<211> LENGTH: 10
<212> TYPE: PRT
<213> ORGANISM: Artificial Sequence
<220> FEATURE:
<223> OTHER INFORMATION: CDRL3 of hzCD19_1218.82

<400> SEQUENCE: 41

Gly Gln Ser Thr Arg Thr His Ala Gly Ile
1               5                   10

<210> SEQ ID NO 42
<211> LENGTH: 117
<212> TYPE: PRT
<213> ORGANISM: Artificial Sequence
<220> FEATURE:
<223> OTHER INFORMATION: Heavy chain of hzCD19_1218.81 (aa)

<400> SEQUENCE: 42

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Gly Trp Val Arg Gln Ala Pro Gly Lys Gly Leu Glu Phe Val
            35                  40                  45

Ala Gly Ile Asp Asp Asp Gly Arg Tyr Thr Ser Tyr Gly Ser Ala Val
        50                  55                  60

Asp Gly Arg Ala Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Asp Ala Trp Gly Gln Gly Thr Leu
            100                 105                 110

Val Thr Val Ser Ser
        115

<210> SEQ ID NO 43
<211> LENGTH: 105
<212> TYPE: PRT
<213> ORGANISM: Artificial Sequence
<220> FEATURE:
<223> OTHER INFORMATION: Light chain of hzCD19_1218.81 (aa)

<400> SEQUENCE: 43

Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
                20                  25                  30

Tyr Gln Gln Leu Pro Gly Thr Ala Pro Lys Thr Leu Ile Tyr Glu Ser
            35                  40                  45

Asn Lys Arg Pro Ser Gly Ile Pro Asp Arg Phe Ser Gly Ser Ala Ser
        50                  55                  60

Gly Ser Ser Ala Thr Leu Gly Ile Thr Gly Leu Gln Thr Gly Asp Glu
65                  70                  75                  80
```

```
Ala Asp Tyr Tyr Cys Gly Gly Leu Thr Pro Thr His Ala Gly Ile Phe
                85                  90                  95

Gly Gly Gly Thr Lys Leu Thr Val Leu
            100                 105

<210> SEQ ID NO 44
<211> LENGTH: 351
<212> TYPE: DNA
<213> ORGANISM: Artificial Sequence
<220> FEATURE:
<223> OTHER INFORMATION: Heavy chain of hzCD19_1218.81 (nt)

<400> SEQUENCE: 44
gaagttcagc tggttgaatc tggcggagga ctggtgcaac ctggcggatc tctgagactg      60
tcttgtgccg ccagcggctt caccttcagc agctatgata tgggctgggt ccgacaggcc     120
cctggcaaag acttgagtt tgtggccggc atcgacgacg atggcagata cacaagctac     180
ggctctgccg tggatggcag ggccaccatt agcagagaca cgccaagaa caccctgtac     240 ctgcagatga acagcctgag agccgaggac accgccgtgt actactgtac aagaggcaac     300
gccggatgga tcgatgcctg ggacagggc acactggtca ccgtgtcaag c              351

<210> SEQ ID NO 45
<211> LENGTH: 315
<212> TYPE: DNA
<213> ORGANISM: Artificial Sequence
<220> FEATURE:
<223> OTHER INFORMATION: Light chain of hzCD19_1218.81 (nt)

<400> SEQUENCE: 45
cagtctgtgc tgacacagcc tccatctgtg tctgctgccc ctggccagaa agtgacaatc      60
agctgtagcg gcggctactc cagctactac ggatggtatc agcagctgcc tggcacagcc     120
cctaagacac tgatctacga gagcaacaag aggcccagcg gcatccctga tagattttct     180
ggcagcgcct ctggcagctc tgccacactg gaattacag gactgcagac aggcgacgag     240
gccgattact attgtggcgg cctgacacct acacacgccg gaattttggg cggaggcacc     300
aagctgacag tgctc                                                     315

<210> SEQ ID NO 46
<211> LENGTH: 117
<212> TYPE: PRT
<213> ORGANISM: Artificial Sequence
<220> FEATURE:
<223> OTHER INFORMATION: Heavy chain of hzCD19_1218.81.12 (aa)

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95
```

Thr Arg Gly Asn Ala Gly Trp Ile Ser Thr Trp Gly Gln Gly Thr Leu
            100                 105                 110

Val Thr Val Ser Ser
        115

<210> SEQ ID NO 47
<211> LENGTH: 105
<212> TYPE: PRT
<213> ORGANISM: Artificial Sequence
<220> FEATURE:
<223> OTHER INFORMATION: Light chain of hzCD19_1218.81.12 (aa)

<400> SEQUENCE: 47

Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
            20                  25                  30

Tyr Gln Gln Leu Pro Gly Thr Ala Pro Lys Thr Leu Ile Tyr Glu Ser
        35                  40                  45

Asp Lys Arg Pro Ala Gly Ile Pro Asp Arg Phe Ser Gly Ser Ala Ser
    50                  55                  60

Gly Ser Ser Ala Thr Leu Gly Ile Thr Gly Leu Gln Thr Gly Asp Glu
65                  70                  75                  80

Ala Asp Tyr Tyr Cys Gly Gly Leu Thr Pro Thr His Ala Gly Ile Phe
                85                  90                  95

Gly Gly Gly Thr Lys Leu Thr Val Leu
            100                 105

<210> SEQ ID NO 48
<211> LENGTH: 351
<212> TYPE: DNA
<213> ORGANISM: Artificial Sequence
<220> FEATURE:
<223> OTHER INFORMATION: Heavy chain of hzCD19_1218.81.12 (nt)

<400> SEQUENCE: 48
gaggtgcagc tggtagagtc cggcggcggc ctcgtccaac caggcggctc cctcagattg       60
agctgtgctg ccagcggctt cactttcagc tcttatgaca tgggttgggt gagacaggca      120
cctggcaagg gtctggaatt cgtagccggc atcgacgatg acggtagata caccagttac      180
ggctctgctg tcgatggtcg cgctaccatt agccgagata cgccaagaa taccgtttat       240 cttcaaatga attcactgag gcagaagac acagccgttt actattgtac tagaggtaac      300
gccgggtgga tttcgacttg gggacagggc acactggtga ccgtgagttc a               351

<210> SEQ ID NO 49
<211> LENGTH: 315
<212> TYPE: DNA
<213> ORGANISM: Artificial Sequence
<220> FEATURE:
<223> OTHER INFORMATION: Light chain of hzCD19_1218.81.12 (nt)

<400> SEQUENCE: 49
cagtcagtcc taactcagcc cccctcagtg agtgcggctc cggggcagaa agtgacaatc       60
tcgtgcagcg gaggctacag ctcttattac ggatggtatc agcagctgcc aggaaccgcc      120
cccaagaccc ttatctacga gtccgacaaa cggcctgcag ggataccaga caggttttca      180
ggcagtgcgt ctggttcctc tgccacgctc ggcatcaccg gctgcaaac aggagacgag       240 gcagattatt attgcggagg actgacgcct actcacgcag gaattttttgg aggtggaaca    300

```
aaattaacag tgttg                                                    315

<210> SEQ ID NO 50
<211> LENGTH: 117
<212> TYPE: PRT
<213> ORGANISM: Artificial Sequence
<220> FEATURE:
<223> OTHER INFORMATION: Heavy chain of hzCD19_1218.81.17 (aa)

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Glu Thr Trp Gly Gln Gly Thr Leu
            100                 105                 110

Val Thr Val Ser Ser
        115

<210> SEQ ID NO 51
<211> LENGTH: 105
<212> TYPE: PRT
<213> ORGANISM: Artificial Sequence
<220> FEATURE:
<223> OTHER INFORMATION: Light chain of hzCD19_1218.81.17 (aa)

<400> SEQUENCE: 51

Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
            20                  25                  30

Tyr Gln Gln Leu Pro Gly Thr Ala Pro Lys Thr Leu Ile Tyr Glu Ser
        35                  40                  45

Asn Lys Arg Pro Ser Gly Ile Pro Asp Arg Phe Ser Gly Ser Ala Ser
    50                  55                  60

Gly Ser Ser Ala Thr Leu Gly Ile Thr Gly Leu Gln Thr Gly Asp Glu
65                  70                  75                  80

Ala Asp Tyr Tyr Cys Gly Gly Leu Thr Pro Thr His Ala Gly Ile Phe
                85                  90                  95

Gly Gly Gly Thr Lys Leu Thr Val Leu
            100                 105

<210> SEQ ID NO 52
<211> LENGTH: 351
<212> TYPE: DNA
<213> ORGANISM: Artificial Sequence
<220> FEATURE:
<223> OTHER INFORMATION: Heavy chain of hzCD19_1218.81.17 (nt)

<400> SEQUENCE: 52
gaggtgcagc tggtagagtc cggcggcggc ctcgtccaac caggcggctc cctcagattg     60
```

```
agctgtgctg ccagcggctt cactttcagc tcttatgaca tgggttgggt gagacaggca      120
cctggcaagg gtctggaatt cgtagccggc atcgacgatg acggtagata caccagttac      180
ggctctgctg tcgatggtcg cgctaccatt agccgagata cgccaagaa taccgtttat       240 cttcaaatga attcactgag ggcagaagac acagccgttt actattgtac tagaggtaac      300
gccgggtgga ttgagacgtg gggacagggc acactggtga ccgtgagttc a               351
```

<210> SEQ ID NO 53
<211> LENGTH: 315
<212> TYPE: DNA
<213> ORGANISM: Artificial Sequence
<220> FEATURE:
<223> OTHER INFORMATION: Light chain of hzCD19_1218.81.17 (nt)

<400> SEQUENCE: 53

```
cagtcagtcc taactcagcc ccctcagtg agtgcggctc cggggcagaa agtgacaatc       60
tcgtgcagcg gaggctacag ctcttattac ggatggtatc agcagctgcc aggaaccgcc      120
cccaagaccc ttatctacga gtcaaataaa cggccttcag ggataccaga caggttttca      180
ggcagtgcgt ctggttcctc tgccacgctc ggcatcaccg gctgcaaac aggagacgag       240 gcagattatt attgcggagg actgacgcct actcacgcag aatttttgg aggtggaaca       300 aaattaacag tgttg                                                       315
```

<210> SEQ ID NO 54
<211> LENGTH: 117
<212> TYPE: PRT
<213> ORGANISM: Artificial Sequence
<220> FEATURE:
<223> OTHER INFORMATION: Heavy chain of hzCD19_1218.81.52 (aa)

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Glu Thr Trp Gly Gln Gly Thr Leu
            100                 105                 110

Val Thr Val Ser Ser
        115

<210> SEQ ID NO 55
<211> LENGTH: 105
<212> TYPE: PRT
<213> ORGANISM: Artificial Sequence
<220> FEATURE:
<223> OTHER INFORMATION: Light chain of hzCD19_1218.81.52 (aa)

<400> SEQUENCE: 55

Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
            20                  25                  30

Tyr Gln Gln Leu Pro Gly Thr Ala Pro Lys Thr Leu Ile Tyr Glu Thr
                35                  40                  45

Asp Lys Arg Pro Gln Gly Ile Pro Asp Arg Phe Ser Gly Ser Ala Ser
        50                  55                  60

Gly Ser Ser Ala Thr Leu Gly Ile Thr Gly Leu Gln Thr Gly Asp Glu
65                  70                  75                  80

Ala Asp Tyr Tyr Cys Gly Gly Leu Thr Pro Thr His Ala Gly Ile Phe
                85                  90                  95

Gly Gly Gly Thr Lys Leu Thr Val Leu
                100                 105

<210> SEQ ID NO 56
<211> LENGTH: 351
<212> TYPE: DNA
<213> ORGANISM: Artificial Sequence
<220> FEATURE:
<223> OTHER INFORMATION: Heavy chain of hzCD19_1218.81.52 (nt)

<400> SEQUENCE: 56
gaggtgcagc tggtagagtc cggcggcggc ctcgtccaac aggcggctc cctcagattg      60 agctgtgctg ccagcggctt cactttcagc tcttatgaca tgggttgggt gagacaggca    120
cctggcaagg gtctggaatt cgtagccggc atcgacgatg acgtagata caccagttac     180 ggctctgctg tcgatggtcg cgctaccatt agccgagata cgccaagaa taccgtttat     240 cttcaaatga attcactgag ggcagaagac acagccgttt actattgtac tagaggtaac    300
gccgggtgga ttcttacttg gggacagggc acactggtga ccgtgagttc a             351

<210> SEQ ID NO 57
<211> LENGTH: 315
<212> TYPE: DNA
<213> ORGANISM: Artificial Sequence
<220> FEATURE:
<223> OTHER INFORMATION: Light chain of hzCD19_1218.81.52 (nt)

<400> SEQUENCE: 57
cagtcagtcc taactcagcc cccctcagtg agtgcggctc cggggcagaa agtgacaatc     60
tcgtgcagcg gaggctacag ctcttattac ggatggtatc agcagctgcc aggaaccgcc    120
cccaagaccc ttatctacga gactgataaa cggcctcagg ggataccaga caggttttca    180
ggcagtgcgt ctggttcctc tgccacgctc ggcatcaccg gctgcaaac aggagacgag     240 gcagattatt attgtggagg actgacgcct actcacgcag aattttttgg aggtggaaca    300
aaattaacag tgttg                                                      315

<210> SEQ ID NO 58
<211> LENGTH: 117
<212> TYPE: PRT
<213> ORGANISM: Artificial Sequence
<220> FEATURE:
<223> OTHER INFORMATION: Heavy chain of hzCD19_1218.81.55 (aa)

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val

```
            35                  40                  45

Ala Gly Ile Asp Asp Gly Arg Tyr Thr Ser Tyr Gly Ser Ala Val
        50                  55                  60

Asp Gly Arg Ala Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Gln Asn Trp Gly Gln Gly Thr Leu
            100                 105                 110

Val Thr Val Ser Ser
        115

<210> SEQ ID NO 59
<211> LENGTH: 105
<212> TYPE: PRT
<213> ORGANISM: Artificial Sequence
<220> FEATURE:
<223> OTHER INFORMATION: Light chain of hzCD19_1218.81.55 (aa)

<400> SEQUENCE: 59

Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
            20                  25                  30

Tyr Gln Gln Leu Pro Gly Thr Ala Pro Lys Thr Leu Ile Tyr Glu Ser
        35                  40                  45

Gly Lys Arg Pro Ala Gly Ile Pro Asp Arg Phe Ser Gly Ser Ala Ser
50                  55                  60

Gly Ser Ser Ala Thr Leu Gly Ile Thr Gly Leu Gln Thr Gly Asp Glu
65                  70                  75                  80

Ala Asp Tyr Tyr Cys Gly Gly Leu Thr Pro Thr His Ala Gly Ile Phe
                85                  90                  95

Gly Gly Gly Thr Lys Leu Thr Val Leu
            100                 105

<210> SEQ ID NO 60
<211> LENGTH: 351
<212> TYPE: DNA
<213> ORGANISM: Artificial Sequence
<220> FEATURE:
<223> OTHER INFORMATION: Heavy chain of hzCD19_1218.81.55 (nt)

<400> SEQUENCE: 60
gaggtgcagc tggtagagtc cggcggcggc ctcgtccaac caggcggctc cctcagattg      60
agctgtgctg ccagcggctt cactttcagc tcttatgaca tgggttgggt gagacaggca     120
cctggcaagg gtctggaatt cgtagccggc atcgacgatg acggtagata caccagttac     180
ggctctgctg tcgatggtcg cgctaccatt agccgagata cgccaagaa taccgtttat      240 cttcaaatga attcactgag gcagaagac acagccgttt actattgtac tagaggtaac      300
gccgggtgga ttcagaattg ggacagggc acactggtga ccgtgagttc a               351

<210> SEQ ID NO 61
<211> LENGTH: 315
<212> TYPE: DNA
<213> ORGANISM: Artificial Sequence
<220> FEATURE:
<223> OTHER INFORMATION: Light chain of hzCD19_1218.81.55 (nt)

<400> SEQUENCE: 61
```

```
cagtcagtcc taactcagcc ccctcagtg agtgcggctc cggggcagaa agtgacaatc      60
tcgtgcagcg gaggctacag ctcttattac ggatggtatc agcagctgcc aggaaccgcc     120
cccaagaccc ttatctacga gtcggggaaa cggcctgcgg ggataccaga caggttttca     180
ggcagtgcgt ctggttcctc tgccacgctc ggcatcaccg gctgcaaac aggagacgag      240 gcagattatt attgcggagg actgacgcct actcacgcag gaattttgg aggtggaaca      300 aaattaacag tgttg                                                       315
```

<210> SEQ ID NO 62
<211> LENGTH: 117
<212> TYPE: PRT
<213> ORGANISM: Artificial Sequence
<220> FEATURE:
<223> OTHER INFORMATION: Heavy chain of hzCD19_1218.81.64 (aa)

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Gln Thr Trp Gly Gln Gly Thr Leu
            100                 105                 110

Val Thr Val Ser Ser
        115
```

<210> SEQ ID NO 63
<211> LENGTH: 105
<212> TYPE: PRT
<213> ORGANISM: Artificial Sequence
<220> FEATURE:
<223> OTHER INFORMATION: Light chain of hzCD19_1218.81.64 (aa)

<400> SEQUENCE: 63

```
Gln Ser Val Leu Thr Gln Pro Pro Ser Val Ser Ala Ala Pro Gly Gln
1               5                   10                  15

Lys Val Thr Ile Ser Cys Ser Gly Gly Tyr Ser Ser Tyr Tyr Gly Trp
            20                  25                  30

Tyr Gln Gln Leu Pro Gly Thr Ala Pro Lys Thr Leu Ile Tyr Glu Ser
        35                  40                  45

Gln Lys Arg Pro Leu Gly Ile Pro Asp Arg Phe Ser Gly Ser Ala Ser
    50                  55                  60

Gly Ser Ser Ala Thr Leu Asp Ile Thr Gly Leu Gln Thr Gly Asp Glu
65                  70                  75                  80

Ala Asp Tyr Tyr Cys Gly Gly Leu Thr Pro Thr His Ala Gly Ile Phe
                85                  90                  95

Gly Gly Gly Thr Lys Leu Thr Val Leu
            100                 105
```

```
<210> SEQ ID NO 64
<211> LENGTH: 351
<212> TYPE: DNA
<213> ORGANISM: Artificial Sequence
<220> FEATURE:
<223> OTHER INFORMATION: Heavy chain of hzCD19_1218.81.64 (nt)

<400> SEQUENCE: 64
gaggtgcagc tggtagagtc cggcggcggc ctcgtccaac caggcggctc cctcagattg      60
agctgtgctg ccagcggctt cactttcagc tcttatgaca tgggttgggt gagacaggca     120
cctggcaagg gtctggaatt cgtagccggc atcgacgatg acggtagata caccagttac     180
ggctctgctg tcgatggtcg cgctaccatt agccgagata cgccaagaa taccgtttat      240 cttcaaatga attcactgag ggcagaagac acagccgttt actattgtac tagaggtaac     300 gccggtgga ttcagacgtg gggacagggc acactggtga ccgtgagttc a               351

<210> SEQ ID NO 65
<211> LENGTH: 315
<212> TYPE: DNA
<213> ORGANISM: Artificial Sequence
<220> FEATURE:
<223> OTHER INFORMATION: Light chain of hzCD19_1218.81.64 (nt)

<400> SEQUENCE: 65
cagtcagtcc taactcagcc cccctcagtg agtgcggctc cggggcagaa agtgacaatc      60
tcgtgcagcg gaggctacag ctcttattac ggatggtatc agcagctgcc aggaaccgcc     120
cccaagaccc ttatctacga gtctcagaaa cggcctcttg ggataccaga caggttttca     180
ggcagtgcgt ctggttcctc tgccacgctc gacatcaccg ggctgcaaac aggagacgag     240
gcagattatt attgcggagg actgacgcct actcacgcag gaatttttgg aggtggaaca     300
aaattaacag tgttg                                                       315

<210> SEQ ID NO 66
<211> LENGTH: 117
<212> TYPE: PRT
<213> ORGANISM: Artificial Sequence
<220> FEATURE:
<223> OTHER INFORMATION: Heavy chain of hzCD19_1218.81.79 (aa)

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Gly Trp Val Arg Gln Ala Pro Gly Lys Gly Leu Glu Phe Val
        35                  40                  45

Ala Gly Ile Asp Asp Asp Gly Arg Tyr Thr Ser Tyr Gly Ser Ala Val
    50                  55                  60

Asp Gly Arg Ala Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Ala Gly Trp Ile Asp His Trp Gly Gln Gly Thr Leu
            100                 105                 110

Val Thr Val Ser Ser
        115

<210> SEQ ID NO 67
```

<211> LENGTH: 105
<212> TYPE: PRT
<213> ORGANISM: Artificial Sequence
<220> FEATURE:
<223> OTHER INFORMATION: Light chain of hzCD19_1218.81.79 (aa)

<400> SEQUENCE: 67

Gln Ser Val Leu Thr Gln Pro Pro Ser Val Ser Ala Ala Pro Gly Gln
1               5                   10                  15
Lys Val Thr Ile Ser Cys Ser Gly Gly Tyr Ser Tyr Tyr Gly Trp
            20                  25                  30
Tyr Gln Gln Leu Pro Gly Thr Ala Pro Lys Thr Leu Ile Tyr Glu Ser
        35                  40                  45
Asn Lys Arg Pro Ser Gly Ile Pro Asp Arg Phe Ser Gly Ser Ala Ser
    50                  55                  60
Gly Ser Ser Ala Thr Leu Gly Ile Thr Gly Leu Gln Thr Gly Asp Glu
65                  70                  75                  80
Ala Asp Tyr Tyr Cys Gly Gly Leu Thr Pro Thr His Ala Gly Ile Phe
                85                  90                  95
Gly Gly Gly Thr Lys Leu Thr Val Leu
            100                 105

<210> SEQ ID NO 68
<211> LENGTH: 351
<212> TYPE: DNA
<213> ORGANISM: Artificial Sequence
<220> FEATURE:
<223> OTHER INFORMATION: Heavy chain of hzCD19_1218.81.79 (nt)

<400> SEQUENCE: 68
gaagttcagc tggttgaatc tggcggagga ctggtgcaac tggcggatc tctgagactg      60 tcttgtgccg ccagcggctt caccttcagc agctatgata tgggctgggt ccgacaggcc    120
cctggcaaag gacttgagtt tgtggccggc atcgacgacg atgcagata cacaagctac     180 ggctctgccg tggatggcag ggccaccatt agcagagaca cgccaagaa caccctgtac     240 ctgcagatga acagcctgag agccgaggac accgccgtgt actactgtac aagaggcaac    300
gccggctgga tcgatcactg gggacagggc acactggtca ccgtgtctag c             351

<210> SEQ ID NO 69
<211> LENGTH: 315
<212> TYPE: DNA
<213> ORGANISM: Artificial Sequence
<220> FEATURE:
<223> OTHER INFORMATION: Light chain of hzCD19_1218.81.79 (nt)

<400> SEQUENCE: 69
cagtctgtgc tgacacagcc tccatctgtg tctgctgccc ctggccagaa agtgacaatc      60
agctgtagcg gcggctactc cagctactac ggatggtatc agcagctgcc tggcacagcc    120
cctaagacac tgatctacga gagcaacaag aggcccagcg gcatccctga tagattttct    180
ggcagcgcct ctggcagctc tgccacactg ggaattacag gactgcagac aggcgacgag    240
gccgattact attgtggcgg cctgacacct acacacgccg gaattttttgg cggaggcacc   300 aagctgacag tgctc                                                      315

<210> SEQ ID NO 70
<211> LENGTH: 117
<212> TYPE: PRT
<213> ORGANISM: Artificial Sequence
<220> FEATURE:

<223> OTHER INFORMATION: Heavy chain of hzCD19_1218.81.82 (aa)

<400> SEQUENCE: 70

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met Gly Trp Val Arg Gln Ala Pro Gly Lys Gly Leu Glu Phe Val
        35                  40                  45
Ala Gly Ile Asp Asp Asp Gly Arg Tyr Thr Ser Tyr Gly Ser Ala Val
    50                  55                  60
Asp Gly Arg Ala Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Gly Asn Ala Gly Trp Ile Asp Ala Trp Gly Gln Gly Thr Leu
            100                 105                 110
Val Thr Val Ser Ser
        115
```

<210> SEQ ID NO 71
<211> LENGTH: 105
<212> TYPE: PRT
<213> ORGANISM: Artificial Sequence
<220> FEATURE:
<223> OTHER INFORMATION: Light chain of hzCD19_1218.81.82 (aa)

<400> SEQUENCE: 71

```
Gln Ser Val Leu Thr Gln Pro Pro Ser Val Ser Ala Ala Pro Gly Gln
1               5                   10                  15
Lys Val Thr Ile Ser Cys Ser Gly Gly Tyr Ser Ser Tyr Tyr Gly Trp
            20                  25                  30
Tyr Gln Gln Leu Pro Gly Thr Ala Pro Lys Thr Leu Ile Tyr Glu Ser
        35                  40                  45
Asn Lys Arg Pro Ser Gly Ile Pro Asp Arg Phe Ser Gly Ser Ala Ser
    50                  55                  60
Gly Ser Ser Ala Thr Leu Gly Ile Thr Gly Leu Gln Thr Gly Asp Glu
65                  70                  75                  80
Ala Asp Tyr Tyr Cys Gly Gln Ser Thr Arg Thr His Ala Gly Ile Phe
                85                  90                  95
Gly Gly Gly Thr Lys Leu Thr Val Leu
            100                 105
```

<210> SEQ ID NO 72
<211> LENGTH: 351
<212> TYPE: DNA
<213> ORGANISM: Artificial Sequence
<220> FEATURE:
<223> OTHER INFORMATION: Heavy chain of hzCD19_1218.81.82 (nt)

<400> SEQUENCE: 72

```
gaagttcagc tggttgaatc tggcggagga ctggtgcaac ctggcggatc tctgagactg      60
tcttgtgccg ccagcggctt caccttcagc agctatgata tgggctgggt ccgacaggcc     120
cctggcaaag gacttgagtt tgtggccggc atcgacgacg atggcagata cacaagctac     180
ggctctgccg tggatggcag ggccaccatt agcagagaca cgccaagaa cacccctgtac    240
ctgcagatga acagcctgag agccgaggac accgccgtgt actactgtac aagaggcaac     300
```
gccggatgga tcgatgcctg gggacagggc acactggtca ccgtgtcaag c           351

<210> SEQ ID NO 73
<211> LENGTH: 315
<212> TYPE: DNA
<213> ORGANISM: Artificial Sequence
<220> FEATURE:
<223> OTHER INFORMATION: Light chain of hzCD19_1218.81.82 (nt)

<400> SEQUENCE: 73
cagtctgtgc tgacacagcc tccatctgtg tctgctgccc ctggccagaa agtgacaatc    60
agctgtagcg gcggctactc cagctactac ggatggtatc agcagctgcc tggcacagcc   120
cctaagacac tgatctacga gcaacaagag gcccagcg gcatccctga tagattttct    180
ggcagcgcct ctggcagctc tgccacactg gaattacag actgcagac aggcgacgag    240 gccgattact actgtggcca gtctacaaga acccacgccg aatctttgg cggaggcaca   300 aaactgacag tgctc                                                   315

<210> SEQ ID NO 74
<211> LENGTH: 669
<212> TYPE: DNA
<213> ORGANISM: Artificial Sequence
<220> FEATURE:
<223> OTHER INFORMATION: CAR1 construct without scFv (nt)

<400> SEQUENCE: 74
acaacgacac tgctcccag accgcctact cccgccccaa ccattgcatc tcagccactc    60
tctctgagac ccgaagcgtg tagacctgcg gccggggggcg ctgtccacac aagaggctta   120
gacttcgcct gcgatatcta tatctgggcc ccactcgcag gcacttgtgg agtgctgctg   180 cttcactcg tgataaccct gtactgcaaa aggggagaa agaagctgct gtatattttt    240
aaacaaccat ttatgagacc tgttcagact acccaggaag aagacggttg tagttgcaga   300
ttccccgagg aggaagaagg aggttgcgag ttgagagtaa agttcagcag atccgcagat    360
gcccctgctt accagcaggg tcaaaaccag ctttacaacg agctgaattt aggtagaaga   420
gaggaatatg acgtgttgga taaaagaaga ggaagagacc cggaaatggg cggcaagcct   480
cgaagaaaaa atccccaaga gggactctac aatgagctgc agaaggacaa aatggctgaa   540
gcctacagcg agatcggcat gaagggagaa agacgcagag ggaaagggca tgatgggctt   600
tatcagggct tgtccaccgc tacaaaggat acttatgacg cactacacat gcaggccctg   660
ccacccccgt                                                          669

<210> SEQ ID NO 75
<211> LENGTH: 223
<212> TYPE: PRT
<213> ORGANISM: Artificial Sequence
<220> FEATURE:
<223> OTHER INFORMATION: CAR1 construct without scFv (aa)

<400> SEQUENCE: 75

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

-continued

```
Ile Thr Leu Tyr Cys Lys Arg Gly Arg Lys Lys Leu Leu Tyr Ile Phe
 65                  70                  75                  80

Lys Gln Pro Phe Met Arg Pro Val Gln Thr Thr Gln Glu Glu Asp Gly
             85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
    130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220

<210> SEQ ID NO 76
<211> LENGTH: 651
<212> TYPE: DNA
<213> ORGANISM: Artificial Sequence
<220> FEATURE:
<223> OTHER INFORMATION: CAR2 construct without scFv (nt)

<400> SEQUENCE: 76
atcgaggtga tgtaccctcc tccctatctc gataacgaga atctaacgg  caccatcatc    60 catgtgaaag ggaaacacct ctgcccttca ccactcttcc caggtccgag caagccaatt   120
tatatctggg caccgttggc ggggacttgc ggagtgcttt tactttcact ggttattacg   180
ctgtactgta acgcggtcg gaagaagctc ctttacattt tcaagcagcc ttttatgcgc    240
ccagtgcaga ccacacagga ggaagatggc tgtagttgca gatttcccga ggaagaagag   300
ggagggtgtg aactgagagt caaattcagc cgttccgctg atgccccagc ctatcaacag   360
gggcagaatc aactgtataa tgaattgaat ctgggcagga gaagaata cgacgtcctg    420 gataagaggc gaggcagaga ccccgagatg ggcggtaaac cccggcggaa gaaccccccag  480 gaaggcctgt acaacgagct gcagaaggac aagatggctg aggcctactc cgaaatagga   540 atgaagggg agagaaggag aggcaaagga catgacggcc tgtaccaggg actgtctaca   600
gctactaagg acacctatga tgcattgcac atgcaagccc tacccccta a             651

<210> SEQ ID NO 77
<211> LENGTH: 217
<212> TYPE: PRT
<213> ORGANISM: Artificial Sequence
<220> FEATURE:
<223> OTHER INFORMATION: CAR2 construct without scFv (aa)

<400> SEQUENCE: 77

Ile Glu Val Met Tyr Pro Pro Pro Tyr Leu Asp Asn Glu Lys Ser Asn
  1               5                  10                  15

Gly Thr Ile Ile His Val Lys Gly Lys His Leu Cys Pro Ser Pro Leu
             20                  25                  30
```

```
Phe Pro Gly Pro Ser Lys Pro Ile Tyr Ile Trp Ala Pro Leu Ala Gly
         35                  40                  45

Thr Cys Gly Val Leu Leu Leu Ser Leu Val Ile Thr Leu Tyr Cys Lys
 50                  55                  60

Arg Gly Arg Lys Lys Leu Leu Tyr Ile Phe Lys Gln Pro Phe Met Arg
 65                  70                  75                  80

Pro Val Gln Thr Thr Gln Glu Glu Asp Gly Cys Ser Cys Arg Phe Pro
                 85                  90                  95

Glu Glu Glu Glu Gly Gly Cys Glu Leu Arg Val Lys Phe Ser Arg Ser
                100                 105                 110

Ala Asp Ala Pro Ala Tyr Gln Gln Gly Gln Asn Gln Leu Tyr Asn Glu
            115                 120                 125

Leu Asn Leu Gly Arg Arg Glu Glu Tyr Asp Val Leu Asp Lys Arg Arg
        130                 135                 140

Gly Arg Asp Pro Glu Met Gly Gly Lys Pro Arg Arg Lys Asn Pro Gln
145                 150                 155                 160

Glu Gly Leu Tyr Asn Glu Leu Gln Lys Asp Lys Met Ala Glu Ala Tyr
                165                 170                 175

Ser Glu Ile Gly Met Lys Gly Glu Arg Arg Arg Gly Lys Gly His Asp
            180                 185                 190

Gly Leu Tyr Gln Gly Leu Ser Thr Ala Thr Lys Asp Thr Tyr Asp Ala
        195                 200                 205

Leu His Met Gln Ala Leu Pro Pro Arg
    210                 215

<210> SEQ ID NO 78
<211> LENGTH: 1227
<212> TYPE: DNA
<213> ORGANISM: Artificial Sequence
<220> FEATURE:
<223> OTHER INFORMATION: CAR3 construct without scFv (nt)

<400> SEQUENCE: 78
gaaccaaaga gctgcgataa gacccacacc tgtccgccat gtcccgctcc cgaactgctg      60
ggtgggccca gcgtgttcct gtttcctccc aagcccaagg atacgcttat gatctcaaga     120
acgcccgagg tgacatgcgt ggtggttgat gtgagccatg aagaccccga ggtgaagttc     180
aactggtatg tggacggcgt ggaggtgcat aacgctaaaa caaagcctag agaagagcag     240
tataactcga cctacagggt ggttagcgtg ttaactgttc tgcatcagga ctggctcaat     300
ggcaaggagt acaaatgtaa agtgtctaat aaagccctgc cgcccccat gagaaaact      360 attagcaagg ctaaaggaca gcccagagag ccccaggtct ataccttgcc tccatctaga     420
gatgaattaa caaaaaacca ggtatctctt acatgcctgg tgaagggggtt ttacccctca    480 gacatcgccg tggagtggga agtaatggga cagcccgaaa ataattataa gaccacacca    540
cccgtgctgg acagcgatgg cagcttctt ctgtacagca aattgacagt ggataagtcc     600
agatggcaac aagggaatgt cttctcatgt agcgtgatgc acgaggccct gcataaccac    660
tacactcaga agtccctgag tcttagcccc ggcatataca tctgggcacc tctcgccgga    720
acctgtggtg tattactgct gagccttgtg attactctgt attgcaaaag aggccggaag    780
aagctgctgt acatctttaa gcagcccttc atgcggccgg ttcagacaac ccaggaggag    840
gatggctgca gctgccgatt tcccgaagaa gaagagggcg gctgcgagct gagagtgaaa    900
ttctcaagaa gtgctgacgc accagcatac cagcaaggcc agaaccagct gtataacgag    960
ctaaatctgg gcagaagaga agagtacgac gtactggaca gcgcagagg tagagatccc    1020
```

```
gaaatgggggg gcaaaccgcg gagaaagaat cctcaggagg gtctgtataa cgagctgcaa    1080
aaggataaaa tggcagaggc gtacagcgaa atcggcatga aggcgagcg acgccgcggc    1140 aaagggcacg acggcttgta tcagggactt agcactgcca ccaaggacac ttacgatgcc    1200
ctccacatgc aagctctgcc cccaaga                                        1227
```

<210> SEQ ID NO 79
<211> LENGTH: 409
<212> TYPE: PRT
<213> ORGANISM: Artificial Sequence
<220> FEATURE:
<223> OTHER INFORMATION: CAR3 construct without scFv (aa)

<400> SEQUENCE: 79

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ile Tyr Ile Trp Ala Pro Leu Ala Gly
225                 230                 235                 240

Thr Cys Gly Val Leu Leu Leu Ser Leu Val Ile Thr Leu Tyr Cys Lys
                245                 250                 255

Arg Gly Arg Lys Lys Leu Leu Tyr Ile Phe Lys Gln Pro Phe Met Arg
            260                 265                 270

Pro Val Gln Thr Thr Gln Glu Glu Asp Gly Cys Ser Cys Arg Phe Pro
        275                 280                 285

Glu Glu Glu Glu Gly Gly Cys Glu Leu Arg Val Lys Phe Ser Arg Ser
    290                 295                 300

Ala Asp Ala Pro Ala Tyr Gln Gln Gly Gln Asn Gln Leu Tyr Asn Glu
305                 310                 315                 320
```

Leu Asn Leu Gly Arg Arg Glu Glu Tyr Asp Val Leu Asp Lys Arg Arg
            325                 330                 335

Gly Arg Asp Pro Glu Met Gly Gly Lys Pro Arg Arg Lys Asn Pro Gln
        340                 345                 350

Glu Gly Leu Tyr Asn Glu Leu Gln Lys Asp Lys Met Ala Glu Ala Tyr
        355                 360                 365

Ser Glu Ile Gly Met Lys Gly Glu Arg Arg Arg Gly Lys Gly His Asp
    370                 375                 380

Gly Leu Tyr Gln Gly Leu Ser Thr Ala Thr Lys Asp Thr Tyr Asp Ala
385                 390                 395                 400

Leu His Met Gln Ala Leu Pro Pro Arg
            405

<210> SEQ ID NO 80
<211> LENGTH: 675
<212> TYPE: DNA
<213> ORGANISM: Artificial Sequence
<220> FEATURE:
<223> OTHER INFORMATION: CAR4 construct without scFv (nt)

<400> SEQUENCE: 80
accaccaccc ctgcaccaag acctcctact cccgctccga cgatcgctag ccaacctctg      60
agcctgaggc cagaggcgtg tagaccagca gccggcgggg ccgttcacac aagaggcctg     120
gacttcgcct gcgacttctg ggtgctggtt gtggtcggcg agtgttagcg gtgctattcc     180
ctactcgtga ccgtcgcttt tataatcttt tgggtcagaa gtaagagatc tagactcctg     240
catagcgact acatgaatat gactcctaga agacccggtc cgacaagaaa gcactatcag     300
ccctatgctc cacccagaga ttttgcagcc tacagatcaa gagtaaaatt ctctagatcc     360
gcagacgccc cagcatacca gcaaggacaa aatcagttgt acaacgaact gaaccttggt     420
agaagggagg agtatgatgt gctggataag agaagaggca gagatcccga atgggggggg     480
aaaccaagac ggaagaaccc ccaggaggga ttgtataatg aactgcagaa agacaagatg     540
gccgaagctt atagtgagat tgggatgaag ggcgagagaa gaagaggaaa aggtcatgac     600
ggcttgtacc agggactttc aacagccact aaagatacat atgatgctct gcacatgcag     660
gccctccccc ctaga                                                     675

<210> SEQ ID NO 81
<211> LENGTH: 225
<212> TYPE: PRT
<213> ORGANISM: Artificial Sequence
<220> FEATURE:
<223> OTHER INFORMATION: CAR4 construct without scFv (aa)

<400> SEQUENCE: 81

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
        35                  40                  45

Leu Val Val Gly Gly Val Leu Ala Cys Tyr Ser Leu Leu Val Thr
    50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
                    100                 105                 110

Ser Arg Val Lys Phe Ser Arg Ser Ala Asp Ala Pro Ala Tyr Gln Gln
                115                 120                 125

Gly Gln Asn Gln Leu Tyr Asn Glu Leu Asn Leu Gly Arg Arg Glu Glu
        130                 135                 140

Tyr Asp Val Leu Asp Lys Arg Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg
225

<210> SEQ ID NO 82
<211> LENGTH: 648
<212> TYPE: DNA
<213> ORGANISM: Artificial Sequence
<220> FEATURE:
<223> OTHER INFORMATION: CAR5 construct without scFv (nt)

<400> SEQUENCE: 82
actaccaccc cagcgcccag acctcccact cctgctccta ccatcgcaag ccagccgctg      60
tctcttagac cagaggcctg ccgacccgct gccggtgggg cagtgcacac gagaggtctg     120
gacttcgcct gcgatttctg gctccccatt ggctgtgcgg cattcgtcgt cgtttgtatc     180
ctgggatgca ttctgatatg ttggttgacc aaaaagaagt attcaagcag gtgcatgat      240 cctaatggcg agtacatgtt tatgagagca gttaatacag ctaagaaaag cagattaaca     300
gatgtaactc tcagagtgaa gttttctaga tccgctgatg ccccagcata ccagcaagga     360
cagaaccagt tatataacga gctcaacctg ggagaagag aagagtatga tgtgctggac      420
aagcgcagag ggagagaccc agaaatgggt ggcaagccta agagaagaa ccgcaagag       480 ggcctataca cgaactgca gaaagacaaa atggccgagg cctatagcga aatcgggatg     540
aagggagaaa gaaggagagg caaaggacat gatgggttgt accagggcct ctccacagct     600
acaaaagaca cctacgacgc cctgcacatg caggcccttc ccccaaga                 648

<210> SEQ ID NO 83
<211> LENGTH: 216
<212> TYPE: PRT
<213> ORGANISM: Artificial Sequence
<220> FEATURE:
<223> OTHER INFORMATION: CAR5 construct without scFv (aa)

<400> SEQUENCE: 83

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Phe Trp Leu
            35                  40                  45

Pro Ile Gly Cys Ala Ala Phe Val Val Cys Ile Leu Gly Cys Ile
    50              55                  60

Leu Ile Cys Trp Leu Thr Lys Lys Tyr Ser Ser Val His Asp
65              70                  75                  80

Pro Asn Gly Glu Tyr Met Phe Met Arg Ala Val Asn Thr Ala Lys Lys
                85                  90                  95

Ser Arg Leu Thr Asp Val Thr Leu Arg Val Lys Phe Ser Arg Ser Ala
            100                 105                 110

Asp Ala Pro Ala Tyr Gln Gln Gly Gln Asn Gln Leu Tyr Asn Glu Leu
            115                 120                 125

Asn Leu Gly Arg Arg Glu Glu Tyr Asp Val Leu Asp Lys Arg Arg Gly
130                 135                 140

Arg Asp Pro Glu Met Gly Gly Lys Pro Arg Arg Lys Asn Pro Gln Glu
145                 150                 155                 160

Gly Leu Tyr Asn Glu Leu Gln Lys Asp Lys Met Ala Glu Ala Tyr Ser
                165                 170                 175

Glu Ile Gly Met Lys Gly Glu Arg Arg Arg Gly Lys Gly His Asp Gly
            180                 185                 190

Leu Tyr Gln Gly Leu Ser Thr Ala Thr Lys Asp Thr Tyr Asp Ala Leu
            195                 200                 205

His Met Gln Ala Leu Pro Pro Arg
210                 215

<210> SEQ ID NO 84
<211> LENGTH: 801
<212> TYPE: DNA
<213> ORGANISM: Artificial Sequence
<220> FEATURE:
<223> OTHER INFORMATION: CAR6 construct without scFv (nt)

<400> SEQUENCE: 84
acgaccactc cagcccctag acctcccaca cccgctccca caattgcttc acagccattg      60
tcactcagac cagaggcctg cagacctgca gccggaggcg ccgtgcacac cagaggcttg    120
gacttcgctt gtgatttttg ggttctggtt gtcgtcggcg gagtgctggc atgctatagc    180
ctgctcgtaa ctgtggcttt catcattttc tgggtgagaa gcaagagatc cagactgctc    240
catagcgatt acatgaatat gacccccacga agacctggac ccaccagaaa gcattaccaa    300
ccttacgcgc cacctagaga ttttgcagcc tacaggtcta aaagaggagg aaagaagctt    360
ctttacatct ttaaacagcc attcatgaga ccggtccaaa caacccagga gaagacggc     420 tgttcttgca gattcccgga ggaagaggag ggggggtgtg agttaagagt gaagttttct    480
aggagtgctg atgcccctgc ctaccaacaa ggccagaacc agctttataa tgaactgaac    540
ctgggaagaa gaagaataa tgacgtgcta gacaagagaa gaggcagaga tccagaaatg    600 ggggtaagc cccgtcgcaa aaatccccag gagggtctgt acaacgaact gcagaaagac    660
aaaatggctg aggcatatag tgagatcggg atgaagggag agaggagaag aggaaaaggt    720
cacgacggtc tctatcaggg cctgtccact gccaccaaag acacatatga tgcgttgcac    780
atgcaggccc tgccccccag g                                              801

<210> SEQ ID NO 85
<211> LENGTH: 267
<212> TYPE: PRT
<213> ORGANISM: Artificial Sequence
<220> FEATURE:
<223> OTHER INFORMATION: CAR6 construct without scFv (aa)

<400> SEQUENCE: 85

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
        35                  40                  45

Leu Val Val Val Gly Gly Val Leu Ala Cys Tyr Ser Leu Leu Val Thr
    50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
            100                 105                 110

Ser Lys Arg Gly Arg Lys Lys Leu Leu Tyr Ile Phe Lys Gln Pro Phe
        115                 120                 125

Met Arg Pro Val Gln Thr Thr Gln Glu Glu Asp Gly Cys Ser Cys Arg
    130                 135                 140

Phe Pro Glu Glu Glu Glu Gly Gly Cys Glu Leu Arg Val Lys Phe Ser
145                 150                 155                 160

Arg Ser Ala Asp Ala Pro Ala Tyr Gln Gln Gly Gln Asn Gln Leu Tyr
                165                 170                 175

Asn Glu Leu Asn Leu Gly Arg Arg Glu Glu Tyr Asp Val Leu Asp Lys
            180                 185                 190

Arg Arg Gly Arg Asp Pro Glu Met Gly Gly Lys Pro Arg Arg Lys Asn
        195                 200                 205

Pro Gln Glu Gly Leu Tyr Asn Glu Leu Gln Lys Asp Lys Met Ala Glu
    210                 215                 220

Ala Tyr Ser Glu Ile Gly Met Lys Gly Glu Arg Arg Arg Gly Lys Gly
225                 230                 235                 240

His Asp Gly Leu Tyr Gln Gly Leu Ser Thr Ala Thr Lys Asp Thr Tyr
                245                 250                 255

Asp Ala Leu His Met Gln Ala Leu Pro Pro Arg
            260                 265

<210> SEQ ID NO 86
<211> LENGTH: 774
<212> TYPE: DNA
<213> ORGANISM: Artificial Sequence
<220> FEATURE:
<223> OTHER INFORMATION: CAR7 construct without scFv (nt)

<400> SEQUENCE: 86
actaccacgc cgcccccag gcccctaca ccagcaccaa ccattgcaag tcagcccctg      60
tcactcagac cggaagcttg ccgcccggca gctgggggtg ccgtccacac aagaggactc     120
gacttcgcgt gtgatttctg gctccctata gggtgtgccg cattcgtcgt tgtgtgcatc    180
ctgggatgta tcctgatctg ctggctgact aagaagaagt actcctctag cgtgcacgac    240
ccaaacggcg aatacatgtt catgagagct gtgaatactc caagaaatc aaggctgacc     300 gatgtgacgc tgaaacgtgg gagaaagaag ttgttatata ttttaaaca gccttttatg     360 agaccagtgc aaacaactca ggaggaagac ggctgttctt gcagatttcc tgaggaagag    420
gagggaggct gcgagctcag ggttaaattt tctagaagcg ctgacgcacc cgcgtaccag    480

```
cagggacaga accaactgta caatgagctt aacctgggca gacgagaaga atatgatgta    540
ttggataaaa gaagaggaag agatcctgag atgggtggca agcctagacg taagaaccca    600 cagggagggcc tgtataatga gctacagaag gacaaaatgg ctgaagccta cagcgagatt   660
ggtatgaaag gcgagagaag aagagggaaa ggccatgacg gtctgtatca aggcttgtcc    720
accgccacaa aggataccta cgacgccctt catatgcagg cccttcctcc caga          774
```

<210> SEQ ID NO 87
<211> LENGTH: 258
<212> TYPE: PRT
<213> ORGANISM: Artificial Sequence
<220> FEATURE:
<223> OTHER INFORMATION: CAR7 construct without scFv (aa)

<400> SEQUENCE: 87

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Leu
        35                  40                  45

Pro Ile Gly Cys Ala Ala Phe Val Val Val Cys Ile Leu Gly Cys Ile
    50                  55                  60

Leu Ile Cys Trp Leu Thr Lys Lys Lys Tyr Ser Ser Ser Val His Asp
65                  70                  75                  80

Pro Asn Gly Glu Tyr Met Phe Met Arg Ala Val Asn Thr Ala Lys Lys
                85                  90                  95

Ser Arg Leu Thr Asp Val Thr Leu Lys Arg Gly Arg Lys Lys Leu Leu
            100                 105                 110

Tyr Ile Phe Lys Gln Pro Phe Met Arg Pro Val Gln Thr Thr Gln Glu
        115                 120                 125

Glu Asp Gly Cys Ser Cys Arg Phe Pro Glu Glu Glu Glu Gly Gly Cys
    130                 135                 140

Glu Leu Arg Val Lys Phe Ser Arg Ser Ala Asp Ala Pro Ala Tyr Gln
145                 150                 155                 160

Gln Gly Gln Asn Gln Leu Tyr Asn Glu Leu Asn Leu Gly Arg Arg Glu
                165                 170                 175

Glu Tyr Asp Val Leu Asp Lys Arg Arg Gly Arg Asp Pro Glu Met Gly
            180                 185                 190

Gly Lys Pro Arg Arg Lys Asn Pro Gln Glu Gly Leu Tyr Asn Glu Leu
        195                 200                 205

Gln Lys Asp Lys Met Ala Glu Ala Tyr Ser Glu Ile Gly Met Lys Gly
    210                 215                 220

Glu Arg Arg Arg Gly Lys Gly His Asp Gly Leu Tyr Gln Gly Leu Ser
225                 230                 235                 240

Thr Ala Thr Lys Asp Thr Tyr Asp Ala Leu His Met Gln Ala Leu Pro
                245                 250                 255

Pro Arg
```

<210> SEQ ID NO 88
<211> LENGTH: 63
<212> TYPE: DNA
<213> ORGANISM: Artificial Sequence
<220> FEATURE:
<223> OTHER INFORMATION: T2A Nucleotide sequence

<400> SEQUENCE: 88

```
ggctccggcg agggcagggg aagtcttcta acatgcgggg acgtggagga aaatcccggc    60
cca                                                                  63
```

<210> SEQ ID NO 89
<211> LENGTH: 720
<212> TYPE: DNA
<213> ORGANISM: Artificial Sequence
<220> FEATURE:
<223> OTHER INFORMATION: GFP Nucleotide sequence

<400> SEQUENCE: 89

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcaccta cggcgtgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaag gtctatatca ccgccgacaa gcagaagaac   480
ggcatcaagg tgaacttcaa gacccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 90
<211> LENGTH: 783
<212> TYPE: DNA
<213> ORGANISM: Artificial Sequence
<220> FEATURE:
<223> OTHER INFORMATION: T2A-GFP Nucleotide sequence

<400> SEQUENCE: 90

```
ggctccggcg agggcagggg aagtcttcta acatgcgggg acgtggagga aaatcccggc    60
ccaatggtga agggcgga ggagctgttc accggggtgg tgcccatcct ggtcgagctg   120
gacggcgacg taaacggcca agttcagc gtgtccggcg agggcgaggg cgatgccacc   180
tacggcaagc tgaccctgaa gttcatctgc accaccggca agctgcccgt gccctggccc   240
accctcgtga ccaccttcac ctacggcgtg cagtgcttcg cccgctaccc cgaccacatg   300
aagcagcacg acttcttcaa gtccgccatg cccgaaggct acgtccagga gcgcaccatc   360
ttcttcaagg acgacggcaa ctacaagacc cgcgccgagg tgaagttcga gggcgacacc   420
ctggtgaacc gcatcgagct gaagggcatc gacttcaagg aggacggcaa catcctgggg   480
cacaagctgg agtacaacta caacagccac aaggtctata tcaccgccga caagcagaag   540
aacggcatca aggtgaactt caagacccgc cacaacatcg aggacggcag cgtgcagctc   600
gccgaccact accagcagaa cacccccatc ggcgacggcc ccgtgctgct gcccgacaac   660
cactacctga gcacccagtc cgccctgagc aaagacccca acgagaagcg cgatcacatg   720
gtcctgctgg agttcgtgac cgccgccggg atcactctcg gcatggacga gctgtacaag   780
taa                                                                  783
```

<210> SEQ ID NO 91

<211> LENGTH: 1184
<212> TYPE: DNA
<213> ORGANISM: Artificial Sequence
<220> FEATURE:
<223> OTHER INFORMATION: EF-1 alpha Nucleotide sequence

<400> SEQUENCE: 91

```
tgtgaggctc cggtgcccgt cagtgggcag agcgcacatc gcccacagtc cccgagaagt    60
tgggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctgggc cgccgcgtgc gaatctggtg gcaccttcgc gcctgtctcg    480
ctgctttcga taagtctcta gccatttaaa atttttgatg acctgctgcg acgctttttt    540
tctggcaaga tagtcttgta aatgcgggcc aagatctgca cactggtatt tcggtttttg    600
gggccgcggg cggcgacggg gcccgtgcgt cccagcgcac atgttcggcg aggcggggcc    660
tgcgagcgcg gccaccgaga tcggacgggg gtagtctca agctggccgg cctgctctgg    720
tgcctggcct cgcgccgccg tgtatcgccc gccctgggc ggcaaggctg gcccggtcgg    780
caccagttgc gtgagcggaa agatggccgc ttcccggccc tgctgcaggg agctcaaaat    840
ggaggacgcg cgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag gggttttatg   1020
cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                     1184
```

<210> SEQ ID NO 92
<211> LENGTH: 556
<212> TYPE: PRT
<213> ORGANISM: Artificial Sequence
<220> FEATURE:
<223> OTHER INFORMATION: amino acid sequence of hCD19 (UniProtKB: P15391)

<400> SEQUENCE: 92

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110
```

```
Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525
```

```
Asp Ser Tyr Glu Asn Met Asp Asn Pro Asp Gly Pro Asp Pro Ala Trp
        530             535             540

Gly Gly Gly Gly Arg Met Gly Thr Trp Ser Thr Arg
545             550             555

<210> SEQ ID NO 93
<211> LENGTH: 537
<212> TYPE: PRT
<213> ORGANISM: Artificial Sequence
<220> FEATURE:
<223> OTHER INFORMATION: amino acid sequence of cCD19 (UniProtKB:
      G7Q0T7)

<400> SEQUENCE: 93

Met Pro Pro Pro Cys Leu Leu Phe Phe Leu Leu Phe Leu Thr Pro Met
1               5                   10                  15

Glu Val Arg Pro Gln Glu Pro Leu Val Val Lys Val Glu Glu Gly Asp
            20                  25                  30

Asn Ala Val Leu Gln Cys Leu Glu Gly Thr Ser Asp Gly Pro Thr Gln
        35                  40                  45

Gln Leu Val Trp Cys Arg Asp Ser Pro Phe Glu Pro Phe Leu Asn Leu
    50                  55                  60

Ser Leu Gly Leu Pro Gly Met Gly Ile Arg Met Gly Pro Leu Gly Ile
65                  70                  75                  80

Trp Leu Leu Ile Phe Asn Val Ser Asn Gln Thr Gly Gly Phe Tyr Leu
                85                  90                  95

Cys Gln Pro Gly Leu Pro Ser Glu Lys Ala Trp Gln Pro Gly Trp Thr
            100                 105                 110

Val Ser Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Asn Ser Ser Gln Leu Tyr Val Trp Ala
145                 150                 155                 160

Lys Asp Arg Pro Glu Met Trp Glu Gly Glu Pro Val Cys Gly Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val Arg Pro Lys Gly Pro Lys Ser
    210                 215                 220

Ser Leu Leu Ser Leu Glu Leu Lys Asp Asp Arg Pro Asp Arg Asp Met
225                 230                 235                 240

Trp Val Val Asp Thr Gly Leu Leu Leu Thr Arg Ala Thr Ala Gln Asp
                245                 250                 255

Ala Gly Lys Tyr Tyr Cys His Arg Gly Asn Trp Thr Lys Ser Phe Tyr
            260                 265                 270

Leu Glu Ile Thr Ala Arg Pro Ala Leu Val Leu Arg Arg Lys Arg Lys
        275                 280                 285

Arg Met Thr Asp Pro Thr Arg Arg Phe Phe Lys Val Thr Pro Pro Pro
    290                 295                 300

Gly Ser Gly Pro Gln Asn Gln Tyr Gly Asn Val Leu Ser Leu Pro Thr
305                 310                 315                 320

Pro Thr Ser Gly Leu Gly Arg Ala Gln Arg Trp Ala Ala Gly Leu Gly
                325                 330                 335
```

```
Gly Thr Ala Pro Ser Tyr Gly Asn Pro Ser Ser Asp Val Gln Val Asp
            340             345             350
Gly Ala Val Gly Ser Arg Ser Pro Pro Glu Ala Gly Pro Glu Glu Glu
            355             360             365
Glu Gly Glu Gly Tyr Glu Glu Pro Asp Ser Glu Glu Gly Ser Glu Phe
    370             375             380
Tyr Glu Asn Asp Ser Asn Phe Gly Gln Asp Gln Leu Ser Gln Asp Gly
385             390             395             400
Ser Gly Tyr Glu Asn Pro Glu Asp Glu Pro Leu Gly Pro Glu Asp Glu
            405             410             415
Asp Ser Phe Ser Asn Ala Glu Ser Tyr Glu Asn Glu Asp Glu Glu Leu
            420             425             430
Thr Gln Pro Val Ala Arg Thr Met Asp Phe Leu Ser Pro His Gly Ser
            435             440             445
Ala Trp Asp Pro Ser Arg Glu Ala Thr Ser Leu Gly Cys Thr Ser Arg
    450             455             460
Ala Leu Ala Ser Asn Ser Pro Ser Pro Ala Gln Ala Gly Ser Gln Ser
465             470             475             480
Tyr Glu Asp Met Arg Gly Leu Leu Tyr Ala Ala Pro Gln Leu Arg Thr
            485             490             495
Ile Arg Gly Gln Pro Gly Pro Asn His Glu Glu Asp Ala Asp Ser Tyr
            500             505             510
Glu Asn Met Asp Asn Pro Asp Gly Pro Asp Pro Ala Trp Gly Gly Gly
            515             520             525
Gly Arg Met Gly Thr Trp Ser Ala Arg
            530             535
```